United States Patent [19]

Isaacs et al.

[11] Patent Number: 5,932,606

[45] Date of Patent: Aug. 3, 1999

[54] PYRAZINONE, PYRIDINONE, PIPERIDINE AND PYRROLIDINE THROMBIN INHIBITORS

[75] Inventors: Richard C. A. Isaacs, Harleysville; Adel M. Naylor-Olsen, Lansdale; Bruce D. Dorsey, Maple Glen; Christina L. Newton, Harleysville, all of Pa.

[73] Assignee: Merck & Co., Inc., Rahway, N.J.

[21] Appl. No.: 09/049,639

[22] Filed: Mar. 20, 1998

Related U.S. Application Data

[60] Provisional application No. 60/041,543, Mar. 24, 1997, and provisional application No. 60/047,561, May 22, 1997.

[51] Int. Cl.$^6$ ...................... A61K 31/415; A61K 31/495; C07D 403/12
[52] U.S. Cl. ...................... 514/397; 514/235.8; 514/255; 514/326; 514/341; 514/342; 514/343; 514/370; 514/392; 514/400; 544/120; 544/131; 544/132; 544/405; 544/406; 544/407; 546/208; 546/272.7; 546/275.1; 548/195; 548/338.1; 548/331.5; 548/204
[58] Field of Search .................. 514/235.8, 255, 514/318, 326, 341, 342, 343, 370, 397; 544/120, 131, 132, 405, 406, 407; 546/194, 208, 269.7, 272.7, 275.1; 548/195, 338.1, 338.5

[56] References Cited

U.S. PATENT DOCUMENTS

| | | | |
|---|---|---|---|
| 5,260,307 | 11/1993 | Ackermann et al. | 514/323 |
| 5,405,854 | 4/1995 | Ackermann et al. | 514/315 |
| 5,510,369 | 4/1996 | Lumma et al. | 514/422 |

FOREIGN PATENT DOCUMENTS

| | | |
|---|---|---|
| WO 94/25051 | 11/1994 | WIPO . |
| WO 96/11697 | 4/1996 | WIPO . |
| WO 96/31504 | 10/1996 | WIPO . |
| WO 96/32110 | 10/1996 | WIPO . |
| WO 97/01338 | 1/1997 | WIPO . |

*Primary Examiner*—Yogendra N. Gupta
*Attorney, Agent, or Firm*—Richard S. Parr; Melvin Winokur

[57] ABSTRACT

A compound which inhibits human thrombin and where has the structure

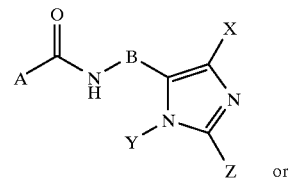

or

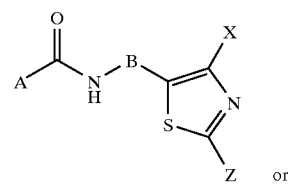

or

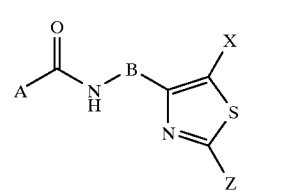

and pharmaceutically acceptable salts thereof, wherein such as

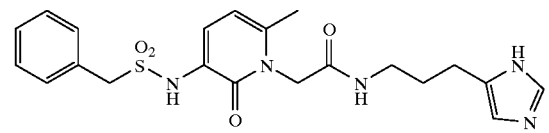

which are useful for inhibiting formation of blood platelet aggregates in blood in a mammal.

8 Claims, No Drawings

PYRAZINONE, PYRIDINONE, PIPERIDINE AND PYRROLIDINE THROMBIN INHIBITORS

CROSS-REFERENCE TO RELATED APPLICATIONS

This patent application is a non-provisional patent application claiming priority to U.S. provisional application Ser. No. 60/041,543, filed Mar. 24, 1997 and U.S. provisional application Ser. No. 60/047,561, filed May 22, 1997.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.* (1992) vol. 114, pp. 1854–63, describes peptidyl α-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoiminomethyl)amino]butyl]-1-[N-(2-naphthalenylsulfonyl)-L-phenylalanyl]-L-prolinamide.

WO 94/29336 describes compounds which are useful as thrombin inhibitors.

SUMMARY OF THE INVENTION

The invention relates to compounds of the formula:

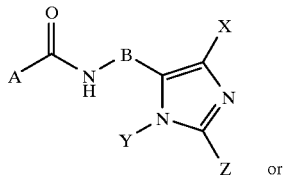 or

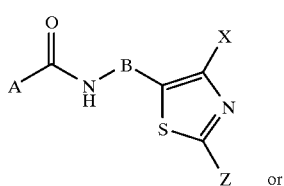 or

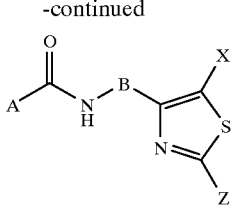

and pharmaceutically acceptable salts thereof, wherein
A is selected from the group consisting of

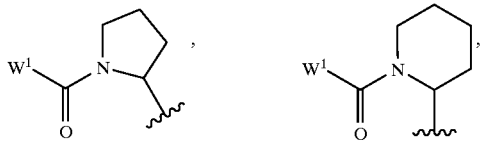

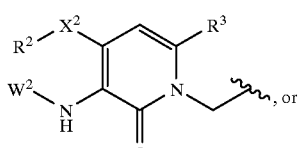

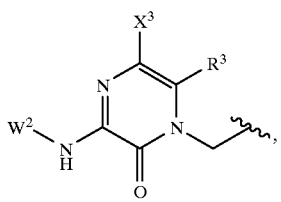

wherein
$W^1$ is

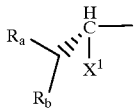

wherein
$R_a$ and $R_b$ are independently selected from hydrogen,
a heterocyclic group which is a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring,
$C_{1-4}$ alkyl unsubstituted or substituted with $CH_3$ or $C_{3-7}$ cloalkyl,
aryl,
substituted aryl with one or two substituents selected from
  $C_{1-4}$ alkyl,
  $C_{1-4}$ alkoxy,
  methylenedioxy,
  halogen or
  hydroxy,
$C_{3-7}$ cycloalkyl, $C_{9-10}$ bicycloalkyl, or $R_a$ and $R_b$, along with the carbon to which they are attached, form a $C_{3-7}$ cycloalkyl ring or

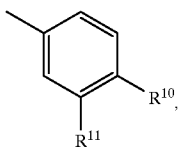

where $R^{10}$ is H or —OH, and
$R^{11}$ is H or —OCH$_3$, and
$X^1$ is selected from the group consisting of
—OH
—NH$_2$
—NHCH$_3$,
—NH(CH$_2$)$_{1-3}$CH$_3$,
—NH(CH$_2$)$_{2-4}$OH,
—NH(CH$_2$)$_{1-3}$COOH,
—NH(CH$_2$)$_{1-3}$COOR$^6$, where $R^6$ is $C_{1-4}$alkyl,
—NH(CH$_2$)$_{1-3}$CONR$^7$R$^8$,
where $R^7$ and $R^8$ are independently hydrogen or $C_{1-4}$alkyl,

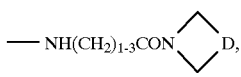

where D is 1, 2, 3, or 4 carbon atoms unsubstituted or any 1, 2, 3, or 4 of which are substituted with OH,
—NHSO$_2$(CH$_2$)$_{1-3}$aryl,
—NH(CH$_2$)$_{1-3}$NH$_2$,
—NHC$_{3-7}$ cycloalkyl ring unsubstituted or substituted with —OH, —C(O)OH, or —C(O)OR$_c$, where R$_c$ is $C_{1-4}$ alkyl,

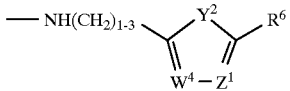

where
$Y^2$ is O or NH,
$W^4$ is C or N,
$Z^1$ is C or N, and
$R^6$ is —CH$_2$OH or —N(CH$_3$)$_2$ provided that $W^4$ and $Z^1$ are not the same,

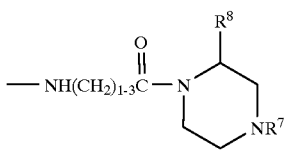

where
$R^7$ is H or CH$_3$, and
$R^8$ is H or

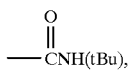

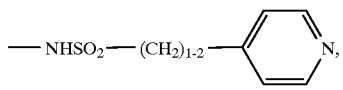

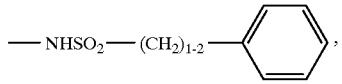

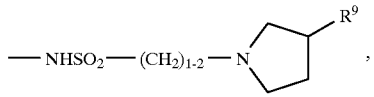

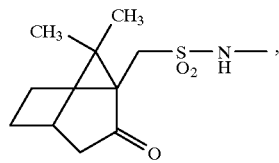

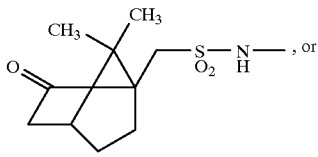

—NHSO$_2$—(CH$_2$)$_{1-2}$—NH—(CH$_2$)$_2$NH$_2$
where $R^9$ is H, NH$_2$, or OH;
or
$W^1$ is

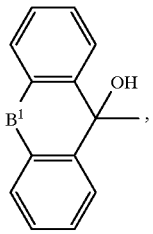

wherein $B^1$ is a bond, O, —CH$_2$—O— or —O—CH$_2$—;
$W^2$ is
hydrogen,
$R^1$—,
$R^1$OC(O)—,
$R^1$C(O)—,
$R^1$SO$_2$—,
$(R^1)_2$CH(CH$_2$)$_{0-4}$NHC(O)—,
$(R^1)_m$(CH$_2$)$_n$NHqC(O)—,
where n is 0–4, m is 1 or 2, wherein $R^1$ is same or different, and q is 0 or 1, with the proviso that where n is 1–4, q is 1 and m is 1, and where n is 0, m is 1 or 2, and q is 0 or 1, and where n is 0, m is 2 and q is 0;
$R^1$ is
$R^{17}$(CH$_2$)$_t$—, where t is 0–4,
$(R^{17})(OR^{17})$CH(CH$_2$)$_p$—, where p is 1–4,
$(R^{17})_2$CH(CH$_2$)$_r$—, where r is 0–4 and each $R^{17}$ can be the same or different, and wherein $(R^{17})_2$ can also form a ring with CH represented by $C_{3-7}$ cycloalkyl, $C_{7-12}$ bicylic alkyl, $C_{10-16}$ tricylic alkyl, or a 5- to 7- membered mono- or bicyclic heterocyclic ring which can be saturated or unsaturated, and which contains from one to three heteroatoms selected from the group consisting of N, O and S, $R^{17}O(CH_2)_p$—, wherein p is 1–4;

$R^2$ and $R^{17}$ are independently selected from
- —phenyl, unsubstituted or substituted with one or more of
  - $C_{1-4}$ alkyl,
  - $C_{1-4}$ alkoxy,
  - halogen,
  - hydroxy,
  - COOH, or
  - $CONH_2$,
- naphthyl,
- biphenyl,
- a 5- to 7- membered mono- or a 9- to 10-membered bicyclic heterocyclic ring which can be saturated or unsaturated, and which contains from one to four heteroatoms selected from the group consisting of N, O and S,
- —$C_{1-7}$ alkyl, unsubstituted or substituted with one or more of
  - hydroxy,
  - COOH,
  - amino,
  - aryl,
  - $C_{3-7}$ cycloalkyl,
  - heteroaryl, or
  - heterocycloalkyl,
- —$CF_3$
- $C_{3-7}$ cycloalkyl,
- $C_{7-12}$ bicyclic alkyl, or
- $C_{10-16}$ tricyclic alkyl;

$X^2$ is
- $CF_2$,
- $CR^{15},R^{16}$
  - wherein $R^{15}$ and $R^{16}$ are independently
    - hydrogen,
    - $C_{3-7}$ cycloalkyl,
    - $C_{1-4}$ alkyl unsubstituted or substituted with one or more of
      - hydroxy,
      - COOH,
      - amino,
      - aryl,
      - heteroaryl, or
      - heterocycloalkyl,
    - aryl,
    - heteroaryl,
    - heterocycloalkyl, or
    - $R^{15}$ and $R^{16}$ are joined to form a four to seven membered cycloalkyl ring unsubstituted or substituted with hydroxy, amino or aryl, or
- $S(O)_r$, where r is 0–2;

$X^3$ is hydrogen or halogen;

$R^3$ and $R^{18}$ are independently selected from the group consisting of
- hydrogen,
- $C_{1-4}$ alkyl,
- $C_{3-7}$ cycloalkyl, or
- trifluoromethyl;

B is selected from the group consisting of
- $C_{1-4}$ alkyl,
- $C_{3-4}$ alkenyl, and
- $C_{3-4}$ alkynyl;

X is selected from the group consisting of
- hydrogen,
- halogen,
- —$CF_3$,
- —$CH_2CF_3$,
- —$C_{3-5}$ cyclolakyl,
- —$CH_2C_{3-5}$ cycloalkyl, and
- —$C_{1-4}$ alkyl;

Z is selected from the group consisting of
- hydrogen,
- —$NH_2$,
- —$C_{1-4}$ alkylamino,
- —$C_{1-4}$ alkanol,
- —$C_{1-4}$ alkyl; and Y is selected from the group consisting of
- hydrogen, and
- —$C_{1-7}$ alkyl,
- —$CH_2CH_2CH_2CH_2C_{3-6}$ cycloalkyl,
- —$CH_2CH=CHCH_2C_{3-6}$ cycloalkyl,
- —$CH_2C\equiv CCH_2C_{3-6}$ cycloalkyl,
- —$CH_2C\equiv CCH_2CH_2C_{3-6}$ cycloalkyl:
- —$CH_2CH_2CH_2CH_2CH_2C_{3-6}$ cyclolakyl,
- —$CH_2CH=CHCH_2CH_2C_{3-6}$ cycloalkyl, and
- —$CH_2COY^1$, wherein $Y^1$ is selected from the group consisting of
  - —$OC_{1-7}$ alkyl,
  - —OH,
  - —$C_{1-6}$ alkyl,
  - —$C_{3-6}$ cyclolalkyl,
  - —$CH_2C_{3-6}$ cycloalkyl,
  - —$CH_2CH_2C_{3-6}$ cycloalkyl,
  - —benzyl
  - —$CH_2$benzyl
  - —$NH_2$,
  - —$NHC_{1-5}$ alkyl,
  - —$NHC_{1-4}$ alkyl$CF_3$,
  - —$NHC_{2-4}$ alkanol,
  - —$NHC_{2-4}$ alkylamino,

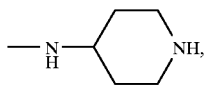

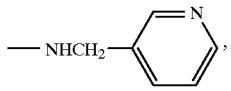

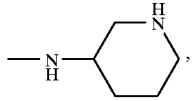

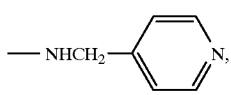

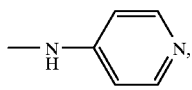

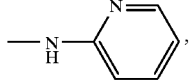

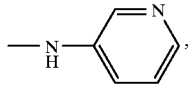

-continued

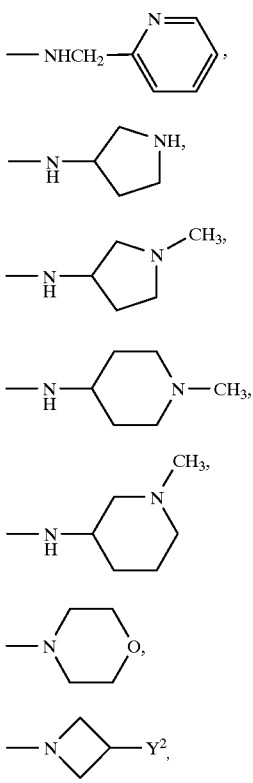

wherein $Y^2$ is H, $NH_2$ or OH,

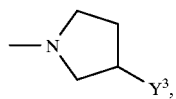

wherein $Y^3$ is H, $NH_2$ or OH, and

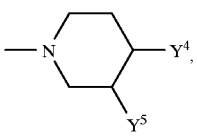

wherein
$Y^4$ is hydrogen, and
$Y^5$ is $NH_2$ or OH, or H
$Y^5$ is hydrogen, and
$Y^4$ is $NH_2$ or OH.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION

In one class of the invention, the compounds have the formula

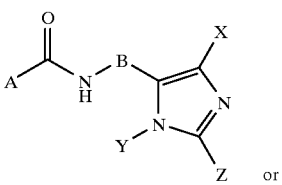

or

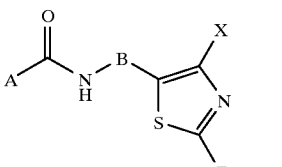

or

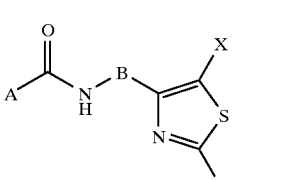

and pharmaceutically acceptable salts thereof, wherein

A is selected from the group consisting of

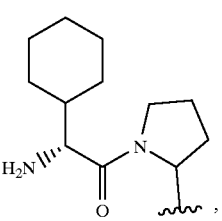

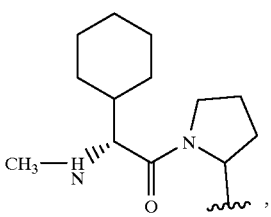

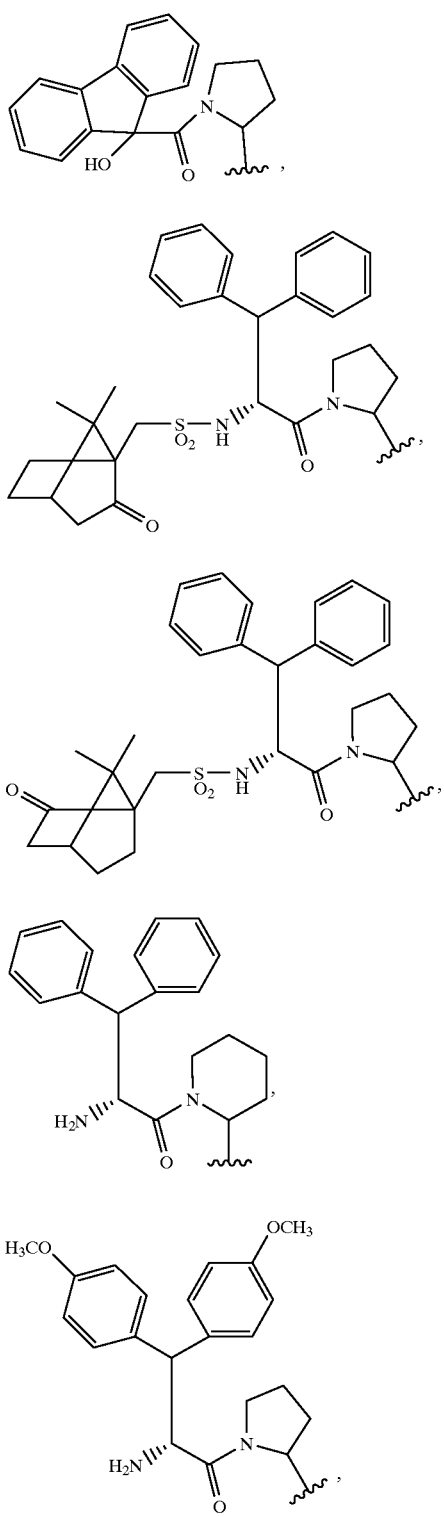
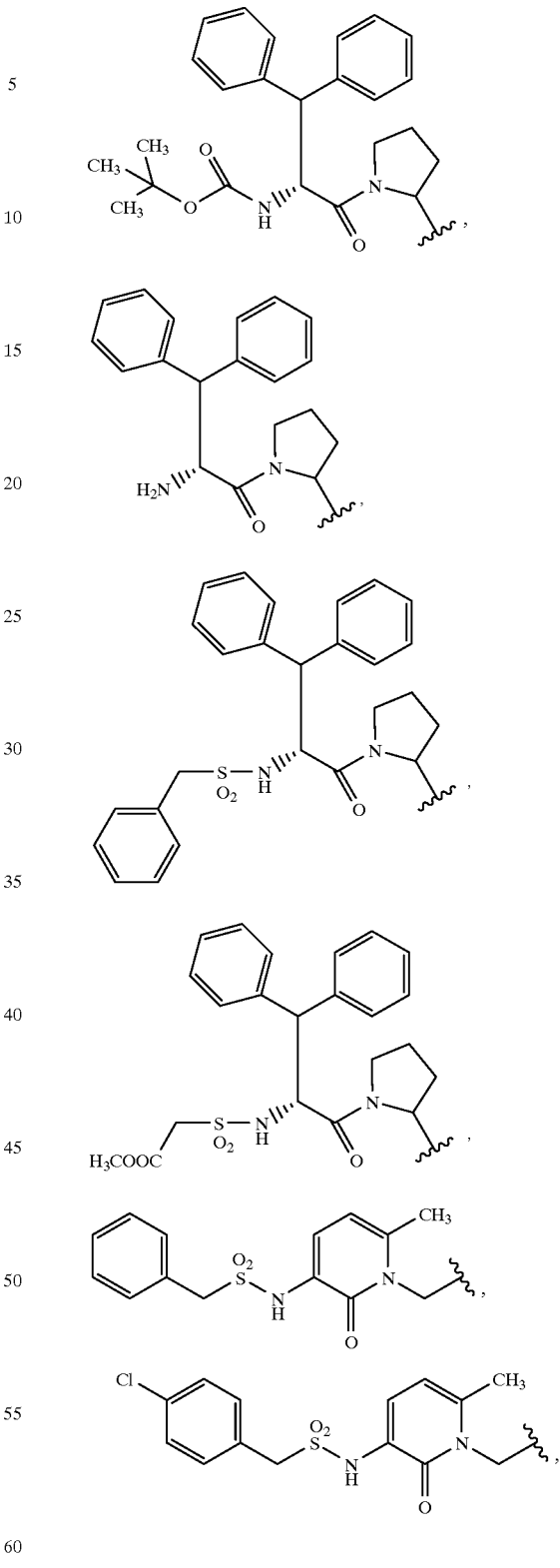

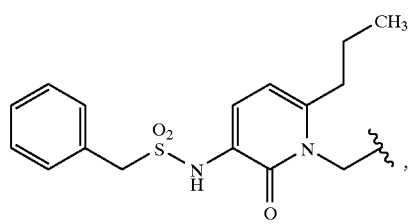

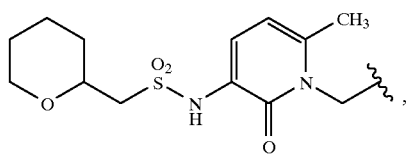

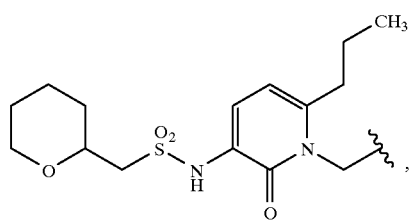

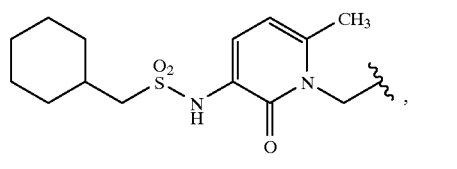

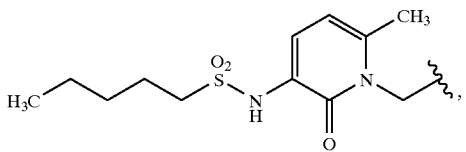

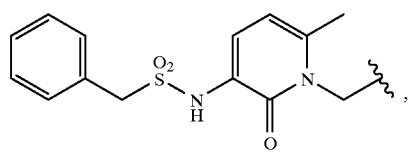

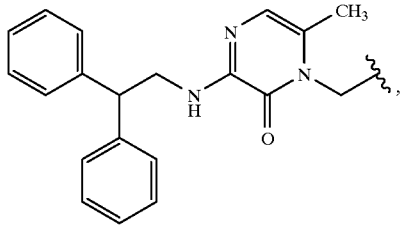

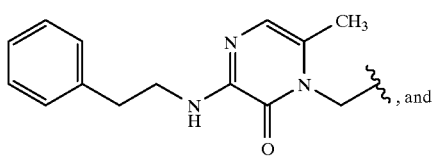

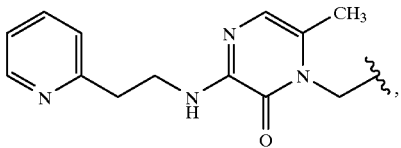

In one group of this class of the invention, the compounds have the formula

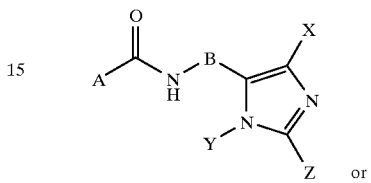

or

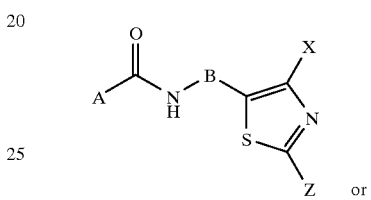

or

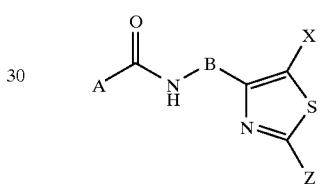

and pharmaceutically acceptable salts thereof, wherein
B is selected from the group consisting of:
—CH$_2$CH=CH—,
—CH$_2$CH$_2$CH$_2$—,
—CH$_2$C≡C—, and
—CH$_2$—;
X is
H,
—CH$_3$,
Cl
Z is
H,
—NH$_2$, and
Y is selected from the group consisting of
hydrogen,
—CH$_2$COOC(CH$_3$)$_3$,
—CH$_2$COOH,
—CH$_2$CONHC(CH$_3$)$_3$,
—CH$_2$CONHCH$_2$CH$_3$,

—CH$_2$CONH—△,

—CH$_2$CONHCH$_2$—△,

-continued
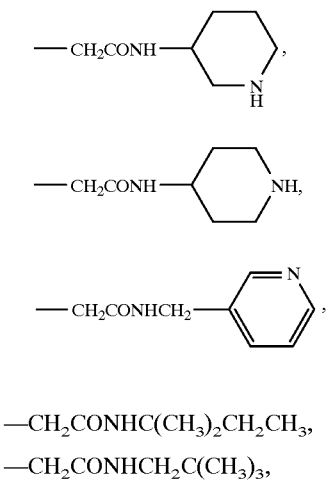
—CH₂CONHC(CH₃)₂CH₂CH₃,
—CH₂CONHCH₂C(CH₃)₃,
—CH₂CONHCH₂CF₃,
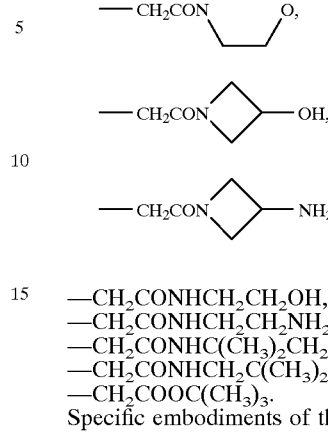
—CH₂CONHCH₂CH₂OH,
—CH₂CONHCH₂CH₂NH₂,
—CH₂CONHC(CH₃)₂CH₂NH₂,
—CH₂CONHCH₂C(CH₃)₂NH₂,
—CH₂COOC(CH₃)₃.
Specific embodiments of the class include
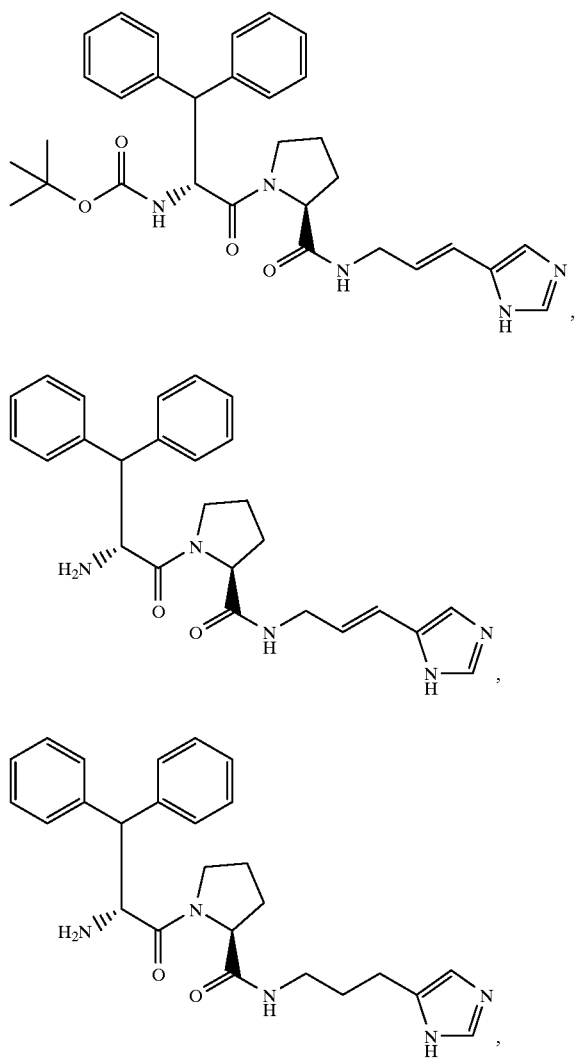

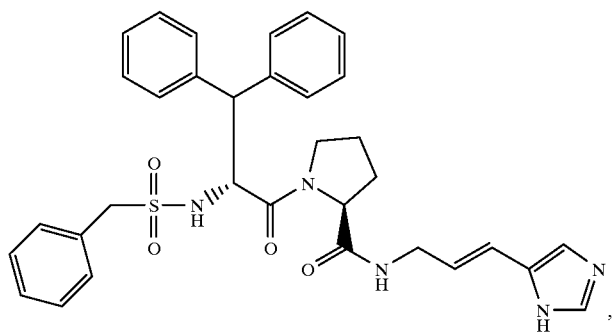
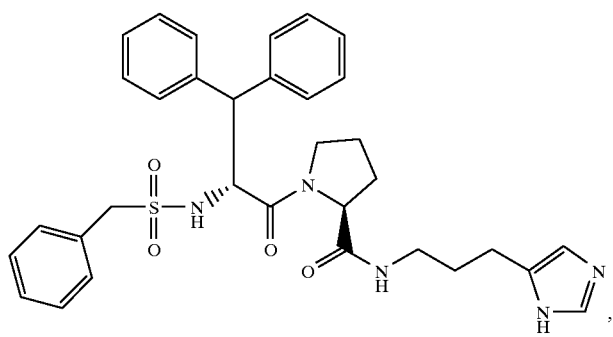
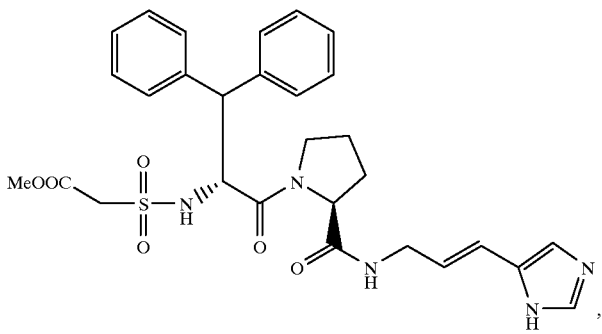
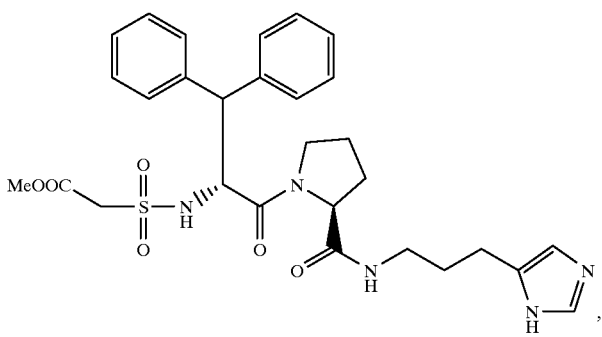

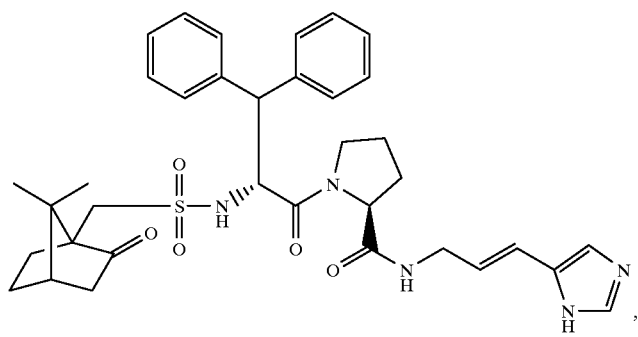
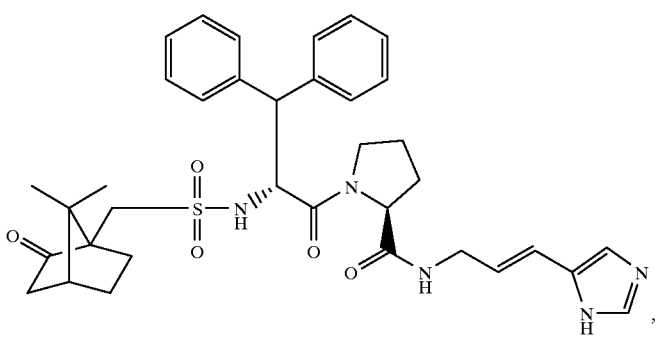
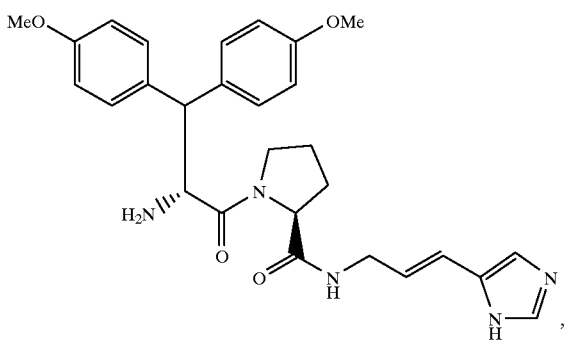
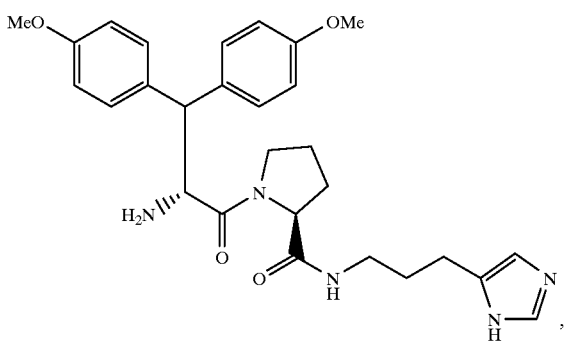

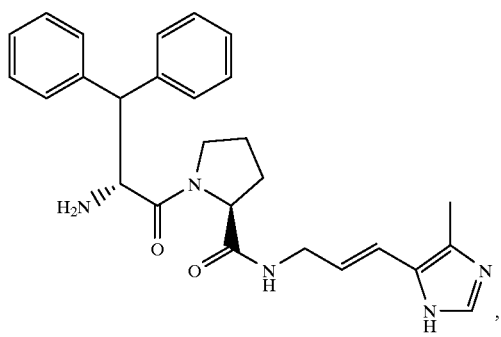
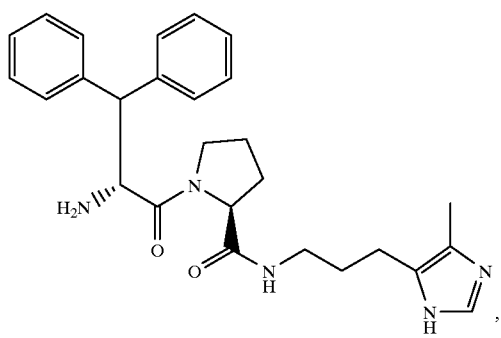
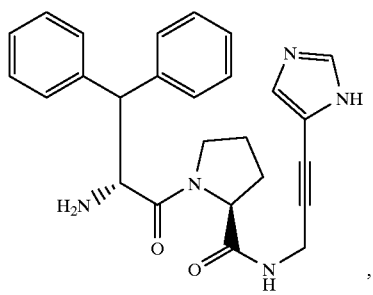
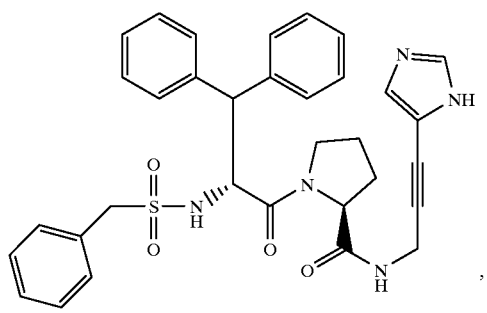
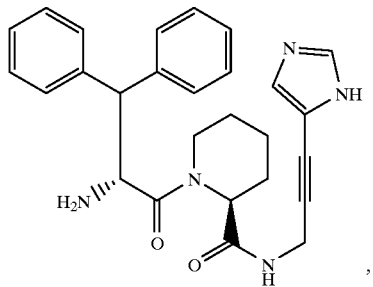

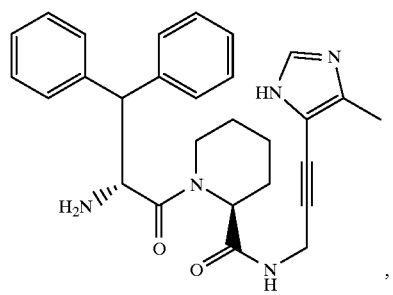
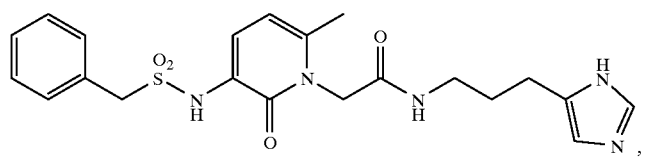
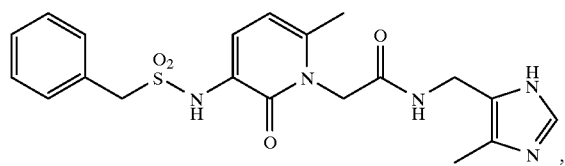
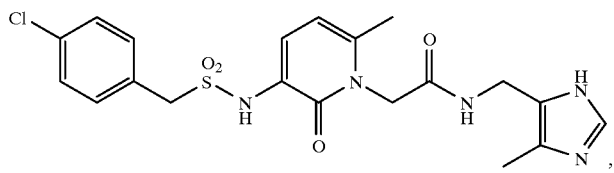
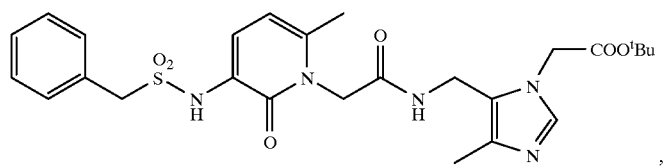
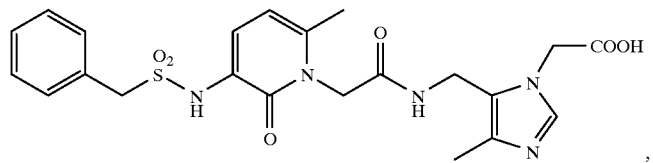
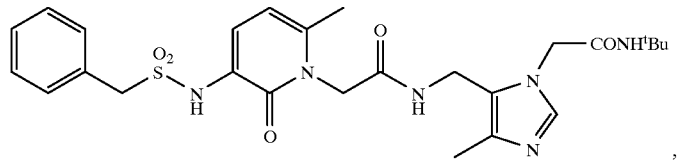
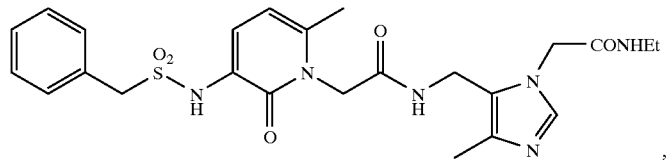

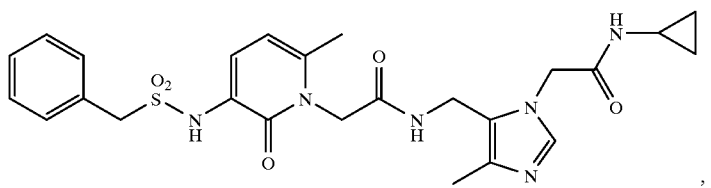,
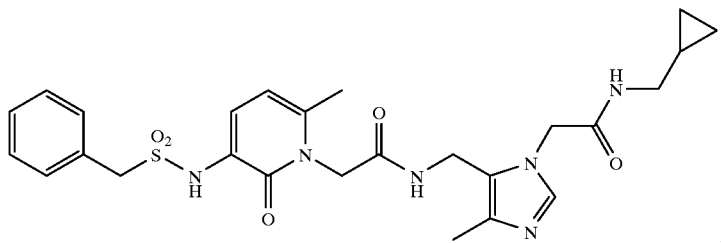,
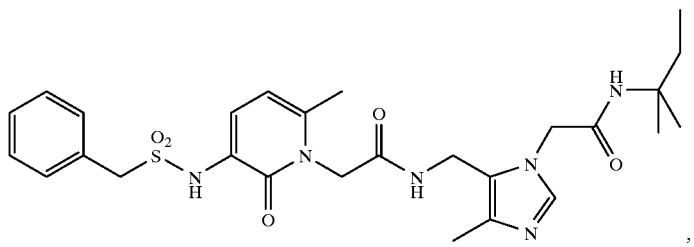,
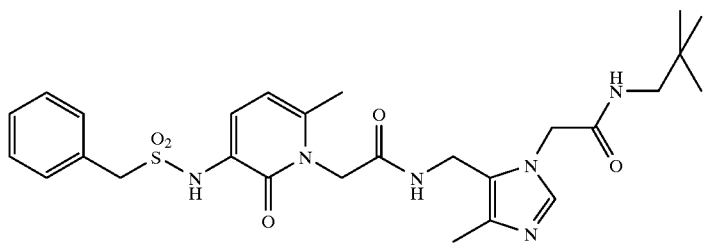,
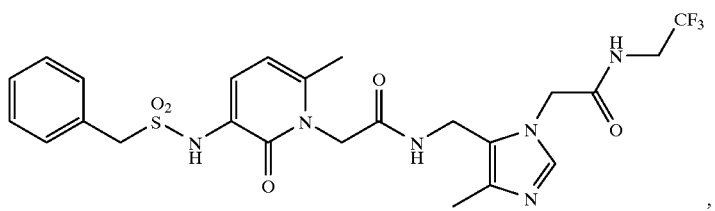,
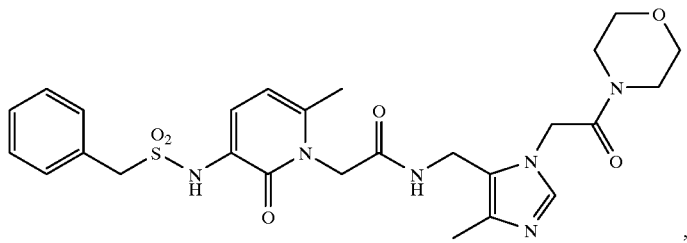,

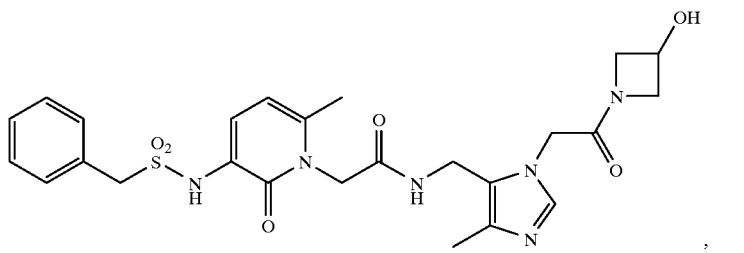,
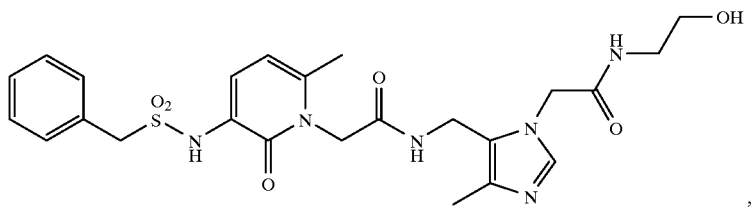,
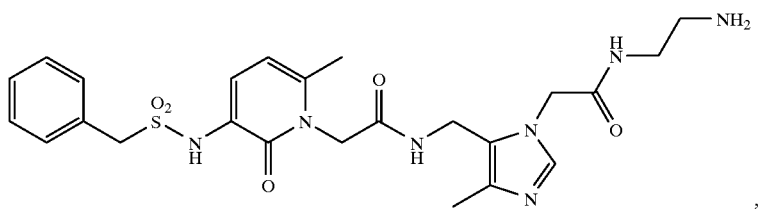,
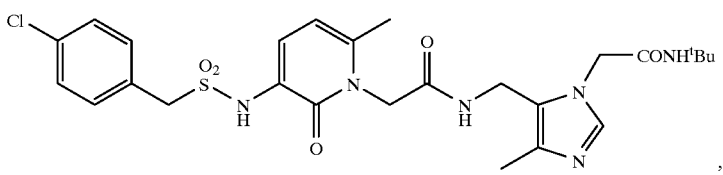,
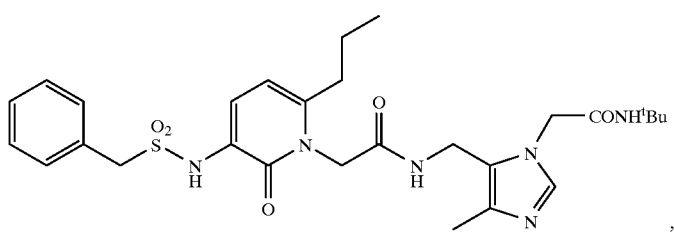,
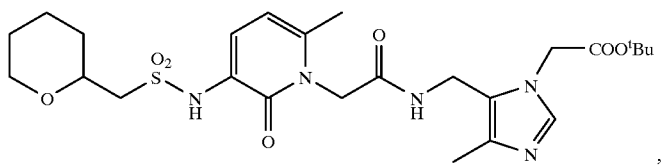,
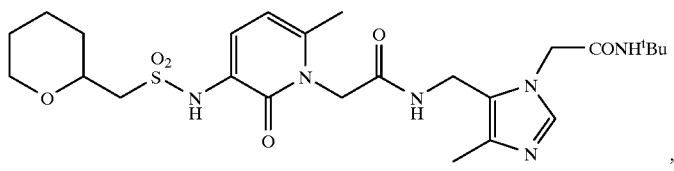,

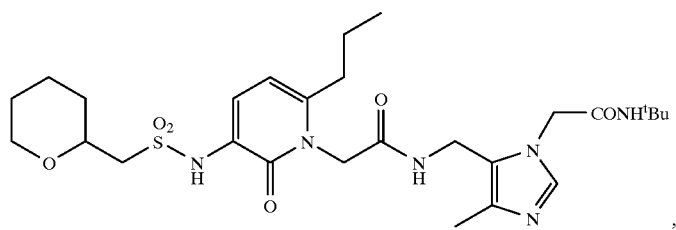,
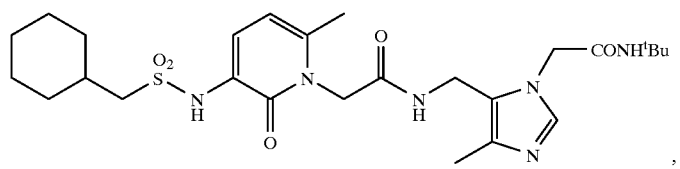,
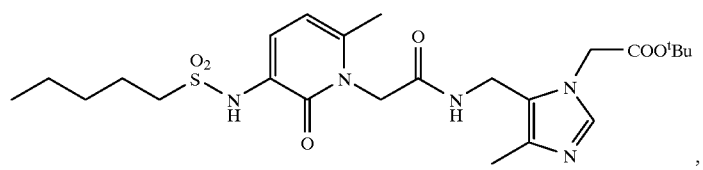,
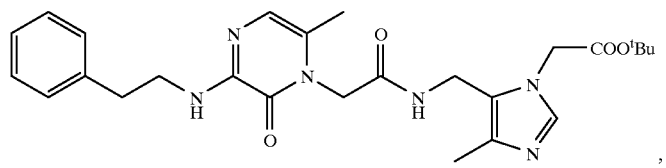,
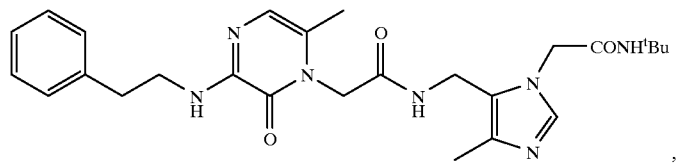,
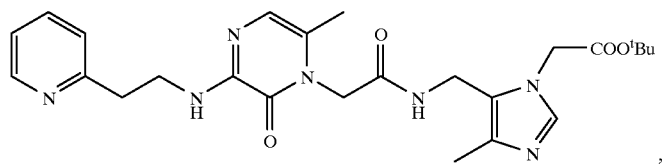,
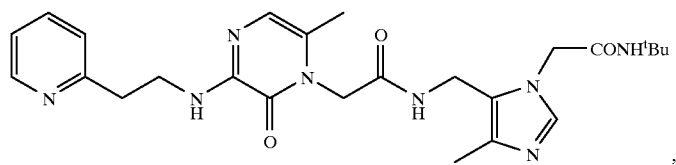,
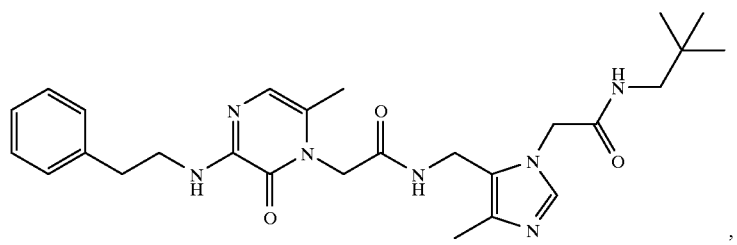,

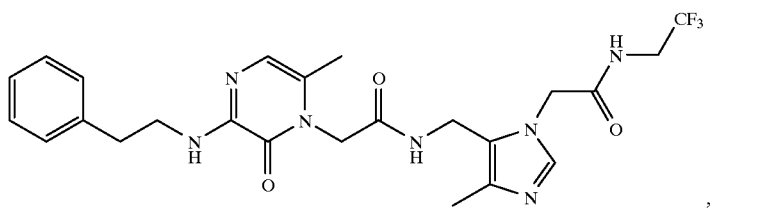
,
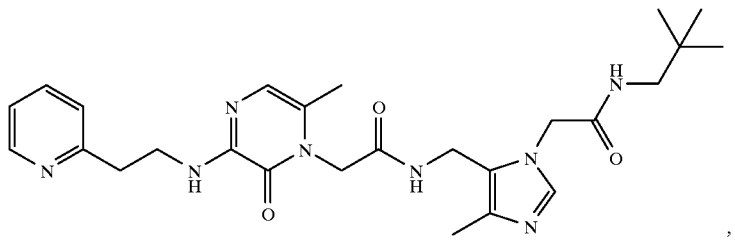
,
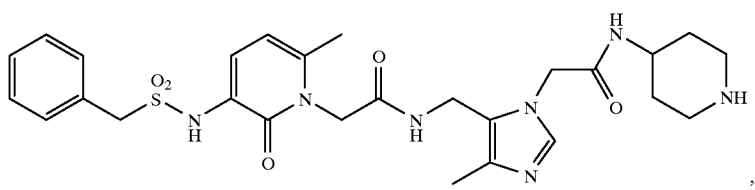
,
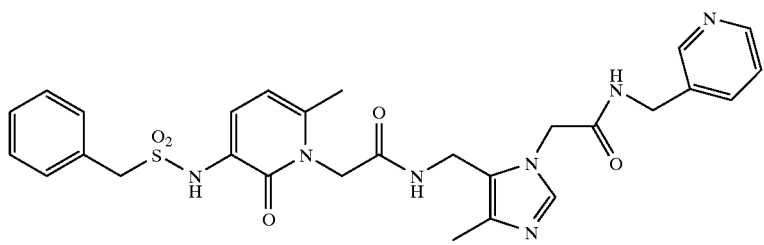
,
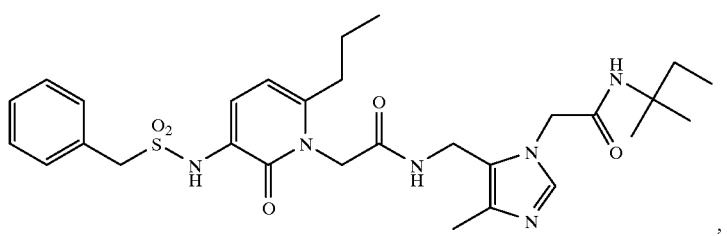
,
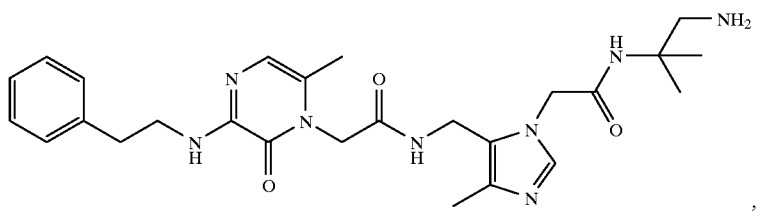
,
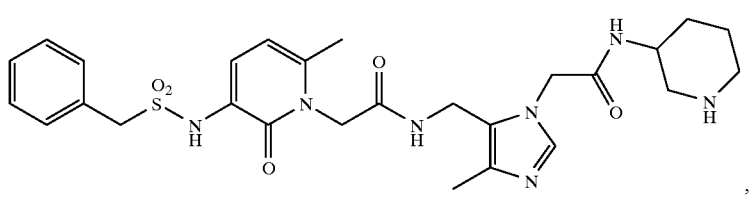
,

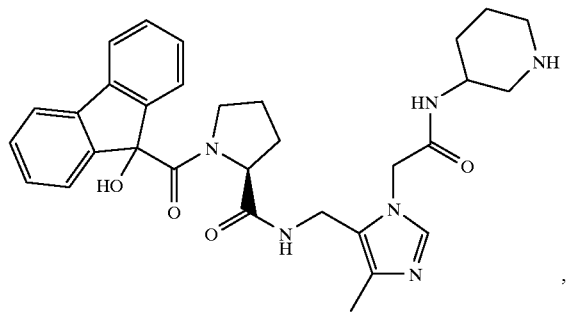
,
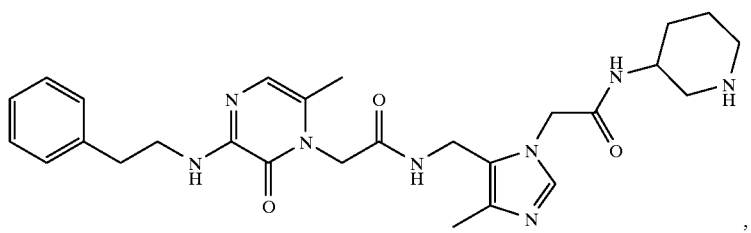
,
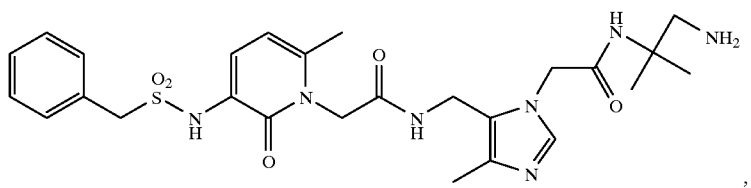
,
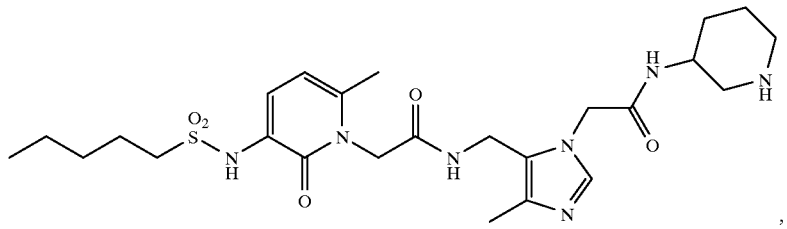
,
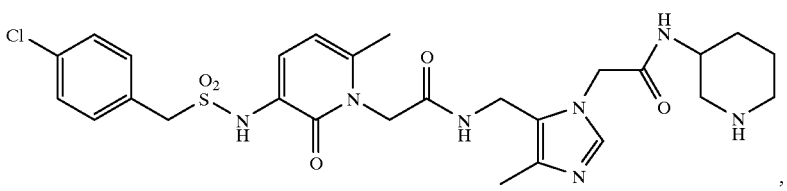
,
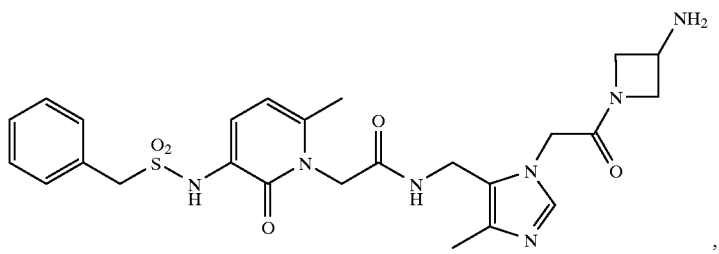
,

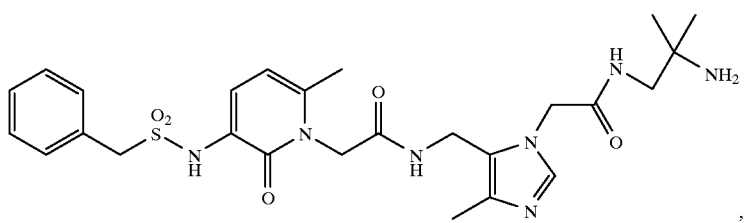
,
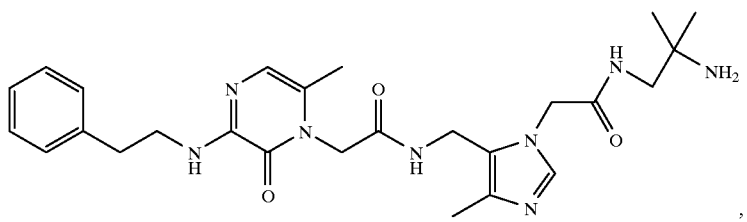
,
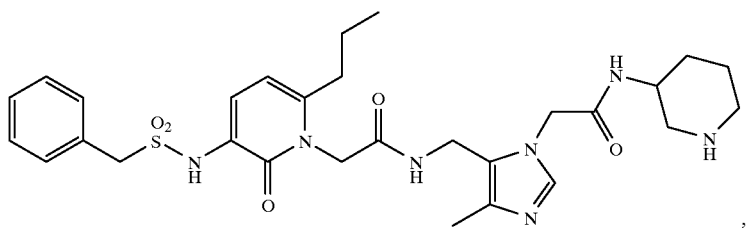
,
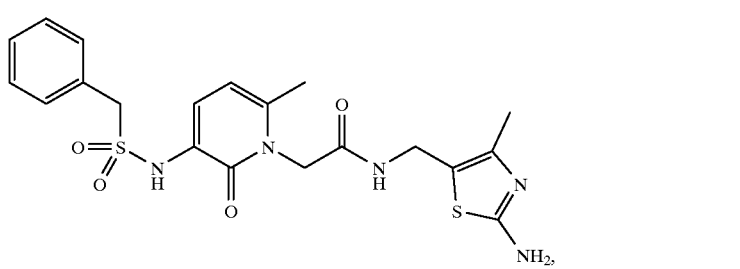
,
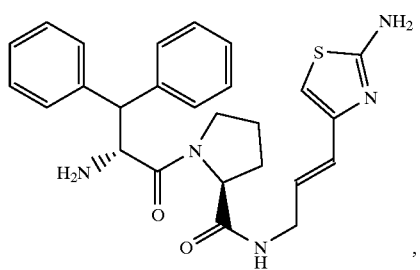
,
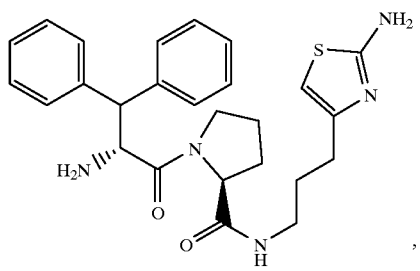
,

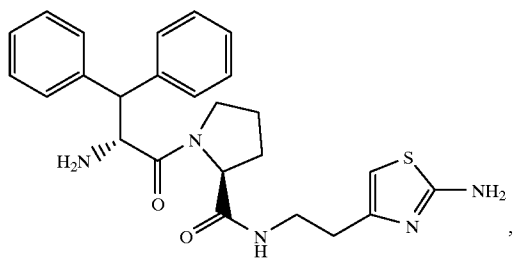,
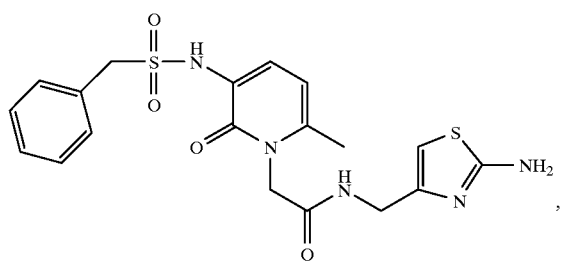,
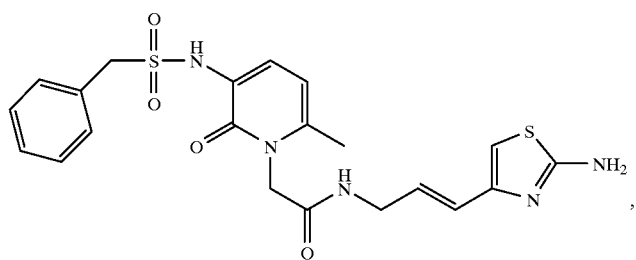,
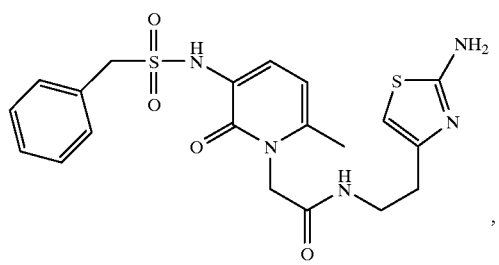,
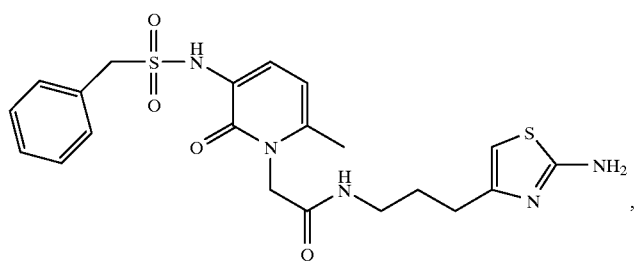,
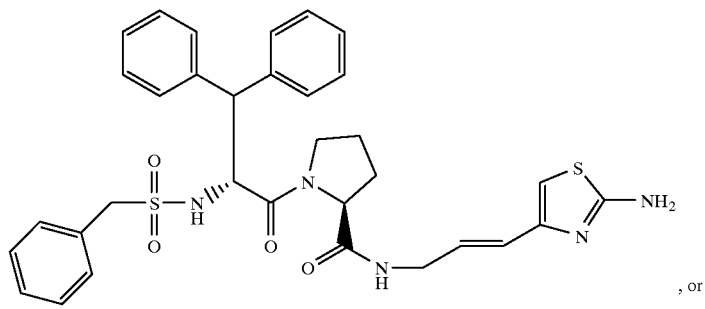, or

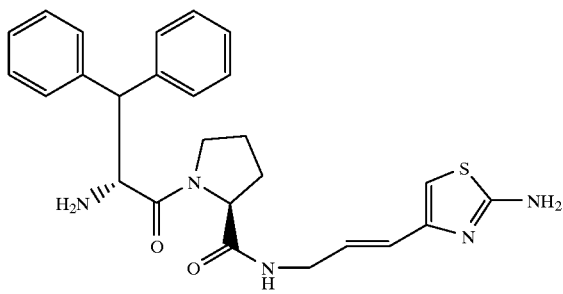

and pharmaceutically acceptable salts thereof.

Compounds of the present invention, which are thrombin inhibitors, are useful in anticoagulant therapy. Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems The compounds of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinlypyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

For example, oral tablets can be prepared which contain an amount of active compound of between 100 and 500 mg, e.g. 100, 200, 300, 400 or 500 mg. Typically, a patient in need of thrombin inhibitor compound, depending on weight and metabolism of the patient, would be administered between about 100 and 1000 mg active compound per day. For a patient requiring 1000 mg per day, two tablets containing 250 mg of active compound can be administered in the morning and two tablets containing 250 mg of active compound can again be administered in the evening. For a patient requiring 500 mg per day, one tablet containing 250 mg of active compound can be administered in the morning and one tablet containing 250 mg of active compound can again be administered in the evening.

The compounds are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds can also be co-administered with suitable anti-coagulation agents or thrombolytic agents such as plasminogen activators or streptokinase to achieve synergistic effects in the treatment of various ascular pathologies. For example, the compounds enhance the efficiency of tissue plasminogen activator-mediated thrombolytic reperfusion. The compounds may be administered first following thrombus formation, and tissue plasminogen activator or other plasminogen activator is administered thereafter. They may also be combined with heparin, aspirin, or warfarin.

Specific embodiments of compounds of the invention inhibit thrombin with a Ki range of less than 1.0 nM according to in vitro measurements.

In Vitro Assay for Determining Proteinase Inhibition

Assays of human a-thrombin and human trypsin were performed at 25° C. in 0.05 M TRIS buffer pH 7.4, 0.15 M NaCl, 0.1% PEG. Trypsin assays also contained 1 mM $CaCl_2$.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human a-thrombin ($K_m$=125 $\mu$M) and human trypsin ($K_m$=59 $\mu$M). p-Nitroanilide substrate concentration was determined from measurements of absorbance at 342 nm using an extinction coefficient of 8270 $cm^{-1}M^{-1}$.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) ($K_m$=27 $\mu$M) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration $\leq$0.5 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Some abbreviations that may appear in this application are as follows.

| Designation | |
| --- | --- |
| BOC (Boc) | t-butyloxycarbonyl |
| HBT(HOBT or HOBt) | 1-hydroxybenzotriazole hydrate |
| BBC reagent | benzotriazolyloxy-bis(pyrrolidino)-carbonium hexafluorophosphate |
| PyClU | 1,1,3,3-bis(tetramethylene)-chlorouronium hexafluorophosphate |
| EDC | 1-ethyl-3-(3-dimethylaminopropyl) carbodiimide hydrochloride |
| $(BOC)_2O$ | di-t-butyl dicarbonate |
| DMF | dimethylformamide |
| $Et_3N$ or TEA | triethylamine |
| EtOAc | ethyl acetate |
| TFA | trifluoroacetic acid |
| DMAP | dimethylaminopyridine |
| DME | dimethoxyethane |
| $BH_3$-THF | Borane-tetrahydrofuran complex |
| D-Phe(3,4-$Cl_2$) | D-3,4-Dichlorophenylalanine |
| D-3,3-dicha | D-3,3-Dicyclohexylalanine |
| Pro | Proline |
| Arg | Arginine |
| Gly | Glycine |
| D-3,3,-diphe | D-3,3-Diphenylalanine |
| LAH | lithium aluminum hydroxide |
| Cy | cyclohexyl |
| $POCl_3$ | phosphorous oxychloride |
| MeCN | acetonitrile |
| $BnEt_3N+Cl-$ | benzyl triethyl ammonium chloride |
| NaH | sodium hydride |
| DMF | dimethylformamide |
| $BrCH_2COO^tBu$ | tert butyl bromoacetate |
| EtOH | ethyl alcohol |
| Pd(C) | palladium on activated carbon catalyst |
| $CF_3COOH$ | trifluoroacetic acid |
| DCM | dichloromethane |
| DIPEA | diisopropylethylamine |

The compounds of the present invention may have chiral centers and occur as racemates, racemic mixtures and as individual diastereomers, or enantiomers with all isomeric forms being included in the present invention.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like. The term "alkenyl" means straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like. The term "alkynyl" means straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like. Cycloalkyl means a cyclic, saturated ring containing 3 to 8 carbon atoms, e.g., cyclopropyl, cyclohexyl, etc. Halogen means chloro, bromo, fluoro or iodo. The term "aryl" means a 5- or 6-membered aromatic ring containing 0, 1, or 2 heteroatoms selected from O, N, and S, e.g. phenyl, pyridine, pyrimidine, imidazole, thiophene, oxazole, isoxazole, thiazole, and amino- and halogen- substituted derivatives thereof.

The pharmaceutically-acceptable salts of the compounds of the invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal: salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

SCHEME 1

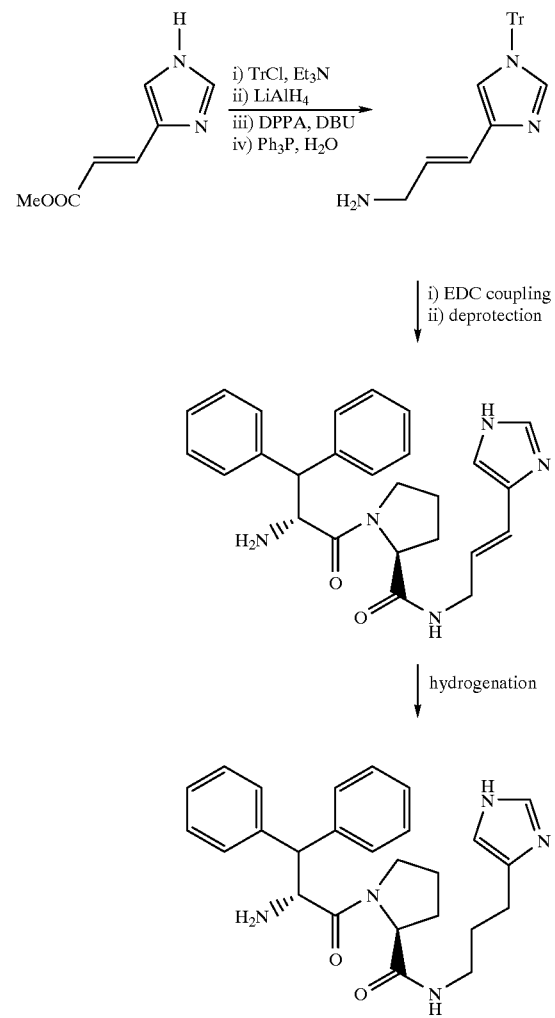

Scheme 1 shows a general procedure for preparing compounds of the invention where B is a three carbon alkane or alkene moiety. In Scheme 1, imidazole-4-acrylic acid methyl ester is protected as its trityl derivative by treatment with trityl chloride in the presence of triethylamine. Reduction of the ester with lithium aluminum hydride affords the corresponding alcohol which is then converted to an azide using DBU and diphenylphosphoryl azide. The allyl azide is then reduced to the corresponding allyl amine using the standard Staudinger reduction/hydrolysis protocol. The resulting amine is then coupled to A-COOH via routine EDC coupling techniques. Removal of the protecting groups under acidic conditions followed by hydrogenation of the double bond as necessary afforded compounds of the invention.

SCHEME 2

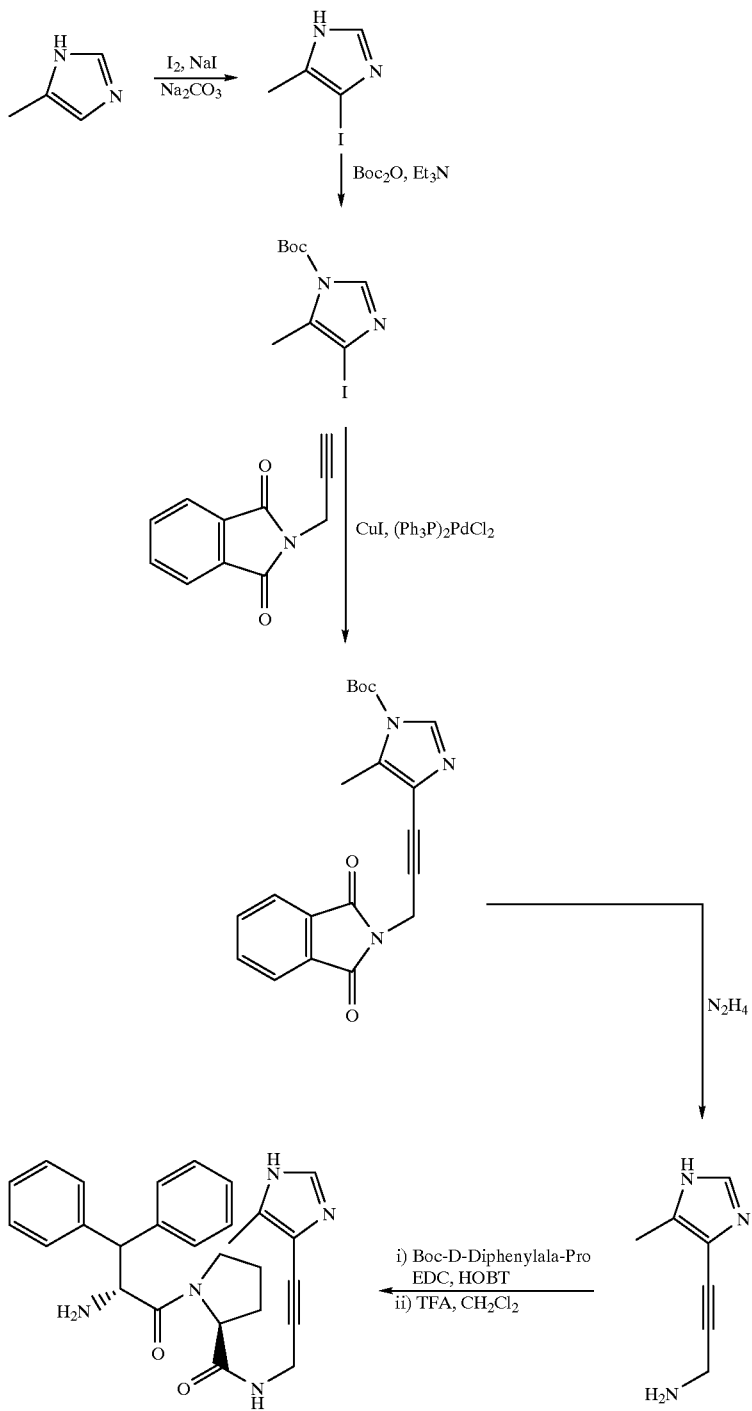

Scheme 2 shows a procedure for preparing compounds of the invention where B includes an alkyne. 4-Methylimidazole was iodinated under basic conditions and then protected as its Boc derivative. Following bis triphenylphosphinepalladium dichloride and copper iodide mediated coupling to N-propargylphthalimide the protecting groups were removed via treatment with hydrazine. The resulting imidazole propargylamine is coupled to A-COOH via a standard EDC coupling to form a compound of the invention.

SCHEME 3

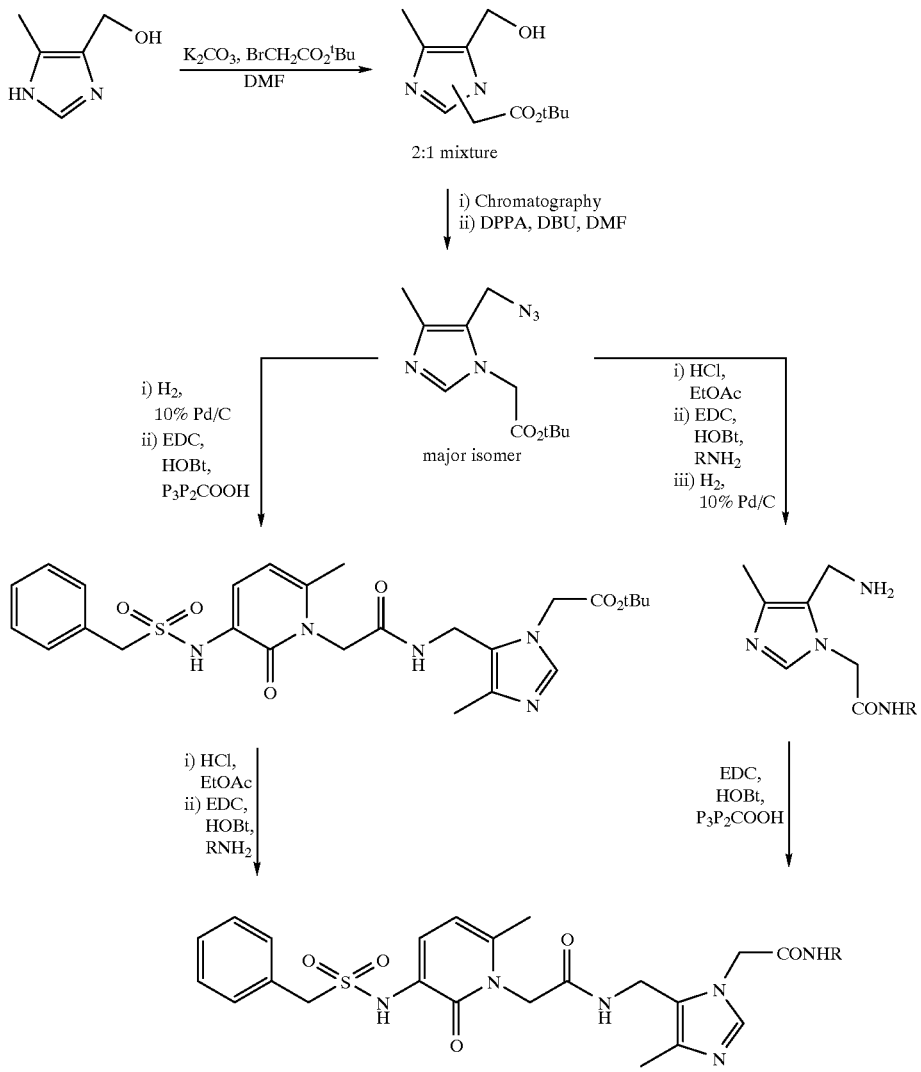

To form compounds of the invention with substituents X and Y at the 2- and 4-positions of the imidazole ring system, 4-methyl-5-imidazolemethanol is alkylated under basic conditions with an alkyl haloformate such as t-butylbromoacetate. Following chromatographic separation of the regioisomers, the major alcohol isomer is converted to the corresponding azide by treatment with diphenylphosphoryl azide and DBU.

Two different routes may be used to form a finished compound of the invention. In one, the azido functionality is first reduced in the presence of hydrogen and palladium on carbon and the resulting amine coupled to the A-COOH via standard EDC methodology. The t-butyl group is then removed under acidic conditions and the compound of the invention secured via EDC coupling to the requisite amine. Alternatively, the azidomethylimidazole t-butyl ester is first deprotected under acidic conditions and the resulting acid coupled to an amine using EDC. Reduction of the azide and EDC coupling to the A-COOH affords the compound of the invention.

Unless otherwise stated, all NMR determinations were made using 400 MHz field strength.

EXAMPLE I

Preparation of Boc-D-3,3-diphenylalanine-L-proline-N-(trans-4-imidazoleallyl) amide

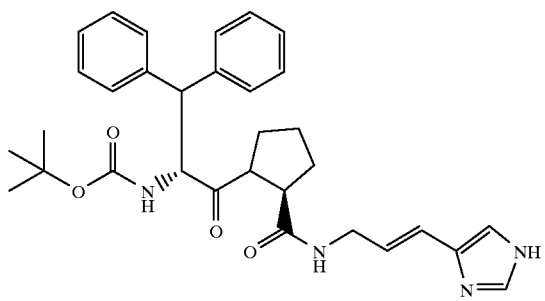

Step A: Boc-D-3,3-diphenylalanine-L-proline benzyl ester

To a solution of Boc-D-3,3-diphenylalanine (5.0 g, 14.6 mmol), L-proline benzyl ester (3.30 g 16.0 mmol) and HOBT (2.56 g 19.0 mmol) in DMF (150 ml) was added EDC (3.62 g, 19.0 mmol) and triethylamine (8.16 ml, 58 mmol). After stirring at room temperature overnight, the solvent was removed in vacuo and the resulting residue partitioned between chloroform and 1M citric acid. The aqueous layer was extracted with chloroform and the combined organics were washed with water, 10% $Na_2CO_3$ solution and dried over $MgSO_4$. The solution was then filtered and the solvent removed in vacuo to give the title compound: $^1$H NMR ($CDCl_3$) d 1.20–1.90 (m, 4 H), 1.30 (s, 9 H), 2.80 (q, J=6 Hz, 1 H), 3.70–3.80 (m, 1 H), 4.10–4.18 (m, 1 H), 4.35 (d, J=11.5 Hz, 1 H) 5.03–5.28 (m, 4 H), 7.10–7.40 (m, 15 H).

Step B: Boc-D-3,3-diphenylalanine-L-proline

A solution of Boc-D-3,3-diphenylalanine-L-proline benzyl ester (8.0 g, 15.0 mmol) in ethanol (200 ml) was hydrogenated in the presence of 10% Pd/C (2.0 g) a t atmospheric pressure for 24 h. The reaction mixture was then filtered through Celite and the filtrate concentrated in vacuo to give the title compound as a white solid: $^1$H NMR ($CDCl_3$) d 1.20–1.40 (m, 1 H), 1.35 (s, 9 H), 1.40–1.60 (m, 1 H), 1.70– 1.90 (m, 1 H), 2.21–2.30 (m, 1 H), 2.70 (q, J=9 Hz, 1 H), 3.75 (br t, J=9 Hz, 1 H), 4.16 (d, J=9 Hz, 1 H), 4.35 (d, J=11.5 Hz, 1 H), 4.97–5.18 (m, 2 H), 7.22–7.39 (m, 10 H).

Step C: Trans-4-imidazoleacrylic acid methyl ester hydrochloride

A solution of trans-4-imidazoleacrylic acid (20.0 g 145 mmol) in methanol (300 ml) was saturated with anhydrous HCl and the resulting solution was then refluxed for 90 min. After cooling to room temperature the solvent was removed in vacu to to give the title compound as a white solid: $^1$H NMR ($CD_3OD$) d 3.80 (s, 3 H), 6.61 (d, J=16 Hz, 1 H), 7.60 (d, J=16 Hz, 1 H), 7.92, (s, 1 H), 9.05, (s, 1 H).

Step D: Trans-1-trityl-4-imidazoleacrylic acid methyl ester

To a solution of trans-4-imidazoleacrylic acid methyl ester hydrochloride (20.0 g, 106 mmol) and triethylamine (44 ml, 318 mmol) in chloroform (500 ml) was added a solution of trityl chloride (29.5 g, 318 mmol) in chloroform (100 ml). The resulting suspension was stirred at room temperature for 24 h. The reaction mixture was then washed with water and dried over $MgSO_4$. Filtration and removal of the solvent in vacuo to gave the title compound as a tan solid: $^1$H NMR ($CDCl_3$) d 3.75 (s, 3 H), 6.54 (d, J=16 Hz, 1 H) 7.03 (s, 1 H), 7.13–7.34 (m, 15 H) 7.46 (s, 1 H), 7.51 (d, J=16 Hz 1 H).

Step E: Trans-1-trityl-4-imidazoleallyl alcohol

A 1M solution of LAH in ether (30 ml, 30 mmol) was added dropwise to a cooled (−45° C.) solution of trans-1-trityl-4-imidazoleacrylic acid methyl ester (23 g, 58.3 mmol) in THF (300 ml). After stirring at −45° C. for 3 h, additional 1M LAH solution (30 ml) was added. Stirring was continued at −45° C. for 1 h, then the solution was warmed to and stirred at 0° C. for 30 min. The reaction was quenched with ethyl acetate, then saturated $NH_4Cl$ and allowed to stir at room temperature overnight. The layers were separated and the aqueous layer was extracted twice with ethyl acetate. The combined organics were dried over $MgSO_4$, filtered and the solvents removed in vacuo. The crude product was purified by flash chromatography on silica gel (ethyl acetate elution) to give the title compound: $^1$H NMR (DMSO) d 4.03 (m, 2 H), 4.68 (t, J=5 Hz, 1 H) 6.20–6.40 (m, 2 H), 6.89 (s, 1 H) 7.00–7.50 (m, 16 H).

Step F: Trans-1-trityl-4-imidazoleallyl azide

DBU (5.4 ml 35.7 mmol) was added dropwise to a cooled (0° C.) solution of trans-1-trityl-4-imidazoleallyl alcohol (8.76 g, 23.8 mmol) and diphenylphosphoryl azide (7.7 ml, 35.7 mmol) in THF (300 ml). The reaction mixture was allowed to warm gradually to and then stirred at room temperature overnight. The solvent was then removed in vacuo and the resulting residue purified by flash chromatography on silica gel (2:1 hexane/ethyl acetate) to give the title compound: $^1$H NMR ($CDCl_3$) d 3.88 (d, J=6 Hz, 2 H), 6.25–6.50 (m, 2 H), 6.79 (s, 1 H), 7.14–7.34 (m, 15 H), 7.40 (s, 1 H).

Step G: Trans-1-trityl-4-imidazoleallylamine

A solution of trans-1-trityl-4-imidazoleallyl azide (6.4 g, 16.8 mmol) and triphenylphosphine (11.0 g, 42.0 mmol) in THF (100 ml) was heated to reflux for 2 h, after which water (1 ml) was added. The resulting solution was then heated at reflux for 24 h. After cooling to room temperature the solvent was removed in vacuo and the residue purified by flash chormatography on silica gel (19:1 chloroform/10% $NH_4OH$ in MeOH) to give the title compound as white solid: $^1$H NMR ($CDCl_3$) d 1.50 (br s, 2 H), 3.41 (d, J=5 Hz, 2 H), 6.30–6.48 (m, 2 H), 6.73 (s, 1H), 7.13–7.38 (m, 15 H), 7.40 (s, 1 H).

Step H: Trans-4-imidazoleallylamine dihydrochloride

A solution of trans-1-trityl-4-imidazoleallylamine (1.0 g, 2.7 mmol) in 1N HCl (50 ml) was heated to reflux for 30 min, cooled to room temperature and filtered. The filter cake was washed with water. Concentration of the filtrate in vacuo gave the title compound: $^1$H NMR (DMSO) d 3.80 (br s, 2 H), 6.50–6.72 (m, 2 H), 7.81 (s, 1 H), 8.50 (br s, 3 H), 9.15 (s, 1 H).

Step I: Boc-D-3,3-diphenylalanine-L-proline-N-(trans-4-imidazolealyl) amide

Boc-D-3,3-diphenylalanine-L-proline and trans-4-imidazoleallylamine dihydrochloride were coupled using essentially the same procedure described in EXAMPLE I, Step A except that no citric acid wash was preformed. The final compound was purified by preparative HPLC. $^1$H NMR ($CH_3OD$) d 1.23 (s, 9 H), 1.40–1.65 (m, 2 H), 1.70–1.90 (m, 2 H), 2.90 (q, J=6 Hz, 1 H), 3.75–3.85 (br m, 1 H), 3.90 (d, J=6 Hz, 2 H), 4.10 (d, J=8 Hz, 1 H) 4.38 (d, J=11 Hz, 1 H) 5.10 (d, J=11 Hz, 1 H), 6.00–6.10 (br m, 1 H), 6.41 (d, J=16 Hz, 1 H), 7.01 (s, 1 H) 7.20–7.45 (m, 10 H), 7.60 (s, 1 H); MS (FAB) 544 $(M+1)^+$.

EXAMPLE II

Preparation of D-3,3-Diphenylalanine-L-proline-N-(trans-4-imidazole allyl) amide

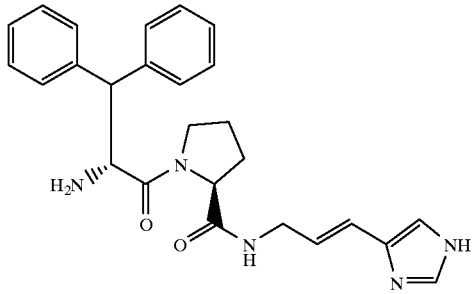

A solution of Boc-D-3,3-diphenylalanine-L-proline-N-(trans-4-imidazoleallyl) amide (55 mg, 0.1 mmol) in 2:1 methylene chloride/TFA (30 ml) was stirred at room temperature for 4 h. The solvents were removed in vacuo and the residue was purified by preparative HPLC. $^1$H NMR ($CH_3OD$) d 1.10–1.37 (m, 2 H), 1.70–1.90 (br s, 2 H), 2.70–2.90 (br m, 1 H), 3.50–3.65 (br m, 1 H) 3.95 (br s, 2

H), 4.00–4.10 (br m, 1 H), 4.45 (d, J=11.5 Hz, 1 H), 4.95 (d, J=11.5 Hz, 1 H) 6.30–6.40 (m, 1 H), 6.58 (d, J=16 Hz, 1 H), 7.25–7.70 (m, 11 H), 7.85 (s, 1 H); MS (FAB) 444 (M+1)⁺.

EXAMPLE III

Preparation of D-3,3-Diphenylalanine-L-proline-N-(4-imidazolepropyl) amide

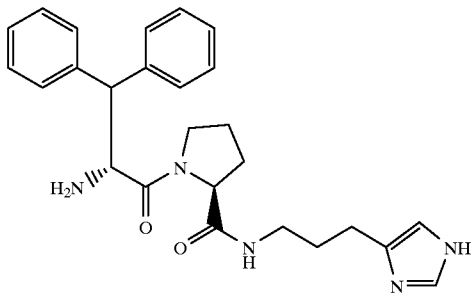

Step A: Boc-D-3,3-diphenylalanine-L-proline-N-(4-imidazole propyl)amide

A solution of Boc-D-3,3-diphenylalanine-L-proline-N-(trans-4-imidazoleallyl) amide (200 mg, 0.36 mmol) in ethanol (100 ml) containing 10% Pd/C (100 mg) was hydrogenated at 45 psi for 24 h. The solution was subsequently filtered through Celite and the solvent removed in vacuo to give the title compound as a solid: ¹H NMR (CD₃OD) d 1.28–1.65 (m, 3 H), 1.30 (s, 9 H), 1.70–1.87 (m, 3 H), 2.55 (t, J=8 Hz, 2 H), 2.88 (q, J=8 Hz, 1 H), 3.05–3.30 (m, 2 H), 3.70–3.80 (m, 1 H), 3.95–4.05 (m, 1 H), 4.35 (d, J=11.5 Hz, 1 H), 5.10 (d, J=11.5 Hz, 1H), 6.80 (s, 1 H), 7.19–7.42 (m, 10 H), 7.60 (s, 1 H).

Step B: D-3,3-Diphenylalanine-L-proline-N-(4-imidazolepropyl) amide

The title compound was prepared from Boc-D-3,3-diphenylalanine-L-proline-N-(4-imidazolepropyl) amide using the procedure of EXAMPLE II: ¹H NMR (CD₃OD) d 1.22–1.35 (m, 2 H), 1.70–1.95 (m, 4 H), 2.75–2.88 (m, 1 H), 2.78 (t, J=8 Hz, 2 H), 3.12–3.33 (m, 2 H), 3.50–3.60 (m, 1 H), 4.00 (t, J=7 Hz, 1 H), 4.42 (d, J=12 Hz, 1 H), 4.99 (d, J=12 Hz, 1 H), 7.25–7.62 (m, 11 H), 8.80 (s, 1 H); MS (FAB) 446 (M+1)⁺.

EXAMPLE IV

Preparation of N-Benzylsulfonyl-D-3,3-diphenylalanine-L-proline-N-(trans4-imidazoleallyl) amide

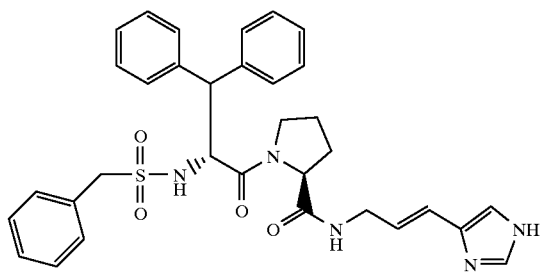

Step A: D-3,3-Diphenylalanine-L-proline benzyl ester

The title compound was prepared from Boc-D-3,3-diphenylalanine-L-proline benzyl ester using the procedure described for EXAMPLE II: ¹H NMR (CDCl₃) d 1.35–1.48 (m, 1 H), 1.70–1.83 (m, 3 H), 2.70–2.82 (m, 1 H), 3.50–3.60 (m, 1 H), 4.15–4.25 (m, 3 H), 5.15 (ab q, J=32 and 12 Hz, 2 H), 7.12–7.40 (m, 15 H).

Step B: N-Benzylsulfonyl-D-3,3-diphenylalanine-L-proline benzyl ester

A solution of benzylsulfonyl chloride (177 mg, 0.934 mmol) in methylene chloride (10 ml) was added dropwise to a solution of D-3,3-diphenylalanine-L-proline benzyl ester (200 mg, 0.47 mmol) in methylene chloride at –78° C. After stirring at –78° C. for 45 min, triethylamine (0.13 ml, 0.93 mmol) was added and the reaction mixture was allowed to stir at –78° C. for an additional 30 min. It was then warmed to room temperature for 24 h. The reaction mixture was washed with water, dried over MgSO₄, filtered and the solvent removed in vacuo. The residue was purified by flash chromatography on silica gel (7:3 hexane/ethyl acetate). ¹H NMR (CDCl₃) d 1.40–1.55 (m, 1 H), 1.55–1.77 (m, 1 H), 1.77–1.90 (m, 2 H), 2.70–2.80 (m, 1 H), 3.72–3.83 (m, 1 H), 4.10 (d, J=11 Hz, 1 H), 4.15–4.25 (m, 1 H), 4.33 (d, J=11 Hz, 1 H), 4.65 (d, J=6 Hz 1 H), 5.10 (ab q, J=56 and 14 Hz, 2 H), 5.10–5.19 (m, 1 H), 7.20–7.41 (m, 20 H).

Step C: N-Benzylsulfonyl-D-3,3-diphenylalanine-L-proline

The title compound was prepared from N-benzylsulfonyl-D-3,3-diphenylalanine-L-proline benzyl ester using the procedure described in EXAMPLE I, Step B: 1H NMR (CDCl₃) d 1.30–1.53 (m, 2 H), 1.70–1.87 (m, 1 H), 2.07–2.17 (m, 1 H), 2.68 (q, J=9 Hz, 1 H), 3.52–3.65 (m, 1 H), 3.95–4.15 (m, 3 H), 4.30 (d, J=12 Hz, 1 H), 4.80–4.95 (m, 1 H), 5.00–5.12 (m, 1 H), 7.10–7.45 (m, 15 H).

Step D: N-Benzylsulfonyl-D-3,3-diphenylalanine-L-proline-N-(trans-1-trityl-4-imidazoleallyl)amide The title compound was prepared from N-benzylsulfonyl-D-3,3-diphenylalanine-L-proline and trans-1-trityl-4-imidazoleallylamine using the procedure described in EXAMPLE 1, Step A: ¹H NMR (CDCl₃) d 1.30–1.85 (m, 4 H), 2.02–2.15 (m, 1 H), 2.55–2.70 (m, 1 H), 3.60–4.27 (m, 5 H), 4.33 (d, J=12 Hz, 1 H), 4.80–4.90 (m, 1 H), 4.95 (d, J=12 Hz, 1 H), 6.15–6.37 (m, 2 H), 6.70 (s, 1 H), 6.85 (t, J=8 Hz, 1 H), 7.05–7.40 (m, 31 H).

Step E: N-Benzylsulfonyl-D-3,3-diphenylalanine-L-proline-N-(trans-4-imidazoleallyl)amide N-Benzylsulfonyl-D-3,3-diphenylalanine-L-proline-N-(trans-1-trityl-4-imidazoleallyl) amide (180 mg, 0.2 mmol) was dissolved in 2:1 methylene chloride/TFA (75 ml). Triethylsilane was then added dropwise until the bright yellow color had disappeared. The reaction was allowed to stir at room temperature overnight. The solvents were removed in vacuo and the residue was purified by preparative HPLC. ¹H NMR (CD₃OD) d 1.40–1.50 (m, 1 H), 1.50–1.70 (m, 1 H), 1.70–1.90 (m, 2 H), 2.90–3.02 (m, 1 H), 3.72–3.83 (m, 2 H), 3.95–4.08 (m, 2 H), 4.21 (ab q, J=16 and 2.7 Hz, 2 H), 4.34 (d, J=11.5 Hz, 1 H), 5.06 (d, J=11.5 Hz, 1 H), 6.22 (d of t, J=16 and 6 Hz, 1 H), 6.50 (d, J=16 Hz, 1 H), 7.10–7.60 (m, 16 H), 8.77 (s, 1 H); MS (FAB) 598 (M+1)⁺.

EXAMPLE V

Preparation of N-Benzylsulfonyl-D-3,3-diphenylalanine-L-proline-N-(4-imidazolepropyl) amide

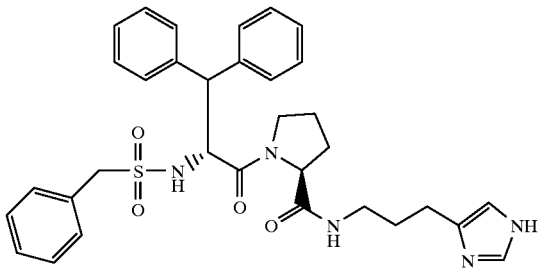

A solution of N-Benzylsulfonyl-D-3,3-diphenylalanine-L-proline-N-(trans-4-imidazoleallyl) amide (55 mg, 0.092 mmol) in ethanol (50 ml) was hydrogenated at 40 psi in the presence of 10% Pd/C (50 mg) for 4 h. The solution was filtered through Celite and the solvent removed in vacuo. The product was purified by preparative HPLC. $^1$H NMR (CD$_3$OD) d 1.40–1.90 (m, 6 H), 2.70 (t, J=6 Hz, 2 H), 2.92–3.18 (m, 2 H), 3.20–3.30 (m, 1 H), 3.72–3.82 (br m, 1 H), 3.90–4.00 (m, 1 H), 4.20–4.38 (m, 3 H), 5.05 (d, J=11.5 Hz, 1H), 7.10–7.60 (m, 16 H), 8.60 (s, 1 H); MS (FAB) 600 (M+1)$^+$.

EXAMPLE VI

Preparation of N-Methoxycarbonylmethanesulfonyl-D-3,3-diphenyl alanine-L-proline-N-(trans-4-imidazoleallyl)amide

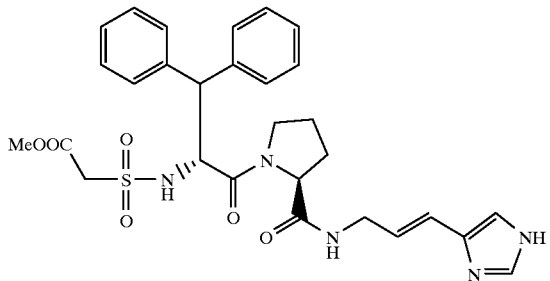

Step A: N-Methoxycarbonylmethanesulfonyl-D-3,3-diphenyl alanine-L-proline benzyl ester To a solution of D-3,3-diphenylalanine-L-proline benzyl ester (200 mg, 0.47 mmol) in methylene chloride (20 ml) at −78° C. was added dropwise a solution of chlorosulfonylacetic acid methyl ester (100 mg, 0.56 mmol) in methylene chloride (5 ml). The reaction was stirred at −78° C. for 10 min and then triethylamine (0.13 ml, 0.93 mmol) was added. Stirring at −78° C. was continued for an additional 5 min followed by warming to room temperature for 15 min. The reaction was quenched with water, dried over MgSO$_4$, filtered and the solvent removed in vacuo. The residue was purified by flash chromatography on silica gel (3:2 hexane/ethyl acetate). $^1$H NMR (CDCl$_3$) d 1.30–1.50 (m, 1 H), 1.60–1.82 (m, 3 H), 2.60–2.70 (m, 1 H), 3.60–3.70 (m, 1 H), 3.73 (s, 3 H), 4.00 (ab q, J=108 and 16 Hz) 4.15–4.20 (m, 1 H), 4.35 (d, J=12 Hz, 1 H), 5.00–5.20 (m, 3 H), 5.66 (d, J=12 Hz, 1 H), 7.10–7.42 (m, 15 H).

Step B: N-Methoxycarbonylmethanesulfonyl-D-3,3-diphenyl alanine-L-proline

The title compound was prepared from N-methoxycarbonylmethanesulfonyl-D-3,3-diphenylalanine-L-proline benzyl ester using the procedure described in EXAMPLE I, Step B. $^1$H NMR (CDCl$_3$) d 1.45–1.55 (m, 2 H), 1.72–1.82 (m, 1 H), 2.02–2.10 (m, 1 H), 2.62–2.75 (m, 1 H), 3.68–3.72 (m, 1 H), 3.75 (s, 3 H), 3.92 (ab q, J=75 and 14 Hz, 2 H), 4.10–4.18 (m, 1 H), 4.35 (d, J=12 Hz, 1 H), 5.07 (t, J=12 Hz, 1 H), 5.80 (d, J=12 Hz, 1 H), 7.20–7.42 (m, 10 H).

Step C: N-Methoxycarbonylmethanesulfonyl-D-3,3-diphenyl alanine-L-proline-N-(trans-1-trityl-4-imidazoleallyl)amide The title compound was prepared from N-methoxycarbonylmethanesulfonyl-D-3,3-diphenylalanine-L-proline and trans-1-trityl-4-imidazoleallylamine essentially using the procedure described in EXAMPLE I, Step A. $^1$H NMR (CDCl$_3$) d 1.40–1.90 (m, 3 H), 1.95–2.10 (m, 1 H), 2.58–2.70 (q, J=8 Hz, 1 H), 3.57–3.62 (m, 1 H), 3.65 (s, 3 H), 3.75–4.05 (m, 2 H), 3.98 (ab q, J=65 and 15 Hz, 2 H), 4.10–4.18 (m, 1 H), 4.35 (d, J=12 Hz, 1 H), 5.02 (d, J=12 Hz, 1 H), 6.15–6.40 (m, 2 H), 6.65 (t, J=6 Hz, 1 H), 6.75 (s, 1 H), 7.10–7.45 (m, 26 H).

Step D: N-Methoxycarbonylmethanesulfonyl-D-3,3-diphenylalanine-L-proline-N-(trans-4-imidazoleallyl)amide The title compound was prepared from N-methoxycarbonylmethanesulfonyl-D-3,3-diphenylalanine-L-proline-N-(trans-1-trityl-4-imidazoleallyl) amide using the procedure described in EXAMPLE IV, Step E. $^1$H NMR (CD$_3$OD) d 1.30–1.50 (m, 1 H), 1.50–1.70 (m, 1 H), 1.70–1.90 (m, 2 H), 2.82–2.95 (m, 1 H), 3.64 (s, 3 H), 3.62–3.78 (m, 1 H), 3.80–3.95 (m, 1 H), 3.95–4.19 (m, 4 H), 4.35 (d, 11.5 Hz, 1 H), 5.13 (d, J=11.5 Hz, 1 30 H), 6.30 (d of t, J=16 and 6 Hz, 1 H), 6.54 (d, J=16 Hz, 1 H), 7.20–7.58 (m, 11 H), 7.81 (t, J=6 Hz, 1 H), 8.83 (s, 1 H); MS (FAB) 580 (M+1)+.

EXAMPLE VII

Preparation of N-Methoxycarbonylmethanesulfonyl-D-3,3-diphenyl alanine-L-proline-N-(4-imidazolepropyl)amide

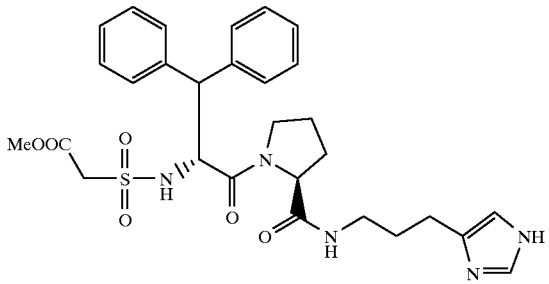

The title compound was prepared from N-methoxycarbonylmethanesulfonyl-D-3,3-diphenylalanine-L-proline-N-(trans-4-imidazoleallyl) amide using the procedure of EXAMPLE III, Step A. The final product was purified by preparative HPLC. $^1$H NMR (CD$_3$OD) d 1.36–1.45 (m, 1 H), 1.55–1.70 (m, 1 H), 1.70–1.90 (m, 4 H), 2.70–2.80 (m, 2 H), 2.85–2.98 (m, 1 H), 3.10–3.20 (m, 1 H), 3.21–3.30 (m, 1 H), 3.68 (s, 3 H), 3.70–3.80 (m, 1 H), 3.92–3.99 (m, 1 H), 4.16 (s, 2 H), 4.34 (d, J=11.5 Hz, 1 H), 5.13 (d, J=11.5 Hz, 1 H), 7.22–7.55 (m, 11 H), 8.76 (s, 1 H); MS (FAB) 582 (M+1)$^+$.

EXAMPLE VIII

Preparation of N-[(1R)-10-Camphorsulfonyl]-D-3,3-diphenylalanine-L-proline-N-(trans-4-imidazoleallyl) amide

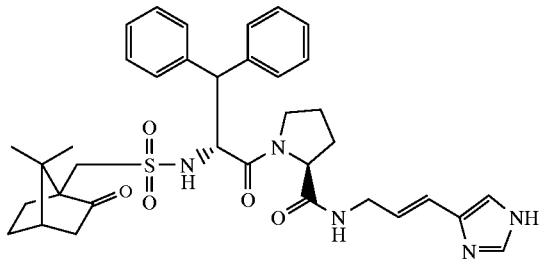

Step A: N-[(1R)-10-Camphorsulfonyl]-D-3,3-diphenylalanine-L-proline benzyl ester The title compound was prepared from D-3,3-diphenylalanine-L-proline benzyl ester and (1R)-(−)-10-camphorsulfonyl chloride using the procedure described in EXAMPLE IV, Step B: $^1$H NMR (CDCl$_3$) d 0.90 (s, 3 H), 0.95 (s, 3 H), 1.32–1.42 (m, 2 H), 1.70–1.78 (m, 2 H), 1.85 (d, J=16 Hz, 1 H), 1.90–2.08 (m, 4 H), 2.35–2.48 (m, 1 H), 2.70 (q, J=6 Hz, 1 H), 2.97 (d, J=16 Hz, 1 H), 3.41 (d, J=16 Hz, 1 H), 3.72–3.82 (m, 1 H), 4.10–4.17 (m, 1 H), 4.35 (d, J=12 Hz, 1 H), 5.00–5.18 (m, 3 H), 6.57 (d, J=12 Hz, 1 H), 7.10–7.45 (m, 15 H).

Step B: N-[(1R)-10-Camphorsulfonyl]-D-3,3-diphenylalanine-L-proline

The title compound was prepared from N-[(1R)-10-camphorsulfonyl]-D-3,3-diphenylalanine-L-proline benzyl ester using the procedure described in EXAMPLE I, Step B. $^1$H NMR (CDCl$_3$) d 0.87 (s, 3 H), 0.93 (s, 3 H), 1.22–2.20 (m, 9 H), 2.35–2.45 (m, 1 H), 2.70 (q, J=6 Hz, 1 H), 2.87 (d, J=16 Hz, 1 H), 3.25 (d, J=16 Hz, 1 H), 3.70–3.80 (m, 1 H), 4.05 (d, J=10 Hz, 1 H), 4.37 (d, J=12 Hz, 1 H), 5.08 (t, J=12 Hz, 1 H), 6.50 (d, J=12 Hz, 1 H) 7.17–7.42 (m, 10 H).

Step C: N-[(1R)-10-Camphorsulfonyl]-D-3,3-diphenylalanine-L-proline-N-(trans-1-trityl-4-imidazoleallyl) amide The title compound was prepared from N-[(1R)-10-camphorsulfonyl]-D-3,3-diphenylalanine-L-proline and trans-1-trityl-4-imidazoleallylamine using the procedure described in EXAMPLE I, Step A. $^1$H NMR (CDCl$_3$) d 0.80 (s, 3 H), 0.88 (s, 3 H), 1.22–2.09 (m, 11 H), 2.28–2.40 (m, 1 H), 2.65 (q, J=9 Hz, 1 H), 2.75 (d, J=16 Hz, 1 H), 3.50 (d, J=16 Hz, 1 H), 3.62–3.78 (m, 1 H), 3.85–3.95 (m, 2 H), 4.22 (d, J=9 Hz, 1 H), 4.35 (d, J=12 Hz, 1 H), 4.98 (t, J=12 Hz, 1 H), 6.15–6.40 (m, 2 H), 6.75 (s, 1 H), 6.85 (t, J=6 Hz, 1 H), 7.10–7.47 (m, 26 H).

Step D: N-[(1R)-10-Camphorsulfonyl]-D-3,3-diphenylalanine-L-proline-N-(trans-4-imidazoleallyl) amide The title compound was prepared from N-[(1R)-10-camphorsulfonyl]-D-3,3-diphenylalanine-L-proline-N-(trans-1-trityl-4-imidazoleallyl) amide using the procedure described in EXAMPLE IV, Step E. $^1$H NMR (CD$_3$OD) d 0.80 (s, 3 H), 0.95 (s, 3 H), 1.30–2.10 (m, 11 H), 2.25–2.37 (m, 1 H), 2.85 (d, J=15 Hz, 1 H), 2.98 (q, J=7 Hz, 1 H), 3.35 (d, J=15 Hz, 1 H), 3.75–3.90 (m, 2 H), 3.97–4.10 (m, 2 H), 4.32 (d, J=11.5 Hz, 1 H), 5.09 (d, J=11.5 Hz, 1 H), 6.28 (d of t, J=16 and 6 Hz, 1 H), 6.53 (d, J=16 Hz, 1 H), 7.20–7.60 (m, 11 H), 8.83 (s, 1 H); MS (FAB) 658 (M+1)$^+$.

EXAMPLE IX

Preparation of N-[(1S)-10-Camphorsulfonyl]-D-3,3-diphenylalanine-L-proline-N-(trans-4-imidazoleallyl) amide

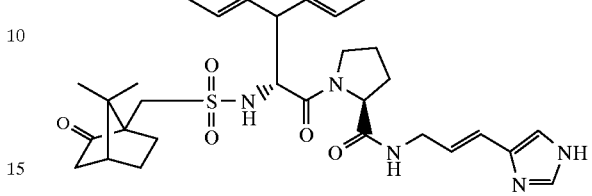

The title compound was prepared from D-3,3-diphenylalanine-L-proline benzyl ester and (1S)-(+)-10-camphorsulfonyl chloride using the procedure described for EXAMPLE VIII: $^1$H NMR (CD$_3$OD) d 0.83 (s, 3 H), 0.96 (s, 3 H), 1.25–2.40 (m, 11 H), 2.91 (d, J=15 Hz, 1 H), 3.00 (q, J=7 Hz, 1 H), 3.35 (d, J=15 Hz, 1 H) 3.75–3.90 (m, 2 H), 4.00–4.10 (m, 2 H), 4.33 (d, J=11.5 Hz, 1 H), 5.05 (d, J=11.5 Hz, 1 H), 6.30 (d of t, J=16 and 6 Hz, 1 H), 6.51 (d, J=16 Hz, 1 H) 7.20–7.60 (m, 11 H) 7.60–7.70 (m, 1 H), 8.83 (s, 1 H); MS (FAB) 658 (M+1)$^+$.

EXAMPLE X

Preparation of D-3,3-Diphenylalanine-L-homoproline-N-(trans-4-imidazoleallyl) amide

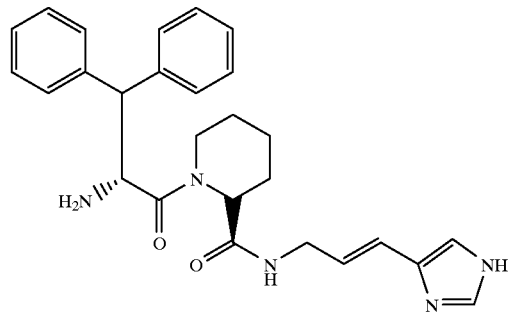

Step A: Boc-L-homoproline benzyl ester

DBU (2.2 ml, 15 mmol) was added to a solution of Boc-L-homoproline (3 g, 13 mmol) in acetonitrile (30 ml). After stirring for 10 min, benzyl bromide (1.7 ml, 14 mol) was added and stirring was continued for 3 h. The solvent was then rotovapped off and the residue partitioned between ethyl acetate and water. The organic phase was washed with 1 M citric acid, water then 10% aqueous Na$_2$CO$_3$ and dried (Na$_2$SO$_4$). Concentration gave the title compound as a yellow oil (4 g). $^1$H NMR (CDCl$_3$) d 1.19–1.68 (m, 15 H), 2.24 (br m, 1 H), 2.90–2.97 (br m, 1 H), 3.91–4.02 (br m, 1 H), 5.20 (br m, 2 H), 7.35 (m, 5 H).

Step B: L-Homoproline benzyl ester hydrochloride

Anhydrous HCl was bubbled through a cooled (0° C.) solution of Boc-L-homoproline benzyl ester (3 g) in ethyl acetate (100 ml) for 10 min. The resulting mixture was allowed to warm gradually to room temperature over 4 h. The solution was then purged with argon and rotavapped down. Trituration of the residue with ether gave the title compound as a white solid (2.4 g). $^1$H NMR (CD$_3$OD) d 1.55–1.92 (m, 6 H), 2.30 (br m, 1 H), 3.20 (br m, 1 H), 3.42 (br m, 1 H), 4.08 (br m, 1 H), 5.29 (br m, 2 H), 7.36–7.40 (m, 5 H).

Step C: Boc-D-3,3-diphenylalanine-L-homoproline benzyl ester

The title compound was prepared from Boc-D-3,3-diphenylalanine and L-homoproline benzyl ester hydrochloride essentially according to the procedure described for EXAMPLE I, Step A. $^1$H NMR (CDCl$_3$) d 1.09–1.58 (m, 15 H), 2.05 (m, 1 H), 3.13 (br m, 1 H), 3.88 (br m, 1 H), 4.42 (br m, 1 H), 5.06 (br m, 1 H), 5.16 (m, 2 H), 5.55 (m, 1 H), 7.11–7.40 (m, 15 H).

Step D: Boc-D-3,3-diphenylalanine-L-homoproline

A solution of Boc-D-3,3-diphenylalanine-L-homoproline benzyl ester (4.2 g, 7.8 mmol) in ethyl acetate (50 ml) was hydrogenated at 1 atm in the presence of 10% Pd/C (1 g) for 4 h. Removal of the catalyst by filtration through Celite and concentration of the filtrate in vacuo gave the title compound as a white solid (3.5 g). $^1$H NMR (CDCl$_3$) d 1.17–1.38 (m, 15 H), 2.15 (m, 1 H), 3.09 (m, 1 H), 3.84 (m, 1 H), 4.41 (m, 1 H), 5.15 (m, 1 H), 5.37 (m, 1 H), 7.17–7.40 (m, 10 H).

Step E: Boc-D-3,3-diphenylalanine-L-homoproline-N-(trans-1-trityl-4-imidazoleallyl) amide Boc-D-3,3-diphenylalanine-L-homoproline was coupled to trans-1-trityl-4-imidazoleallylamine essentially according to the procedure described for EXAMPLE I, Step A. $^1$H NMR (CDCl$_3$) d 1.20–1.34 (m, 15 H), 2.30 (m, 1 H), 3.02 (m, 1 H), 3.73 (m, 1 H), 3.85 (m, 1 H), 4.10 (m, 1 H), 4.38 (m, 1 H), 4.92 (m, 1 H), 5.19 (m, 2 H), 6.23–6.34 (m, 2 H), 6.70 (s, 1 H), 7.13–7.37 (m, 26 H).

Step F: D-3,3-diphenylalanine-L-homoproline-N-(trans-4-imidazole-allyl) amide

Simultaneous removal of the protecting groups from Boc-D-3,3-diphenylalanine-L-homoproline-N-(trans-1-trityl-4-imidazoleallyl) amide was accomplished essentially according to the procedure described in EXAMPLE IV, Step E affording the title compound which was purified by preparative HPLC. $^1$H NMR (CD$_3$OD) d 0.24 (m, 1 H), 1.12–1.36 (m, 4 H), 2.03 (br d, J=13.6 Hz, 1 H), 3.22 (m, 1 H), 3.74 (br d, J=11.7 Hz, 1 H), 4.01 (m, 2 H), 4.44 (d, J=11.3 Hz, 1 H), 4.95 (br s, 1 H), 5.34 (d, J=11.3 Hz, 1 H), 6.35 (dt, J=5.2, 16.2 Hz, 1 H), 6.47 (d, J=16.2 Hz, 1 H), 7.25–7.64 (m, 11 H), 8.85 (d, J=1.3 Hz, 1 H); MS (FAB) 458 (M+1)$^+$.

EXAMPLE XI

Preparation of D-3,3-Bis-(4'-methoxyphenyl)amine-L-proline-N-(trans-4-imidazoleallyl) amide

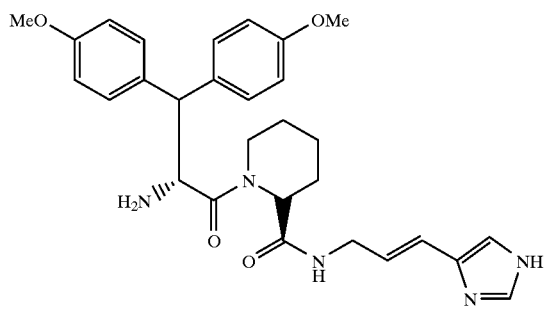

Step A: Bis-(4-methoxyphenyl)methanol

To a stirred solution of 4,4'-dimethoxybenzophenone (5.0 g, 20.6 mmol) in 1:1 THF/ethanol (100 ml) was added sodium borohydride (946 mg, 25 mmol) and the mixture stirred overnight at ambient temperature. Additional borohydride (200 mg) was added, and the mixture heated to 40° C. for 1 h, cooled and quenched with acetone. The mixture was rotavapped to dryness, partitioned between EtOAc and cold 1M citric acid, the organic layer washed with 10% Na$_2$CO$_3$, brine, treated with activated carbon and concentrated to give the title compound as a colorless solid.

Step B: 3,3-Bis-(4'-methoxyphenyl)-2-nitropropionic acid ethyl ester

To a stirred (0° C.) solution of bis-(4-methoxyphenyl) methanol (2.5 g, 10.2 mmol) and ethyl nitroacetate (2.26 ml, 20.4 mmol) in CH$_2$Cl$_2$ (50 ml) under argon was added AlCl$_3$ (1.36 g, 10.2 mmol) in one portion. After 1 h, the reaction mixture was allowed to warm to approximately 10° C. and poured into a mixture of ice and 2M HCl. The resulting mixture was stirred for 45 min, and the aqueous layer extracted with CH$_2$Cl$_2$. The combined organic layers were washed with 10% Na$_2$CO$_3$, dried over MgSO$_4$, treated with activated carbon, and concentrated to give a reddish oil that was chromatographed (CHCl$_3$ elution) to afford the title compound as a colorless oil.

Step C: Boc-DL-3,3-bis-(4'-methoxyphenyl)alanine ethyl ester

Amalgamated zinc was prepared by treating zinc dust (11.4 g) with 2M HCl (83 ml) for 5 min and then decanting the supernatant. To this was then added a solution of 3,3-bis-(4'-methoxyphenyl)-2-nitropropionic acid ethyl ester (3.0 g, 8.3 mmol) in 1:1 THF/CH$_3$OH (166 ml), followed by the addition of 2M HCl (43 ml). This mixture was heated at reflux under argon for 2 h, cooled to approximately 40° C., filtered through a glass-fiber filter and concentrated by rotavap. The resulting residue was diluted with brine, basified with 2M NaOH and extracted with 3 portions of CH$_2$Cl$_2$. The combined organic layers were dried over Na$_2$SO$_4$ and concentrated to give a colorless oil (2.62 g) that was dissolved in dioxane (50 ml) containing di-t-butyldicarbonate (2 g, 9.1 mmol). To this stirred solution under argon was added 1M NaOH (9 ml) and stirred overnight at room temperature. The reaction mixture was concentrated and the residue partitioned between EtOAc and 1M citric acid. The organic layer was washed with 10% Na$_2$CO$_3$, brine, dried over MgSO$_4$ and concentrated to give a yellow oil that was chromatographed (1:4 to 2:3 ethyl acetate/hexanes) to provide the title compound as a colorless foam.

Step D: Boc-DL-3,3-bis-(4'-methoxyphenyl)alanine

To a stirred solution of Boc-DL-3,3-bis-(4'-methoxyphenyl)alanine ethyl ester (2.32 g, 5.4 mmol) in dimethoxyethane (50 ml) was added 1M LiOH (8.1 ml) and the mixture stirred overnight under argon. Additional 1M LiOH (4 ml) was added, and stirring continued for 48 h. The reaction mixture was concentrated by rotavap, the residue partitioned between 1M citric acid and EtOAc, and the aqueous layer extracted with EtOAc. The combined organic layers were washed with water, brine, dried over Na$_2$SO$_4$ and concentrated by rotavap to give the title compound as a colorless foam.

Step E: Boc-DL-3,3-bis-(4'-methoxyphenyl)alanine-L-proline benzyl ester

The title compound was prepared from Boc-DL-3,3-bis-(4'-methoxyphenyl)alanine and L-proline benzyl ester essentially according to the procedure described for EXAMPLE I, Step A.

57

Step F: Boc-DL-3,3-bis-(4'-methoxyphenyl)alanine-L-proline

The title compound was prepared from Boc-DL-3,3-bis-(4'-methoxyphenyl)alanine-L-proline benzyl ester essentially according to the procedure described for EXAMPLE I, Step B.

Step G: Boc-DL-3,3-bis-(4'-methoxyphenyl)alanine-L-proline-N-(trans-1-trityl-4-imidazoleallyl) amide The title compound was prepared from Boc-DL-3,3-bis-(4'-methoxyphenyl)alanine-L-proline and trans-1-trityl-4-imidazoleallylamine using the procedure described in EXAMPLE I, Step A.

Step H: D-3,3-Bis-(4'-methoxyphenyl)alanine-L-proline-N-(trans-4-imidazoleallyl) amide The title compound was prepared from Boc-DL-3,3-bis-(4'-methoxyphenyl)alanine-L-proline-N-(trans-1-trityl-4-imidazoleallyl) amide using the procedure described in EXAMPLE IV, Step E. The diastereomers were separated by preparative HPLC. The title compound is the less polar diastereomer. $^1$H NMR (CD$_3$OD) d 1.30–1.42 (m, 1 H), 1.82 (br s, 3 H), 2.72–2.88 (m, 1 H), 3.50–3.63 (m, 1 H), 3.75 (s, 3 H), 3.81 (s, 3 H), 4.00 (br s, 2 H), 4.05–4.17 (m, 1 H), 4.34 (d, J=11.2 Hz, 1 H), 6.35 (d oft, J=16 and 6 Hz, 1H), 6.58 (d J=16 Hz, 1 H), 6.85 (d, J=8.5 Hz, 2 H), 7.03 (d, J=8 Hz, 2 H), 7.20 (d J=8.5 Hz, 2 H), 7.48 (d, J=8.3 Hz, 2 H), 7.53 (s, 1 H), 8.86 (s, 1 H); MS (FAB) 504 M+1)$^+$.

EXAMPLE XII

Preparation of D-3,3-Bis-(4'-methoxyphenyl)alanine-L-proline-N-(4-imidazolepropyl) amide

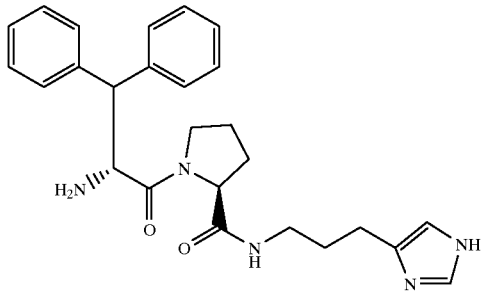

The title compound was prepared from D-3,3-bis-(4'-methoxyphenyl)alanine-L-proline-N-(trans-4-imidazoleallyl) amide using the procedure described in EXAMPLE I, Step B. $^1$H NMR (CD$_3$OD) d 1.10–1.40 (br m, 2 H), 1.70–1.95 (br m, 4 H), 2.70–2.85 (br m, 3 H), 2.90–3.10 (br m, 2 H), 3.45–3.60 (br m, 1 H), 3.70 (br s, 3 H), 3.80 (br s, 3 H), 3.95–4.08 (br m, 1 H), 4.25–4.40 (br m, 1 H), 6.75–6.85 (br m, 2 H), 6.90–7.05 (br m, 2 H), 7.10–7.22 (br m, 2 H), 7.30–7.37 (br m, 1 H), 7.42–7.53 (br m, 2 H), 8.75 (br s, 1 H); MS (FAB) 506 (M+1)$^+$.

58

EXAMPLE XIII

Preparation of D-3,3-Diphenylalanine-L-proline-N-(trans-5-methyl-4-imidazoleallyl) amide

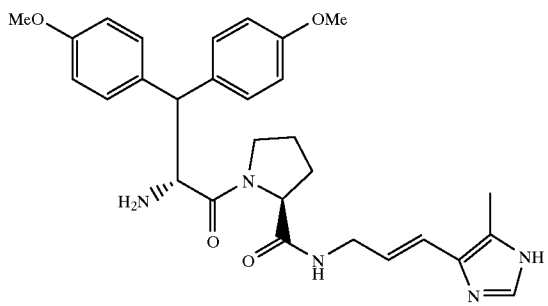

Step A: 1- and 3-Trityl-4-methyl-5-imidazolecarboxaldehyde

Trityl chloride (28 g, 100 mmol) was added to a cooled (0° C.) solution of 4-methyl-5-imidazolecarboxaldehyde (10 g, 91 mmol) and triethylamine (16 ml, 115 mmol) in methylene chloride (300 ml). After stirring for 30 min, the reaction mixture was warmed to room temperature and stirred there for 2 h. The reaction mixture was then washed well with water and saturated NaHCO$_3$. Drying over Na$_2$SO$_4$ and removal of the solvent in vacuo gave a 1:1 mixture of the title compounds as a white powder. 1-trityl isomer $^1$H NMR (CDCl$_3$) d 2.55 (s, 3 H), 7.12–7.38 (m, 15 H), 9.11 (s, 1 H); 3-trityl isomer $^1$H NMR (CDCl$_3$) d 1.83 (s, 3 H), 7.10–7.42 (m, 15 H), 10.02 (s, 1 H).

Step B: Trans-1-trityl-4-methyl-5-imidazoleacrylic acid methyl ester

A mixture of 1- and 3-trityl-4-methyl-5-imidazolecarboxaldehyde (7 g, 20 mmol) and methyl (triphenylphosphoranylidene)acetate (6.7 g, 20 mmol) in toluene (40 ml) was heated at reflux for 24 h. After cooling to room temperature, silica gel was added and the solvent removed in vacuo. The residue was transferred to a flash column and eluted with 3:2 hexane/ethyl acetate to give the title compound. $^1$H NMR (CDCl$_3$) d 1.58 (s, 3 H), 3.77 (s, 3 H), 6.59 (d, J=15.3 Hz, 1 H), 7.13–7.16 (m, 6 H), 7.33–7.36 (m, 10 H), 7.57 (dd, J=0.4, 15.3 Hz, 1 H).

Step C: Trans-1-trityl-4-methyl-5-imidazoleallyl alcohol A 1M solution of DIBAL in methylene chloride (20 ml, 20 mmol) was added to a cooled (–78° C.) solution of the ester (2.5 g, 6.1 mmol) in THF (30 ml). After stirring at –78° C. for 30 min, the reaction mixture was stored at –25° C. for 19 h. The reaction mixture was then warmed to 0° C. and carefully quenched sequentially with methanol (1.4 ml) and 1M sodium hydroxide (2.8 ml). After stirring for 10 min, 30% sodium potassium tartrate (7 ml) was added. The reaction mixture was then stirred until precipitation was complete. The precipitate was filtered off and washed well with ether and ethyl acetate. The filtrate was washed with brine and dried over Na$_2$SO$_4$. Filtration and concentration afforded the title compound as a crystalline foam. $^1$H NMR (CDCl$_3$) d 1.49 (s, 3 H), 4.30 (d, J=5.1 Hz, 2 H), 6.46–6.57 (m, 2 H), 7.13–7.17 (m, 6 H), 7.29 (s, 1 H), 7.31–7.37 (m, 9 H).

Step D: Trans-1-trityl-4-methyl-5-imidazoleallyl azide

Trans-1-trityl-4-methyl-5-imidazoleallyl alcohol was converted to the corresponding azide essentially according to the procedure described for EXAMPLE I, Step F. $^1$H NMR (CDCl$_3$) d 1.50 (s, 3 H), 3.93 (d, J=6.2 Hz, 2 H), 6.40–6.51 (m, 2 H), 7.13–7.18 (m, 6 H), 7.29 (s, 1 H), 7.32–7.35 (m, 9 H).

Step E: Trans-1-trityl-4-methyl-5-imidazoleallylamine

Trans-1-trityl-4-methyl-5-imidazoleallyl azide was converted to the corresponding amine essentially according to the procedure described for EXAMPLE I, Step G. $^1$H NMR (CDCl$_3$) d 1.48 (s, 3 H), 1.82 (br s, 2 H), 3.46 (d, J=6.0 Hz, 2 H), 6.36 (d, J=15.4 Hz, 1 H), 6.47 (m, 1 H), 7.12–7.18 (m, 6 H), 7.27 (s, 1 H), 7.31–7.37 (m, 9 H).

Step F: D-3,3-Diphenylalanine-L-proline-N-(trans-5-methyl-4-imidazoleallyl) amide Boc-D-3,3-diphenylalanine-L-proline was coupled to trans-1-trityl-4-methyl-5-imidazoleallylamine essentially according to the procedure described for EXAMPLE I, Step A then the protecting groups were simultaneously removed essentially according to the procedure of EXAMPLE IV, Step E. $^1$H NMR (CD$_3$OD) d 1.18 (m, 1 H), 1.79 (m, 3 H), 2.42 (s, 3 H), 2.84 (m, 1 H), 3.58 (m, 1 H), 3.96–4.11 (m, 3 H), 4.45 (d, J=11.4 Hz, 1 H), 4.99 (d, J=11.4 Hz, 1 H), 6.25 (dt, J=5.1, 16.3 Hz, 1 H), 6.55 (d, J=16.3 Hz, 1 H), 7.27–7.60 (m, 10 H), 8.76 (s, 1 H); MS (FAB) 458 (M+1)$^+$.

EXAMPLE XIV

Preparation of D-3,3-Diphenylalanine-L-proline-N-(5-methyl-4-imidazolepropyl) amide

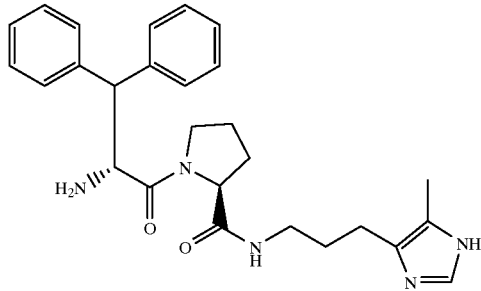

A solution of D-3,3-diphenylalanine-L-proline-N-(trans-5-methyl-4-imidazoleallyl) amide (280 mg) in ethanol (10 ml) containing 5% Pd/C was stirred at room temperature under an atmosphere of hydrogen overnight. The catalyst was removed by filtration through Celite. The filtrate was concentrated and the residue purified by preparative HPLC to give the title compound. $^1$H NMR (CD$_3$OD) d 1.30 (m, 1 H), 1.73–1.87 (m, 5 H), 2.30 (s, 3 H), 2.71 (m, 2 H), 2.82 (m, 1 H), 3.22 (m, 2 H), 3.56 (m, 1 H), 4.01 (m, 1 H), 4.44 (d, J=11.5 Hz, 1 H), 4.98 (d, J=11.5 Hz, 1 H), 7.27–7.62 (m, 10 H), 8.67 (s, 1 H); MS (FAB) 460 (M+1)$^+$.

EXAMPLE XV

Preparation of D-3,3-Diphenylalanine-L-proline-N-(4-imidazoleproparpyl) amide

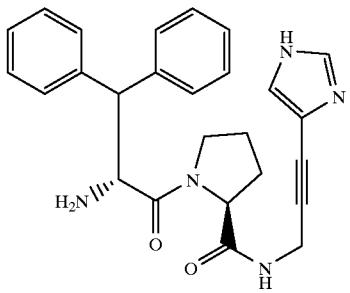

Step A: N-Propargylphthalimide

A mixture of propargylamine (7 ml, 102 mmol) and phthalic anhydride (15 g, 101 mmol) in chloroform (200 ml) was heated together at 70° C. overnight. Filtration gave a 1:1 mixture of the phthalimide and the acid-amide (20 g). This was suspended in THF (100 ml) and heated at 70° C. until complete dissolution had been effected. Powdered 4A sieves (15 g) was added and the heating continued for 24 h. The reaction mixture was cooled and filtered through Celite washing the residue well with methanol. The filtrate was concentrated, redissolved in chloroform and then adsorbed onto silica gel and chromatographed (8:1:1 to 7:1.5:1.5 hexane/chloroform/ethyl acetate) to give the title compound as a white solid. $^1$H NMR (CDCl$_3$) d 2.23 (m, 1 H), 4.47 (m, 2 H), 7.75 (m, 2 H), 7.88 (m, 2 H).

Step B: 4,5-Diodoimidazole

A solution of iodine (49.5 g, 195 mmol) and sodium iodide (53.5 g, 360 mmol) in water (350 ml) was added dropwise over 3 h to a solution of imidazole (6.8 g, 100 mmol) and sodium carbonate (23 g, 220 mmol) in water (650 ml). After an additional 3 h, the diiodide was filtered off and washed well with water. Drying yielded a cream colored solid which was recrystallized from aqueous acetone with the aid of decolorizing carbon. $^1$H NMR (CD$_3$OD) d 7.75 (s, 1 H).

Step C: 4-Iodoimidazole

A hot saturated solution of the diodide (12 g) in ethanol (60 ml) was mixed together with a solution of sodium thiosulfate (29 g) in water (10 ml). A white precipitate separated. The resulting mixture was heated at 100° C. for 24 h. then cooled and filtered. The filtrate was evaporated and the residue boiled three times with chloroform (400 ml portions) each time followed by a hot filtration. Concentration of the filtrate gave 4-iodoimidazole as a white solid. $^1$H NMR (CD$_3$OD) d 7.20 (s, 1 H), 7.63 (s, 1 H).

Step D: 1-Trityl-4-iodoimidazole

Trityl chloride (3.8 g, 13.6 mmol) was added to a cooled (0° C.) solution of 4-iodoimidazole (2.25 g, 11.6 mmol) and triethylamine (2 ml, 14.3 mmol) in methylene chloride (25 ml). After stirring for 30 min the reaction mixture was warmed to room temperature and stirred ther for 2 h. The reaction mixture was washed well with water and saturated NaHCO$_3$ then dried (Na$_2$SO$_4$). Concentration gave the product as a white solid. $^1$H NMR (CDCl$_3$) d 6.92 (s, 1 H), 7.08–7.20 (m, 6 H), 7.28–7.40 (m, 10 H).

Step E: 1-Trityl-4-imidazolepropargyl phthalimide

A suspension of N-propargylphthalimide (450.9 mg, 2.4 mmol) and 1-trityl-4-iodoimidazole (875.5 mg, 2 mmol) in diethylamine (20 ml) was heated to 55° C. Dissolution was incomplete. Bis triphenylphosphinepalladium dichloride (15.6 mg) and copper (I) iodide (a smidgen) were added and heating continued overnight. The reaction mixture was cooled and the solvent rotavapped off. The residue was redissolved in methylene chloride and ether (twice the volume). It was washed with saturated NaHCO$_3$ and water then dried (1:1 Na$_2$SO$_4$/K$_2$CO$_3$). Concentration, adsorption onto silica gel and chromatography (5:4:1 ethyl acetate/hexane/chloroform) gave the title compound as a cream powder. $^1$H NMR (CDCl$_3$) d 4.65 (s, 2 H), 7.01 (s, 1 H), 7.10 (m, 6 H), 7.33 (m, 10 H), 7.72 (m, 2 H), 7.86 (m, 2 H).

Step F: 1-Trityl-4-imidazolepropargylamine

Hydrazine monohydrate (3 ml) was added to a suspension of the phthalimido compound (734.2 mg, 1.5 mmol) in ethanol (15 ml). The bulk of the starting material dissolved. The reaction mixture was heated at 80° C. for 2 h. It was then cooled and rotavapped down. After azeotroping with toluene the residue was adsorbed onto silica gel and purified by flash chromatography (19:1 to 9:1 chlorofrom/10% NH$_4$OH in methanol) to give the amine as a white solid. $^1$H NMR (CDCl$_3$) d 3.60 (s, 2 H), 6.98 (s, 1 H), 7.13 (m, 6 H), 7.35 (m, 9 H), 7.39 (s, 1 H).

Step G: D-3,3-Diphenylalanine-L-proline-N-(4-imidazolepropargyl) amide

D-3,3-Diphenylalanine-L-proline and 1-trityl-4-imidazolepropargylamine were coupled essentially according to the procedure for Example I, Step A then the protecting groups were removed essentially according to the procedure of Example IV, Step E. $^1$H NMR (CD$_3$OD) d 1.30–1.39 (m, 1 H), 1.77 (m, 3 H), 2.79 (m, 1 H), 3.56 (m, 1 H), 4.06 (m, 1 H), 4.25 (dd, J=17.9 Hz, 2 H), 4.44 (d, J=11.4 Hz, 1 H), 4.98 (d, J=11.4 Hz, 1 H), 7.27–7.70 (m, 11 H), 8.78 (s, 1 H); MS (FAB) 442 (M+1)$^+$.

EXAMPLE XVI

Preparation of N-Benzylsulfonyl-D-3,3-diphenylalanine-L-proline-N-(4-imidazolepropargyl) amide

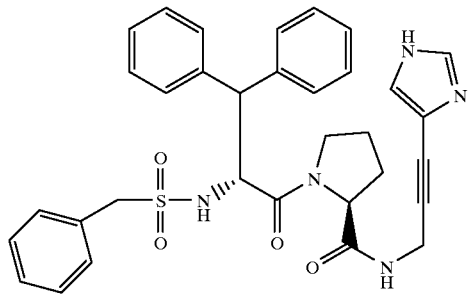

Step A: N-Benzylsulfonyl-D-3,3-diphenylalanine-L-proline-N-(1-trityl-4-imidazolepropargyl) amide The title compound was prepared from N-benzylsulfonyl-D-3,3-diphenylalanine-L-proline and 1-trityl-4-imidazolepropargylamine using the procedure described in EXAMPLE I, Step A.

Step B: N-Benzylsulfonyl-D-3,3-diphenylalanine-L-proline-N-(4-imidazolepropargl) amide The title compound was prepared from N-benzylsulfonyl-D-3,3-diphenylalanine-L-proline-N-(1-trityl-4-imidazolepropargyl) amide using the procedure described in EXAMPLE IV, Step E. $^1$H NMR (CD$_3$OD) d 1.40–1.50 (m, 1 H), 1.50–1.68 (m, 1 H), 1.72–1.90 (m, 2 H), 2.95–3.05 (m, 1 H), 3.72–3.82 (m, 1 H), 4.00–4.08 (m, 1 H), 4.10–4.18 (m, 2 H), 4.24 (d, J=2.7 Hz, 2 H), 4.33 (d, J=11.7 Hz, 1 H), 5.07 (d, J=11.2 Hz, 1 H), 7.15–7.58 (m, 16 H), 8.07 (m, 1 H), 8.72 (s, 1 H); MS (FAB) 596 (M+1)$^+$

EXAMPLE XVII

Preparation of D-3,3-diphenylalanine-L-homoproline-N-(4-imidazolepropargyl) amide

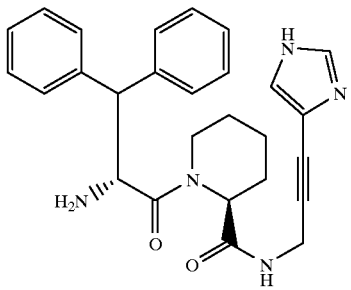

Step A: Boc-D-3,3-diphenylalanine-L-homoproline-N-(1-trityl-4-imidazolepropargyl) amide The title compound was prepared from Boc-D-3,3-diphenylalanine-L-homoproline and 1-trityl-4-imidazolepropargylamine using the procedure described in EXAMPLE I, Step A.

Step B: D-3,3-Diphenylalanine-L-homoproline-N-(4-imidazolepropargyl) amide

The title compound was prepared from Boc-D-3,3-diphenylalanine-L-homoproline-N-(1-trityl-4-imidazolepropargyl) amide using the procedure described in EXAMPLE IV, Step E. $^1$H NMR (CD$_3$OD) d 0.20 (m, 1 H), 0.80–1.40 (m, 4 H), 1.95–2.05 (m, 1 H), 3.18–3.30 (m, 1 H), 3.62–3.80 (m, 1 H), 4.25 (s, 2 H), 4.41 (d, J=11.5 Hz, 1 H), 5.34 (d, J=11.5 Hz, 1 H), 7.20–7.65 (m, 11 H), 8.46 (br s, 1 H); MS (FAB) 456 (M+1)$^+$

EXAMPLE XVIII

Preparation of D-3,3-Diphenylalanine-L-proline-N-(5-methyl-4-imidazole-propargyl) amide

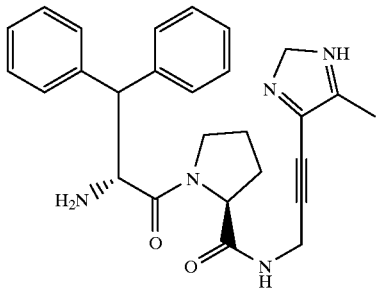

Step A: 4-Iodo-5-methylimidazole

To a solution of 4-methylimidazole (8.20 g, 100 mmol) and sodium carbonate (21.2 g, 200 mmol) in water (650 ml) was added a solution of sodium iodide (26.5 g, 180 mmol) and iodine (25.4 g, 100 mmol) in water (350 ml) over 90 min at room temperature. The reaction was stirred a further 30 min and filtered. The resulting white solid was washed with water and dried in vacuo at 50° C. $^1$H NMR (CD$_3$OD) d 2.20 (s, 3 H), 4.86 (br s, 1 H), 7.57 (s, 1 H).

Step B: 1-Boc-4-iodo-5-methylimidazole

A suspension of 4-iodo-5-methylimidazole (4.16 g, 20 mmol) and di-t-butyldicarbonate (5.24 g, 24 mmol) in methylene chloride (100 ml) containing triethylamine (4.0 ml, 28.7 mmol) was stirred at room temperature until homogeneity was achieved (2 h). The reaction mixture was then washed well with water, dried (Na$_2$SO$_4$) and concentrated. The residue was chromatographed (5:1 hexane/ethyl acetate) to afford the title compound as a crystalline white solid. $^1$H NMR (CDCl$_3$) d 1.62 (s, 9 H), 2.43 (s, 3 H), 8.00 (s, 1 H).

Step C: 1-Boc-5-methyl-4-imidazolepropargyl phthalimide

A mixture of 1-Boc-4-iodo-5-methylimidazole (936.8 mg, 3 mmol), copper (I) iodide (30 mg) and bis triphenylphosphinepalladiumdichloride (217.5 mg, 0.3 mmol) in triethylamine (30 ml) was heated at 60° C. for 10 min. There was incomplete dissolution of the catalyst. N-Propargylphthalimide (651.4 mg, 3.5 mmol) was added and the heating continued. Most of the solids went in then triethylamine hydroiodide was gradually deposited. After 4 h more alkyne (384.5 mg) was added. After 1 h the reaction mixture became difficult to stir and was then evaporated to dryness. The residue was redissolved in chloroform and adsorbed onto silica gel. Chromatography (5:4:1 ethyl acetate/hexane/chloroform) gave the title compound. $^1$H NMR (CDCl$_3$) d 1.61 (s, 9 H), 2.46 (s, 3 H), 4.70 (s, 2 H), 7.74 (m, 2 H), 7.89 (m, 2 H), 7.91 (s, 1 H).

Step D: 5-Methyl-4-imidazolepropargylamine

The phthaloyl group was removed from 1-Boc-5-methyl-4-imidazolepropargyl phthalimide as for EXAMPLE XV, Step F with the exception that the reaction was run at room temperature. The Boc group was labile under these conditions. $^1$H NMR (CD$_3$OD) d 2.25 (s, 3 H), 3.62 (s, 2 H), 4.95 (br s, 2 H), 7.47 (s, 1 H).

Step E: D-3,3-Diphenylalanine-L-proline-N-(5-methyl-4-imidazole-propargyl) amide Boc-D-3,3-diphenylalanine-L-proline and 5-methyl-4-imidazolepropargylamine were coupled essentially according to the procedure for EXAMPLE I, Step A then the Boc group was removed essentially according to the procedure of EXAMPLE IV, Step E. $^1$H NMR (CD$_3$OD) d 1.32 (m, 1 H), 1.77 (m, 3 H), 2.39 (s, 3 H), 2.79 (m, 1 H), 3.57 (m, 1 H), 4.06 (m, 1 H), 4.27 (dd, J=17.9 Hz, 2 H), 4.45 (d, J=11.4 Hz, 1 H), 4.98 (d, J=11.4 Hz, 1 H), 7.26–7.60 (m, 10 H), 8.75 (s, 1 H); MS (FAB) 456 (M+1)$^+$.

EXAMPLE XIX

Preparation of 3-Benzylsulfonylamino-6-methyl-1-(4-methylene-carboxamidopropylimidazolyl)-2-pyridinone

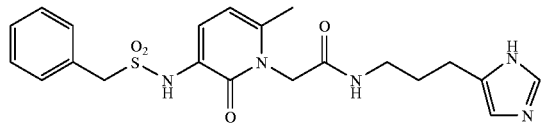

Step A: 3-Benzyloxycarbonylamino-6-methyl-2-pyridinone

DPPA (70 ml, 320 mmol) was added to a stirred solution of 2-hydroxy-6-methylpyridine-3-carboxylic acid (49 g, 320 mmol) and triethylamine (45 ml, 320 mmol) in dry dioxane (500 ml) and the resulting solution was heated to reflux. After 16 h more triethylamine (45 ml, 320 mmol) and benzyl alcohol (32 ml, 310 mmol) were added and the solution was refluxed for a further 24 h. The reaction was concentrated in vacuo to remove most of the volatiles. The residue was partitioned between 1:1 methylene chloride/chloroform and cold 1:1 brine/1M citric acid. There was partial formation of an emulsion. The aqueous phase was washed once with ether and the combined organics filtered through Celite to break up the colloid. The filtrate was washed with 1:1 saturated NaHCO$_3$/10% aqueous Na$_2$CO$_3$ solution and dried (Na$_2$SO$_4$). Concentration in vacuo gave a tan solid. Methanol was added to the crude product to give a slurry which was then filtered. The residue was washed with methanol until the filtrate was clear. Drying gave the title compound as an off-white powder. A further crop was obtained by evaporating the washings and chromatographing the residue (7:1.5:1.5 ethyl acetate/hexanes/chloroform): $^1$H NMR (CDCl$_3$) d 2.29 (s, 3H, CH$_3$), 5.20 (s, 2 H, PhCH$_2$), 6.06 (d, J=7.6 Hz, pyridinone-5-H), 7.32–7.43 (m, 5 H, Ph), 7.67 (br s, 1 H, CbzNH), 8.03 (br d, pyridinone-4-H).

Step B: 3-Benzyloxycarbonylamino-6-methyl-1-(t-butylmethylenecarboxy)-2-pyridinone Sodium hydride (5.3 g, 220 mmol) was added proportionwise to a well stirred slurry of 3-benzyloxycarbonylamino-6-methyl-2-pyridinone (53 g, 200 mmol) in THF (300 ml) at 0° C. By the end of the addition a brown solution had resulted. t-Butyl bromoacetate (45 ml, 270 mmol) was then added. Within minutes NaBr started separating out. After 1 h a thick white precipitate had formed. The reaction was stirred for an additional hour (bath temperature then 15° C.) then the THF was rotovapped off. The residue was partitioned between THF/methylene chloride (600 ml/100 ml) and half saturated brine (200 ml). The organic phase was dried (Na$_2$SO$_4$), filtered and concentrated. The resulting cream colored solid was triturated with hexane to give of N-alkylated material as a white microcrystalline solid: $^1$H NMR (CDCl$_3$) d 1.47 (s, 9 H), 2.25 (s, 3 H), 4.75 (s, 2 H), 5.19 (s, 2 H), 6.09 (d, J=7.8 Hz), 7.30–7.40 (m, 5 H), 7.75 (br s, 1 H), 7.94 (br d, 1 H).

Step C: 3-Amino-6-methyl-1-(t-butylmethylenecarboxy)-2-pyridinone

A mixture of 3-benzyloxycarbonylamino-6-methyl-1-(t-butylmethylenecarboxy)-2-pyridinone (10 g, 27 mmol) and Pearlman's catalyst (2 g) in 4:1 ethanol/water (250 ml) was shaken in a Parr apparatus under H$_2$ (50 psi) for 3 h. The reaction mixture was filtered through Celite and evaporated in vacuo. The solid residue was triturated with ether to give the title compound as a pale yellow crystalline solid: $^1$H NMR (CDCl$_3$) d 1.46 (s, 9 H, t-Bu), 2.18 (s, 3 H, Me), 4.02 (br s, 2 H, NH$_2$), 4.74 (s, 2 H, CH$_2$), 5.90 (d, J=7.3 Hz, 1 H, pyridinone H-5), 6.47 (d, J=7.3 Hz, 1 H, pyridinone H-4).

Step D: 3-Benzylsulfonylamino-6-methyl-1-(t-butylmethylenecarboxy)-2-pyridinone

Benzylsulfonyl chloride (5.2 g, 27 mmol) was added to a solution of 3-amino-6-methyl-1-(t-butylmethylenecarboxy)-2-pyridinone (6 g, 25 mmol) in pyridine (50 ml) at 0° C. and as the resulting solution was stirred a thick precipitate formed. After 1 h the reaction mixture was evaporated in vacuo to a thick paste. This was partitioned between ethylene chloride and 10% potassium hydrogen sulfate solution. The organic layer was dried (Na$_2$SO$_4$) and evaporated in vacuo to give a yellow solid which triturated first with hexane then ether. This gave the title compound as an off-white solid: $^1$H NMR (CDCl$_3$) d 1.51 (s, 9 H, t-Bu), 2.26 (s, 3 H, Me), 4.31 (s, 2 H, PhCH$_2$), 4.75 (s, 2 H, NCH$_2$), 6.01 (d, J=7.7 Hz, 1 H, pyridinone H-5), 7.22–7.34 (m, 7 H, remaining H).

Step E: 3-Benzylsulfonylamino-6-methyl-1-methylenecarboxy-2-pyridinone

HCl gas was bubbled through a stirred suspension of 3-benzylsulfonylamino-6-methyl-1-(t-butylmethylenecarboxy)-2-pyridinone (7.5 g, 19 mmol) in ethyl acetate (250 ml) at 0° C. until a solution had formed which was saturated with HCl. After 1 h at room temperature a thick suspension had formed. The mixture was degassed with argon and filtered to give the title compound as a pink solid: $^1$H NMR (CD$_3$OD) d 2.32 (s, 3 H, Me), 4.43 (s, 2 H, PhCH$_2$), 4.89 (s, 2 H, NCH$_2$), 6.14 (d, J=7.7 Hz, 1 H, pyridinone H-5), 7.28–7.33 (m, 6 H, remaining H).

Step F: 3-Benzylsulfonylamino-6-methyl-1-(trans-1-trityl-4-methylenecarboxamidoallylimidazolyl)-2-pyridinone The title compound was prepared from 3-benzylsulfonylamino-6-methyl-1-methylenecarboxy-2-pyridinone and trans-1-trityl-4-imidazoleallylamine using the procedure described in EXAMPLE I, Step A. $^1$H NMR (CDCl$_3$) d 2.40 (s, 3 H), 4.00 (t, J=6 Hz, 2 H), 4.30 (s, 2 H), 4.68 (s, 2 H), 6.02 (d, J=8 Hz, 1 H), 6.20–6.40 (m, 2 H), 6.60 (t, J=6 Hz, 1 H), 6.73 (s, 1 H), 7.08–7.40 (m, 21 H), 8.02 (s, 1 H).

Step G: 3-Benzylsulfonylamino-6-methyl-1-(trans-4-methylenecarboxamidoallylimidazolyl)-2-pyridinone The title compound was prepared from 3-benzylsulfonylamino-6-methyl-1-(trans-1-trityl-4-methylenecarboxamidoallylimidazolyl)-2-pyridinone using the procedure described in EXAMPLE IV, Step E. $^1$H NMR (CD$_3$OD) d 2.35 (s, 3 H), 4.05 (br m, 2 H), 4.45 (s, 2 H), 4.85 (s, 2 H), 6.19 (d, J=8 Hz, 1 H), 6.38 (d of t, J=16 and 6 Hz, 1 H), 6.58 (br d, J=16 Hz, 1 H), 7.20–7.37 (m, 6 H), 7.52 (s, 1 H), 8.60 (t, J=6 Hz, 1 H), 8.81 (s, 1 H).

Step H: 3-Benzylsulfonylamino-6-methyl-1-(4-methylenecarbox amido-propylimidazolyl)-2-pyridinone The title compound was prepared from 3-benzylsulfonylamino-6-methyl-1-(trans-4-methylenecarboxamidoallylimidazolyl)-2-pyridinone using the procedure described in EXAMPLE I, Step B. $^1$H NMR (CD$_3$OD) d 1.15–1.40 (m, 2 H), 1.89 (t, J=6.6 Hz, 2 H), 2.33 (s, 3 H), 2.77 (t, J=7 Hz, 2 H), 4.43 (s, 2 H), 4.79 (s, 2 H), 6.16 (d, J=7.3 Hz, 1 H), 7.15–7.40 (m, 7 H), 8.71 (s, 1 H); MS (FAB) 444 (M+1)$^+$.

EXAMPLE XX

Preparation of 3-Benzylsulfonylamino-6-methyl-1-(4-methyl-5-methylene-carboxamidomethylimidazolyl)-2-pyridinone

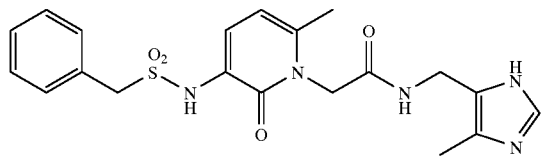

Step A: 1-Trityl-4-methyl-5-imidazolemethanol

A solution of 4-methyl-5-imidazolemethanol hydrochloride (6.0 g, 40 mmol), trityl chloride (12.3 g, 44 mmol), and triethylamine (16.4 ml, 120 mmol) in chloroform (200 ml) was stirred at room temperature overnight. The reaction mixture was washed with water, dried over MgSO$_4$, filtered and the solvents removed in vacuo. The crude material was purified by flash chromatography (24:1 CHCl$_3$/MeOH). $^1$H NMR (CDCl$_3$) d 1.42 (s, 3 H), 3.80 (br s, 1 H), 4.55 (s, 2 H), 7.10–7.40 (m, 16 H).

Step B: 5-Azidomethyl-4-methyl-1-tritylimidazole

To a solution of 1-trityl-4-methyl-5-imidazolemethanol (3.7 g, 10 mmol) and DPPA (3.0 ml, 13 mmol) in THF (100 ml) was added DBU (2.0 ml, 13 mmol). The resulting solution was heated to 60° C. for 2 h. The solvents were removed in vacuo and the residue purified by flash chromatography (2:1 hexane/ethyl acetate) to give of the title compound. $^1$H NMR (CDCl$_3$) d 1.42 (s, 3 H), 4.22 (s, 2 H), 7.10–7.35 (m, 16 H).

Step C: 1-Trityl-4-methyl-5-imidazolemethylamine

To a solution of 5-azidomethyl-4-methyl-1-tritylimidazole (3.0 g, 7.9 mmol) in THF (70 ml) was added triphenylphosphine (5.18 g, 19.8 mmol). The resulting solution was refluxed for 1.5 h then water (5 ml) was added. Refluxing was continued for an additional 24 hours. After cooling to room temperature, the solvents were removed in vacuo and the crude reaction mixture was purified by chromatography on silica gel (19:1 chloroform/10% NH$_4$OH in methanol) to give of the title compound. $^1$H NMR (CDCl$_3$) d 1.40 (s, 3 H), 1.70 (br s, 2 H), 3.70 (s, 2 H), 7.10–7.35 (m, 16 H).

Step D: 3-Benzylsulfonylamino-6-methyl-1-(1-trityl-4-methyl-5-methylenecarboxamidomethylimidazolyl)-2-pyridinone The title compound was prepared from 3-benzylsulfonylamino-6-methyl-1-methylenecarboxy-2-pyridinone and 1-trityl-4-methyl-5-imidazolemethylamine using the procedure described in EXAMPLE I, Step A. $^1$H NMR (CDCl$_3$) d 1.40 (s, 3 H), 2.39 (s, 3 H), 4.25–4.35 (m, 4 H), 4.78 (s, 2 H), 6.01 (d, J=8 Hz, 1 H), 6.85–7.05 (br s, 1 H), 7.10–7.35 (m, 22 H).

Step E: 3-Benzylsulfonylamino-6-methyl-1-(4-methyl-5-methyl-ene-carboxamidomethylimidazolyl)-2-pyridinone The title compound was prepared from 3-benzylsulfonylamino-6-methyl-1-(1-trityl-4-methyl-5-methylenecarboxamidomethylimidazolyl)-2-pyridinone using the procedure described in EXAMPLE IV, Step E. $^1$H NMR (CD$_3$OD) d 2.31 (s, 3 H), 2.34 (s, 3 H), 4.40 (s, 2 H), 4.42 (s, 2 H), 4.80 (s, 2 H), 6.16 (d, J=7 Hz, 1 H), 7.20–7.35 (m, 6 H), 8.65 (s, 1 H); MS (FAB) 430 (M+1)$^+$.

EXAMPLE XXI

Preparation of 3-(4-Chlorobenzylsulfonylamino)-6-methyl-1-(4-methyl-5-methylenecarboxamidomethylimidazolyl)-2-pyridinone

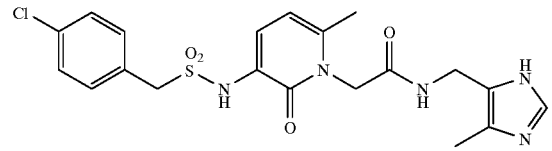

Step A: Sodium 4-chlorobenzylthiosulfate

To a solution of 4-chlorobenzyl chloride (10.0 g, 62 mmol) in 1:1 methanol/water (100 ml) was added sodium thiosulfate (9.81 g, 62 mmol). The resulting solution was then refluxed for 24 h. After cooling to room temperature, the solvents were removed in vacuo and the residue triturated with ether to give the title compound as a white solid. $^1$H NMR (CD$_3$OD) d 4.25 (s, 2 H), 7.32 (q, J=33, 9 Hz, 4 H).

Step B: 4-Chlorobenzylsulfonyl chloride

Chlorine gas was slowly bubbled through a cooled (0° C.) solution of sodium 4-chlorobenzylthiosulfate (11.2 g, 56 mmol) in acetic acid (100 ml) to which ice (10 g) had been added. Additional ice was added as necessary to maintain the temperature <10° C. After 0.5 h the addition of chlorine was stopped and the resulting yellow solution was allowed to stir at 0° C. for 1 h. The solution was then extracted with ether and the organics washed twice with cold 5% sodium bisulfite solution. Drying over MgSO$_4$, filtration and removal of the solvents in vacuo gave the title compound as a white solid. $^1$H NMR (CDCl$_3$) d 4.82 (s, 2 H), 7.45 (m, 4 H).

Step C: 3-(4-Chlorobenzylsulfonylamino)-6-methyl-1-(t-butylmethylenecarboxy)-2-pyridinone To a solution of 3-amino-6-methyl-1-(t-butylmethylenecarboxy)-2-pyridinone (600 mg, 2.5 mmol)

in pyridine (50 ml) was added 4-chlorobenzylsulfonyl chloride (830 mg, 3.75 mmol). The resulting red solution was stirred at room temperature overnight. The solvents were removed in vacuo and the crude material purified by preparative HPLC. $^1$H NMR (CDCl$_3$) d 1.51 (s, 9 H), 2.27 (s, 3 H), 4.27 (s, 2 H), 4.75 (s, 2 H), 6.03 (d, J=8 Hz, 1 H), 7.17–7.30 (m, 4 H), 7.35 (d, J=8 Hz, 1 H).

Step D: 3-(4-Chlorobenzylsulfonylamino)-6-methyl-1-methylenecarboxy-2-pyridinone Hydrogen chloride gas was bubbled through a suspension of 3-(4-chlorobenzylsulfonylamino)-6-methyl-1-(t-butyl-methylenecarboxy)-2-pyridinone (850 mg, 2.0 mmol) in ethyl acetate (100 ml) that had been cooled to 0° C. After 15 min the addition of HCl gas was stopped and the solution warmed to room temperature for 1 h. The mixture was then purged with nitrogen and the solvent removed in vacuo to give the title compound as a solid. $^1$H NMR (CH$_3$OD) d 2.33 (s, 3 H), 4.43 (s, 2 H), 4.88 (s, 2 H), 6.12 (d, J=7.6 Hz, 1 H), 7.29 (s, 4 H), 7.34 (d, J=7.8 Hz, 1 H).

Step E: 3-(4-Chlorobenzylsulfonylamino)-6-methyl-1-(1-trityl-4-methyl-5-methylenecarboxamidomethylimidazolyl)-2-pyridinone The title compound was prepared from 3-(4-chlorobenzylsulfonylamino)-6-methyl-1-methylenecarboxy-2-pyridinone and 1-trityl-4-methyl-5-imidazolemethylamine using the procedure described in EXAMPLE I, Step A. $^1$H NMR (CDCl$_3$) d 1.40 (s, 3 H), 2.39 (s, 3 H), 4.25–4.35 (m, 4 H), 4.78 (s, 2 H), 6.01 (d, J=8 Hz, 1 H), 6.85–7.05 (br s, 1 H), 7.10–7.35 (m, 22 H).

Step F: 3-(4-Chlorobenzylsulfonylamino-6-methyl-1-(4-methyl-5-methylenecarboxamidomethylimidazolyl)-2-pyridinone The title compound was prepared from 3-(4-chlorobenzylsulfonylamino-6-methyl-1-(1-trityl-4-methyl-5-methylenecarboxamidomethyl-imidazolyl)-2-pyridinone using the procedure described in EXAMPLE IV, Step E. $^1$H NMR (CD$_3$OD) d 2.33 (s, 3 H), 2.35 (s, 3 H), 4.43 (s, 2 H), 4.46 (s, 2 H), 4.81 (s, 2 H), 6.17 (d, J=8 Hz, 1 H), 7.20–7.30 (m, 4 H), 7.35 (d, J=7.5 Hz, 1 H), 8.68 (s, 1 H); MS (FAB) 464 (M+1)$^+$.

EXAMPLE XXII

Preparation of 3-Benzylsulfonylamino-6-methyl-1-(1'-t-butoxycarbonylmethyl-4-methyl-5-methylenecarboxamidomethyl-imidazolyl)-2-pyridinone

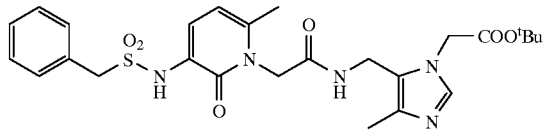

Step A: 1-t-Butoxycarbonylmethyl-4-methyl-5-hydroxymethylimidazole t-Butyl bromoacetate (35 ml, 240 mmol) was added to a mixture of 4-methyl-5-imidazolemethanol hydrochloride (30 g, 200 mmol) and potassium carbonate (80 g, 580 mmol) in N,N-dimethylformamide (500 ml) and the resulting heterogenous mixture stirred at room temperature for 24 h. The reaction mixture was filtered through Celite and the DMF was then removed in vacuo from the filtrate. The residue was dissolved in a minimum quantity of methylene chloride and the resulting solution diluted several fold with ether and ethyl acetate. This solution was washed well with cold water and dried over sodium sulfate. Filtration and concentration gave a cream colored solid (16 g) which was determined by NMR analysis to be a 2:1 mixture of 1-t-butoxycarbonyl-methyl-4-methyl-5-hydroxymethylimidazole and 3-t-butoxycarbonyl-methyl-4-methyl-5-hydroxymethylimidazole respectively. The two isomers displayed very similar mobility on TLC but were separable by careful gradient elution chromatography on silica gel (99:1 to 19:1 chloroform/methanol): N-1 isomer $^1$H NMR (CDCl$_3$) d 1.46 (s, 9 H), 2.23 (s, 3 H), 4.55 (s, 2 H), 4.63 (s, 2 H), 7.35 (s, 1 H); N-3 isomer $^1$H NMR (CDCl$_3$) d 1.48 (s, 9 H), 2.17 (s, 3 H), 4.47 (s, 2 H), 4.56 (s, 2 H), 7.39 (s, 1 H).

Step B: 1-t-Butoxycarbonylmethyl-4-methyl-5-azidomethylimidazole

A solution of 1-t-butoxycarbonylmethyl-4-methyl-5-hydroxymethylimidazole (4.61 g, 20 mmol) in DMF (100 ml) was cooled to 0° C. and treated sequentially with diphenylphosphoryl azide (5.4 ml, 25 mmol) and DBU (3.7 ml, 25 ml). The resulting solution was allowed to warm gradually to room temperature and was then stirred there overnight. The DMF was rotavapped off, the residue dissolved in a minimum quantity of methylene chloride and the resulting solution diluted several fold with ether and ethyl acetate. This solution was washed sequentially with 1M citric acid, water, 10% sodium carbonate, brine and then dried over magnesium sulfate. Filtration and concentration gave an oil which was purified by flash chromatography (19:1 chloroform/methanol) to give the title compound as an oil: $^1$H NMR (CDCl$_3$) d 1.48 (s, 9 H), 2.27 (s, 3 H), 4.28 (s, 2 H), 4.56 (s, 2 H), 7.43 (s, 1 H).

Step C: 1-t-Butoxycarbonylmethyl-4-methyl-5-aminomethylimidazole

A solution of 1-t-butoxycarbonylmethyl-4-methyl-5-azidomethylimidazole (2.9 g) in ethyl acetate (100 ml) containing 10% palladium on carbon (1.5 g) was stirred at room temperature under an atmosphere of hydrogen for 3 h. After removal of the catalyst by filtration through Celite, the filtrate was concentrated to give the amine as a colorless oil: $^1$H NMR (CD$_3$OD) d 1.48 (s, 9 H), 2.19 (s, 3 H), 3.69 (s, 2 H), 4.81 (s, 2 H), 7.49 (s, 1 H).

Step D: 3-Benzylsulfonamino-6-methyl-1-(1-t-butoxycarbonylmethyl-4-methyl-5-methylenecarboxamidomethylimidazolyl)-2-pyridinone The title compound was prepared from 3-benzylsulfonylamino-6-methyl-1-methylenecarboxy-2-pyridinone and 1-t-butoxycarbonylmethyl-4-methyl-5-aminomethylimidazole essentially according to the procedure of EXAMPLE I, Step A: $^1$H NMR (CD$_3$OD) d 1.41 (s, 9 H, t-Bu), 2.36 (s, 3 H, pyridinone Me), 2.37 (s, 3 H, imidazole Me), 4.27 (s, 2 H, PhCH$_2$), 4.36 (d, J=5.7 Hz, 2 H, imidazoleCH$_2$N), 4.51 (s, 2 H, pyridinoneNCH$_2$), 4.86 (s, 2 H, imidazoleNCH$_2$), 6.06 (d, J=7.9 Hz, 1 H, pyridinone H$_5$), 7.15–7.26 (m, 6 H, Ph and pyridinone H$_6$), 8.08 (br s, 1 H, SO$_2$NH), 8.28 (br s, 1 H, CONH), 8.48 (s, 1 H, imidazole H$_2$); MS (FAB) 544 (M+1)$^+$.

EXAMPLE XXIII

Preparation of 3-Benzylsulfonylamino-6-methyl-1-(1-carboxymethyl-4-methyl-5-methylenecarboxamidomethylimidazolyl)-2-pyridinone

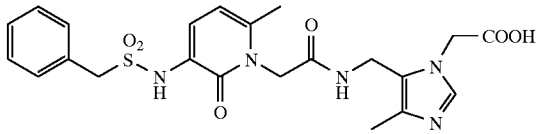

The title compound was prepared from 3-benzylsulfonamino-6-methyl-1-(1-t-butoxycarbonyl-methyl-4-methyl-5-methylenecarboxamido-methylimidazolyl)-2-pyridinone essentially according to the procedure of EXAMPLE XXI, Step D: $^1$H NMR (CD$_3$OD) d 2.31 (s, 3 H), 2.41 (s, 3 H), 4.44 (s, 2 H), 4.46 (m, 2 H), 4.73 (s, 2 H), 5.17 (s, 2 H), 6.13 (d, J=7 Hz, 1 H), 7.30 (m, 6 H), 8.74 (br s, 1 H), 8.81 (s, 1 H); MS (FAB) 488 (M+1)$^+$.

EXAMPLE XXIV

Preparation of 3-Benzylsulfonylamino-6-methyl-1-(1-t-butylaminocarbonylmethyl-4-methyl-5-methylenecarboxamidomethylimidazolyl)-2-pyridinone

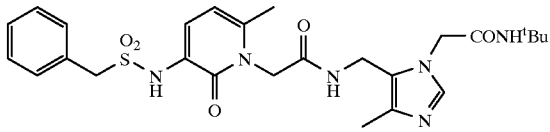

The title compound was prepared from 3-benzylsulfonamino-6-methyl-1-(1-carboxymethyl-4-methyl-5-methylenecarboxamidomethyl-imidazolyl)-2-pyridinone and t-butylamine essentially according to the procedure of EXAMPLE I, Step A: $^1$H NMR (CD$_3$OD) d 1.33 (s, 9 H), 2.32 (s, 3 H), 2.39 (s, 3 H), 4.41 (m, 2 H), 4.45 (s, 2 H), 4.75 (s, 2 H), 4.99 (s, 2 H), 6.15 (d, J=7.5 Hz, 1 H), 7.26–7.34 (m, 6 H), 7.89 (br s, 1 H), 8.67 (br t, 1 H), 8.74 (s, 1 H); MS (FAB) 544 (M+1)$^+$.

EXAMPLE XXV

Preparation of 3-Benzylsulfonylamino-6-methyl-1-(1-ethylaminocarbonyl-methyl-4-methyl-5-methylenecarboxamidomethylimidazolyl)-2-pyridinone

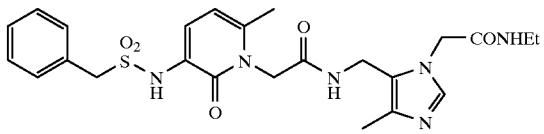

The title compound was prepared from 3-benzylsulfonamino-6-methyl-1-(1-carboxymethyl-4-methyl-5-methylenecarboxamidomethyl-imidazolyl)-2-pyridinone and ethylamine hydrochloride essentially according to the procedure of EXAMPLE I, Step A: $^1$H NMR (CD$_3$OD) d 1.13 (t, J=7.3 Hz, 3 H), 2.32 (s, 3 H), 2.39 (s, 3 H), 3.26 (m, 2 H), 4.43 (m, 2 H), 4.45 (s, 2 H), 4.75 (s, 2 H), 5.05 (s, 2 H), 6.15 (d, J=7.7 Hz, 1 H), 7.26–7.34 (m, 6 H), 8.25 (br s, 1 H), 8.64 (br t, 1 H), 8.77 (s, 1 H); MS (FAB) 515 (M+1)$^+$.

EXAMPLE XXVI

Preparation of 3-Benzylsulfonylamino-6-methyl-1-(1-cyclopropylaminocarbonylmethyl-4-methyl-5-methylenecarboxamidomethylimidazolyl)-2-pyridinone

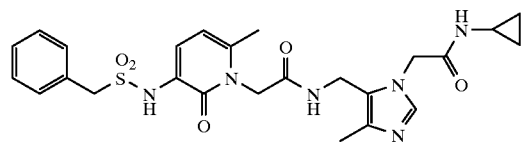

The title compound was prepared from 3-benzylsulfonamino-6-methyl-1-(1-carboxymethyl-4-methyl-5-methylenecarboxamidomethyl-imidazolyl)-2-pyridinone and cyclopropylamine essentially according to the procedure of EXAMPLE I, Step A: $^1$H NMR (CD$_3$OD) d 0.72 (m, 4 H), 2.32 (s, 3 H), 2.40 (s, 3 H), 2.70 (m, 1 H), 4.43 (m, 2 H), 4.45 (s, 2 H), 4.74 (s, 2 H), 5.02 (s, 2 H), 6.15 (d, J=7.7 Hz, 1 H), 7.24–7.36 (m, 6 H), 8.39 (br s, 1 H), 8.67 (br t, 1 H), 8.76 (s, 1 H); MS (FAB) 527 (M+1)$^+$.

EXAMPLE XXVII

Preparation of 3-Benzylsulfonylamino-6-methyl-1-(1-cyclopropylmethylaminocarbonylmethyl-4-methyl-5-methylenecarboxamidomethylimidazolyl)-2-pyridinone

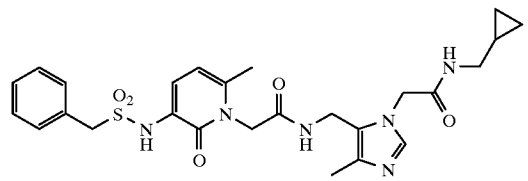

The title compound was prepared from 3-benzylsulfonamino-6-methyl-1-(1-carboxymethyl-4-methyl-5-methylenecarboxamidomethyl-imidazolyl)-2-pyridinone and cyclopropylmethylamine essentially according to the procedure of EXAMPLE I, Step A: $^1$H NMR (CD$_3$OD) d 0.20 (d, J=4.7 Hz, 2 H), 0.49 (d, J=6.9 Hz, 2 H), 0.96 (br m, 1 H), 2.31 (s, 3 H), 2.39 (s, 3 H), 3.07 (d, J=7 Hz, 2 H), 4.43 (s, 2 H), 4.44 (s, 2 H), 4.74 (s, 2 H), 5.07 (s, 2 H), 6.15 (d, J=7.9 Hz, 1 H), 7.28 (m, 6 H), 8.77 (s, 1 H); MS (FAB) 541 (M+1)$^+$.

EXAMPLE XXVIII

Preparation of 3-Benzylsulfonylamino-6-methyl-1-[1-(1,1-dimethylpropylaminocarbonylmethyl)-4-methyl-5-methylenecarboxamidomethylimidazolyl]-2-pyridinone

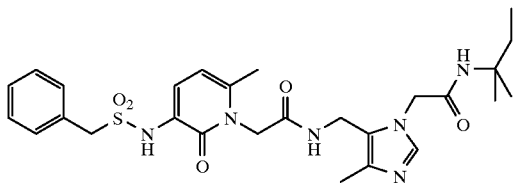

The title compound was prepared from 3-benzylsulfonamino-6-methyl-1-(1-carboxymethyl-4-methyl-5-methylenecarboxamidomethyl-imidazolyl)-2-pyridinone and t-amylamine essentially according to the procedure of EXAMPLE I, Step A: $^1$H NMR (CD$_3$OD) d 0.85 (t, J=7.5 Hz, 3 H), 1.28 (s, 6 H), 1.70 (q, J=7.5 Hz, 2 H), 2.32 (s, 3 H), 2.38 (s, 3 H), 4.40 (s, 2 H), 4.44 (s, 2 H), 4.75 (s, 2 H), 5.01 (s, 2 H), 6.15 (d, J=7.7 Hz, 1 H), 7.28 (m, 6 H), 7.78 (s, 1 H), 8.74 (s, 1 H); MS (FAB) 557 (M+1)$^+$.

EXAMPLE XXIX

Preparation of 3-Benzylsulfonylamino-6-methyl-1-(1-t-butylmethylaminocarbonylmethyl)-4-methyl-5-methylenecarboxamidomethyl-imidazolyl]-2-pyridinone

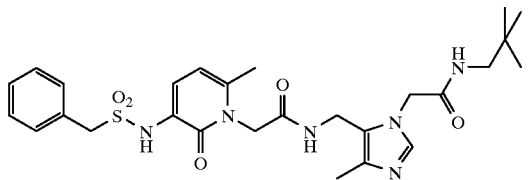

Step A: 1-Carboxymethyl-4-methyl-5-azidomethylimidazole

The title compound was prepared from 1-t-butoxycarbonylmethyl-4-methyl-5-azidomethylimidazole using the procedure described in EXAMPLE XXI, Step D. $^1$H NMR (CD$_3$OD) d 2.43 (s, 3 H), 4.61 (s, 2 H), 5.13 (s, 2 H), 8.94 (s, 1 H).

Step B: 1-t-Butylmethylaminocarbonylmethyl-4-methyl-5-azidomethylimidazole

The title compound was prepared from 1-carboxymethyl-4-methyl-5-azidomethylimidazole and t-butylmethylamine using the procedure described in EXAMPLE I, Step A. $^1$H NMR (CDCl$_3$) d 0.84 (s, 9 H), 2.30 (s, 3 H), 3.05 (d, J=6.4 Hz, 2 H), 4.35 (s, 2 H), 4.62 (s, 2 H), 5.45 (br s, 1 H), 7.50 (s, 1 H).

Step C: 1-t-Butylmethylaminocarbonylmethyl-4-methyl-5-aminomethylimidazole

A solution of 1-t-butylmethylaminocarbonylmethyl-4-methyl-5-azidomethylimidazole (400 mg) and 10% Pd/C (400 mg) in ethyl acetate (60 ml) was hydrogenated at atmospheric pressure for 4 h. The solution was filtered through Celite and the solvents removed in vacuo to give the title compound. $^1$H NMR (CDCl$_3$) d 0.80 (s, 9 H), 1.61 (br s, 2 H), 2.23 (s, 3 H), 2.99 (d, J=6.1 Hz, 2 H), 3.86 (s, 2 H), 4.63 (s, 2 H), 7.50 (s, 1 H).

Step D: 3-Benzylsulfonylamino-6-methyl-1-(1-t-butylmethylaminocarbonylmethyl-4-methyl-5-methylenecarboxamidomethylimidazolyl)2-pyridinone The title compound was prepared from 3-benzylsulfonamino-6-methyl-1-methylenecarboxy-2-pyridinone and 1-t-butylmethylamino-carbonylmethyl-4-methyl-5-aminomethylimidazole essentially according to the procedure of EXAMPLE I, Step A: $^1$H NMR (CD$_3$OD) d 0.90 (s, 9 H), 2.31 (s, 3 H), 2.39 (s, 3 H), 3.04 (d, J=6.1 Hz, 2 H), 4.43 (m, 4 H), 4.88 (s, 2 H), 5.12 (s, 2 H), 6.15 (d, J=7.5 Hz, 1 H), 7.26–7.34 (m, 6 H), 8.25 (br s, 1 H), 8.71 (br t, 1 H), 8.77 (s, 1 H); MS (FAB) 557 (M+1)$^+$.

EXAMPLE XXX

Preparation of 3-Benzylsulfonylamino-6-methyl-1-[1-(2,2,2-trifluoroethylaminocarbonylmethyl)-4-methyl-5-methylenecarboxamidomethyl-imidazolyl]-2-pyridinone

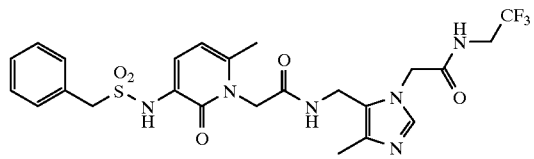

The title compound was prepared from 3-benzylsulfonamino-6-methyl-1-(1-carboxymethyl-4-methyl-5-methylenecarboxamidomethyl-imidazolyl)-2-pyridinone and 2,2,2-trifluoroethylamine hydrochloride essentially according to the procedure of EXAMPLE I, Step A: $^1$H NMR (CD$_3$OD) d 2.30 (s, 3 H), 2.39 (s, 3 H), 3.95 (q, J=9.1 Hz, 2 H), 4.41 (s, 2 H), 4.44 (s, 2 H), 4.74 (s, 2 H), 5.16 (s, 2 H), 6.14 (d, J=7.5 Hz, 1 H), 7.26–7.31 (m, 6 H), 8.77 (s, 1 H); MS (FAB) 569 (M+1)$^+$.

EXAMPLE XXXI

Preparation of 3-Benzylsulfonylamino-6-methyl-1-[1-(N-morpholinocarbonylmethyl)-4-methyl-5-methylenecarboxamidomethylimidazolyl]-2-pyridinone

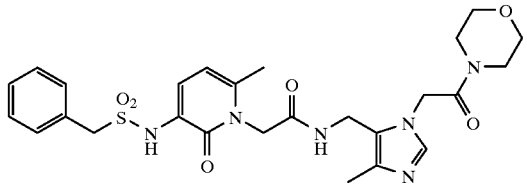

The title compound was prepared from 3-benzylsulfonamino-6-methyl-1-(1-carboxymethyl-4-methyl-5-methylenecarboxamidomethyl-imidazolyl)-2-pyridinone and morpholine essentially according to the procedure of EXAMPLE I, Step A: $^1$H NMR (CD$_3$OD) d 2.32 (s, 3 H), 2.40 (s, 3 H), 3.40 (d, J=4.4 Hz, 2 H), 3.57 (d, J=16.3 Hz, 2 H), 3.63 (dd, J=5.4 Hz, 4 H), 4.45 (s, 2 H), 4.46 (s, 2 H), 4.70 (s, 2 H), 5.25 (s, 2 H), 6.14 (d, J=7.5 Hz, 1 H), 7.24 (d, J=7.7 Hz, 1 H), 7.32 (m, 5 H), 8.64 (br t, 1 H), 8.71 (s, 1 H); MS (FAB) 557 (M+1)$^+$.

EXAMPLE XXXII

Preparation of 3-Benzylsulfonylamino-6-methyl-1-[1-(3-hydroxyazetidine-1-carbonylmethyl)-4-methyl-5-methylenecarboxamidomethylimidazolyl]-2-pyridinone

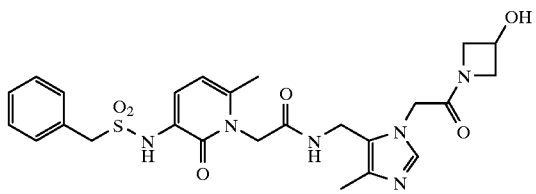

The title compound was prepared from 3-benzylsulfonamino-6-methyl-1-(1-carboxymethyl-4-methyl-5-methylenecarboxamidomethyl-imidazolyl)-2-pyridinone and 3-hydroxyazetidine essentially according to the procedure of EXAMPLE X, Step Y: $^1$H NMR (CD$_3$OD) d 2.31 (s, 3 H), 2.39 (s, 3 H), 3.82 (m, 1 H), 4.03 (m, 1 H), 4.24 (m, 1 H), 4.42 (m, 1 H), 4.44 (s, 6 H), 4.50 (m, 1 H), 4.73 (s, 2 H), 5.04 (s, 2 H), 6.15 (d, J=7.7 Hz, 1 H), 7.30 (m, 6 H), 8.72 (s, 1 H); MS (FAB) 543 (M+1)$^+$.

EXAMPLE XXXIII

Preparation of 3-Benzylsulfonylamino-6-methyl-1-[1-(2-hydroxyethylaminocarbonylmethyl)-4-methyl-5-methylenecarboxamidomethylimidazolyl]-2-pyridinone

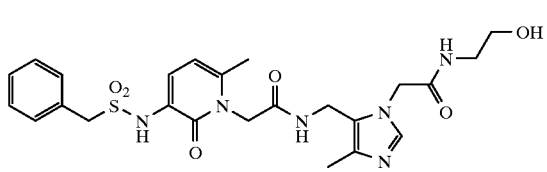

The title compound was prepared from 3-benzylsulfonamino-6-methyl-1-(1-carboxymethyl-4-methyl-5-methylenecarboxamidomethyl-imidazolyl)-2-pyridinone and hydroxyethylamine essentially according to the procedure of EXAMPLE I, Step A: $^1$H NMR (CD$_3$OD) d 2.30 (s, 3 H), 2.38 (s, 3 H), 3.34 (t, J=5 Hz, 2 H), 3.61 (t, J=5.5 Hz, 2 H), 4.44 (s, 4 H), 4.74 (s, 2 H), 5.06 (s, 2 H), 6.15 (d, J=7.5 Hz, 1 H), 7.28 (m, 6 H), 8.76 (s, 1 H); MS (FAB) 531 (M+1)+.

EXAMPLE XXXIV

Preparation of 3-Benzylsulfonylamino-6-methyl-1-[1-(2-aminoethylaminocarbonylmethyl)-4-methyl-5-methylenecarboxamidomethylimidazolyl]-2-pyridinone

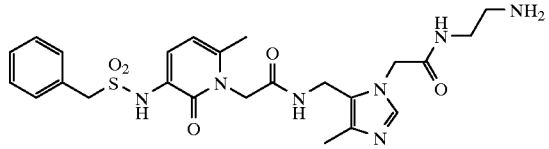

Step A: Bocaminoethylamine

A solution of di-t-butyl dicarbonate (6.98 g, 32 mmol) in dioxane (50 ml) was added in a slow dropwise manner to a cooled (0° C.) solution of ethylenediamine (2.2 ml, 32 mmol) in dioxane (30 ml). Upon completion of the addition, the reaction mixture was stirred overnight at room temperature. After filtration to remove a white precipitate, the filtrate was concentrated. The residue was partitioned between water and methylene chloride. The organic phase was dried (Na$_2$SO$_4$) and concentrated to give the title compound as an oil which partially crystallized. $^1$H NMR (CDCl$_3$) d 1.45 (s, 9 H), 2.80 (m, 2 H), 3.16 (m, 2 H).

Step B: 3-Benzylsulfonylamino-6-methyl-1-[1-(2-aminoethylaminocarbonylmethyl)-4-methyl-5-methylenecarboxamidomethylimidazolyl]-2-pyridinone 3-Benzylsulfonamino-6-methyl-1-(1-carboxymethyl-4-methyl-5-methylenecarboxamidomethylimidazolyl)-2-pyridinone and Bocamino-ethylamine were coupled essentially according to the procedure of EXAMPLE I, Step A. Removal of the Boc protecting group according to the procedure of EXAMPLE XXI, Step D gave the title compound: $^1$H NMR (CD$_3$OD) d 2.32 (s, 3 H), 2.39 (s, 3 H), 3.04 (t, J=5.7 Hz, 2 H), 4.49 (s, 2 H), 4.51 (s, 2 H), 4.76 (s, 2 H), 5.12 (s, 2 H), 5.31 (t, J=5.7 Hz, 2 H), 6.15 (d, J=7.5 Hz, 1 H), 7.20 (d, J=7.7 Hz, 1 H), 7.34 (m, 5 H), 8.77 (s, 1 H); MS (FAB) 531 (M+1)$^+$.

EXAMPLE XXXV

Preparation of 3-(4-Chlorobenzylsulfonylamino)-6-methyl-1-(1-t-butylaminocarbonylmethyl-4-methyl-5-methylenecarboxamidomethyl-imidazolyl)-2-pyridinone

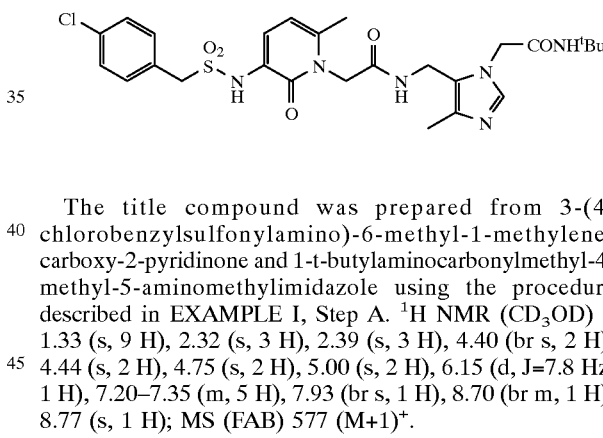

The title compound was prepared from 3-(4-chlorobenzylsulfonylamino)-6-methyl-1-methylenecarboxy-2-pyridinone and 1-t-butylaminocarbonylmethyl-4-methyl-5-aminomethylimidazole using the procedure described in EXAMPLE I, Step A. $^1$H NMR (CD$_3$OD) d 1.33 (s, 9 H), 2.32 (s, 3 H), 2.39 (s, 3 H), 4.40 (br s, 2 H), 4.44 (s, 2 H), 4.75 (s, 2 H), 5.00 (s, 2 H), 6.15 (d, J=7.8 Hz, 1 H), 7.20–7.35 (m, 5 H), 7.93 (br s, 1 H), 8.70 (br m, 1 H), 8.77 (s, 1 H); MS (FAB) 577 (M+1)$^+$.

EXAMPLE XXXVI

Preparation of 3-Benzylsulfonylamino-6-propyl-1-(1-t-butylaminocarbonylmethyl-4-methyl-5-methylenecarboxamidomethylimidazolyl)-2-pyridinone

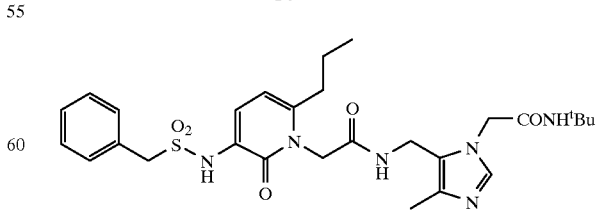

Step A: b-N,N-Dimethylaminoethenylcyclopropyl ketone

A mixture of cyclopropyl methyl ketone (5.88 ml, 59 mmol) and N,N-dimethylformamide dimethyl acetal (7.83 ml, 59 mmol) was heated in the presence of a catalytic quantity of p-toluenesulfonic acid for 48 h. The resulting crude sample of the title compound (a pale yellow oil) was used in subsequent reactions without further purification: $^1$H NMR (CDCl$_3$) d 0.74 (m, 2 H), 1.00 (m, 2 H), 1.75 (m, 1 H), 3.48 (s, 3 H), 3.50 (s, 3 H), 5.20 (d, 1 H), 7.55 (d, 1 H).

Step B: 6-Cyclopropyl-3-nitro-2-pyridinone

A mixture of crude b-N,N-dimethylaminoethenylcyclopropyl ketone (12 g, <86 mmol), nitroacetamide (9 g, 86 mmol) and aqueous piperidinium acetate (10 ml) [prepared from glacial acetic acid (42 ml), water (100 ml) and piperidine (72 ml)] was stirred at room temperature overnight. Following dilution with water (20 ml), the yellow precipitate was isolated via filtration and drying in vacuo to yield the title compound: $^1$H NMR (CDCl$_3$) d 1.15 (m, 2 H), 1.36 (m, 2 H), 2.10 (m, 1 H), 6.02 (br d, J=8.0 Hz, 1 H), 8.41 (d, J=8.0 Hz, 1 H).

Step C: 3-Amino-6-propyl-2-pyridinone

A mixture of 6-cyclopropyl-3-nitro-2-pyridinone (2 g, 13.3 mmol) and 10% palladium on carbon (600 mg) in ethyl acetate (100 ml) was stirred at room temperature under an atmosphere of hydrogen overnight. The catalyst was removed by filtration through a bed of Celite and the filtrate concentrated to yield product as a white microcrystalline solid. $^1$H NMR (CDCl$_3$) d 0.94 (t, J=7.3 Hz, 3 H), 1.67 (m, 2 H), 2.49 (t, J=7.5 Hz, 2 H), 4.00 (br s), 5.88 (d, J=7.1 Hz, 1 H), 6.59 (d, J=7.1 Hz, 1 H).

Step D: 3-Benzyloxycarbonylamino-6-propyl-2-pyridinone

Benzyl chloroformate (1.8 ml, 12.6 mmol) was added to a solution of 3-amino-6-propyl-2-pyridinone (1.63 g, 10.8 mmol) in a mixture of dioxane (25 ml) and 1N NaOH at 0° C. Within minutes a white precipitate formed. The reaction mixture was stirred at the same temperature for 1 h then at room temperature for 1 h. The reaction mixture was diluted with water and extracted with ethyl acetate then methylene chloride. Each extract was washed with brine then combined and dried over magnesium sulfate. Removal of the solvents in vacuo gave a yellow semi-solid which was a mixture of starting material and product. This was redissolved in a mixture of dioxane (24 ml) and 10% aqueous sodium carbonate (12 ml) and cooled to 0° C. Benzyl chloroformate (1.5 ml, 10.5 mmol) was once again added and after stirring for 0.5 h, the reaction mixture was allowed to stir at room temperature for 3 h. After dilution with water, the precipitate was filtered off and washed thoroughly, first with water and then with ether. Drying gave the title compound as a white powder: $^1$H NMR (CDCl$_3$) d 0.96 (t, J=7.3 Hz, 3 H), 1.68 (m, 2 H), 2.52 (t, J=7.5 Hz, 2 H), 5.22 (s, 2 H), 6.07 (d, J=7.5 Hz, 1 H), 7.34–7.43 (m, 4 H), 7.68 (s, 1 H), 8.05 (br d, J=5.3 Hz, 1 H).

Step E 3-Benzyloxycarbonylamino-6-propyl-1-(t-butylmethylenecarboxy)-2-pyridinone Solid 3-benzyloxycarbonylamino-6-propyl-2-pyridinone (2.64 g, 9.3 mmol) was added in small portions to a suspension of sodium hydride (269 mg, 11.2 mmol) in THF (30 ml) at 0° C. The reaction mixture was the stirred at room temperature for 20 min by which time an almost completely homogeneous solution had been obtained. Tert-butylbromoacetate (2.2 ml, 14.9 mmol) was then added. Within minutes a white precipitate started forming. Stirring was continued overnight, then the THF was evaporated in vacuo. Ice was carefully added to the residue to destroy any unreacted sodium hydride. Brine was added and the resulting mixture was extracted with 2:1:1 ethyl acetate/ether/chloroform and the combined extracts were dried over magnesium sulfate. Filtration and evaporation of the filtrate gave a cream solid which was purified by flash column chromatography eluting with 3:1:1 hexane/chloroform/ethyl acetate. This gave the title compound as a white crystalline solid: $^1$H NMR (CDCl$_3$) d 1.00 (t, J=7.3 Hz, 3 H), 1.48 (s, 9 H), 1.64 (m, 2 H), 2.46 (t, J=7.6 Hz, 2 H), 4.72 (s, 2 H), 5.20 (s, 2 H), 6.08 (d, J=7.7 Hz, 1 H), 7.31–7.40 (m, 4 H), 7.77 (s, 1 H), 7.97 (br d, J=7.0 Hz, 1 H).

Step F: 3-Amino-6-propyl-1-(t-butylmethylenecarboxy)-2-pyridinone

3-Benzyloxycarbonylamino-6-propyl-1-(t-butylmethylenecarboxy)-2-pyridinone (2.38 g, mmol) was dissolved in a 1:1 mixture of ethyl acetate and ethanol (100 ml) and then stirred in the presence of 20% palladium hydroxide on carbon (800 mg) under an atmosphere of hydrogen for 2 h. The catalyst was removed by filtration through Celite and the filtrate concentrated to give the title compound as an orange oil: $^1$H NMR (CDCl$_3$) d 0.98 (t, J=7.3 Hz, 3 H), 1.47 (s, 9 H), 1.57 (m, 2 H), 2.40 (t, J=7.7 Hz, 2 H), 4.73 (s, 2 H), 5.91 (d, J=7.3 Hz, 1 H), 6.55 (d, J=7.3 Hz, 1 H).

Step G: 3-Benzylsulfonylamino-6-propyl-1-(t-butylmethylenecarboxy)-2-pyridinone

Benzylsulfonyl chloride (880 mg, 4.6 mmol) was added to a solution of 3-amino-6-propyl-1-(t-butylmethylenecarboxy)-2-pyridinone (1.1 g, 4.1 mmol) in pyridine (20 ml) at 0° C. and as the resulting solution was stirred a thick precipitate formed. After 1 h the reaction mixture was evaporated in vacuo to a thick paste. This was partitioned between methylene chloride and 10% potassium hydrogen sulfate solution. The organic layer was dried (Na$_2$SO$_4$) and evaporated in vacuo to give a red solid which was purified by flash chromatography (2:1:1 hexane/chloroform/ethyl acetate) to give the desired product as a mustard crystalline solid: $^1$H NMR (CDCl$_3$) d 1.03 (t, J=7.3 Hz, 3 H), 1.51 (s, 9 H), 1.63 (m, 2 H), 2.46 (t, J=7.7 Hz, 2 H), 4.32 (s, 2 H), 4.73 (s, 2 H), 5.99 (d, J=7.7 Hz, 1 H), 7.22–7.32 (m, 5 H), 7.35 (d, J=7.7 Hz, 1 H).

Step H: 3-Benzylsulfonylamino-6-propyl-1-methylenecarboxy-2-pyridinone

HCl gas was bubbled through a stirred suspension of 3-benzylsulfonylamino-6-propyl-1-(t-butylmethylenecarboxy)-2-pyridinone (1.1 g, 2.8 mmol) in ethyl acetate (20 ml) at 0° C. until a solution had formed which was saturated with HCl. After 4 h at room temperature the mixture was degassed with nitrogen and filtered to give the title compound as a pale pink solid: $^1$H NMR (CDCl$_3$) d 1.02 (t, J=7.3 Hz, 3 H), 1.63 (m, 2 H), 2.57 (t, J=7.7 Hz, 2 H), 4.44 (s, 2 H), 4.85 (s, 2 H), 6.11 (d, J=7.7 Hz, 1 H), 7.26–7.33 (m, 5 H), 7.34 (d, J=7.7 Hz, 1 H).

Step I: 1-Carboxymethyl-4-methyl-5-azidomethylimidazole

The title compound was prepared from 1-t-butoxycarbonylmethyl-4-methyl-5-azidomethylimidazole using the procedure described in EXAMPLE XXI, Step D. $^1$H NMR (CD$_3$OD) d 2.43 (s, 3 H), 4.61 (s, 2 H), 5.14 (s, 2 H), 8.97 (s, 1 H).

Step J: 1-t-Butylaminocarbonylmethyl-4-methyl-5-azidomethylimidazole

The title compound was prepared from 1-carboxymethyl-4-methyl-5-azidomethylimidazole and tert-butylamine using the procedure described in EXAMPLE I, Step A. $^1$H NMR (CDCl$_3$) d 1.32 (s, 9 H), 2.29 (s, 3 H), 4.31 (s, 2 H), 4.48 (s, 2 H), 5.25 (br s, 1 H), 7.47 (s, 1 H).

Step K: 1-t-Butylaminocarbonylmethyl-4-methyl-5-aminomethylimidazole

A solution of 1-t-butylaminocarbonylmethyl-4-methyl-5-azidomethylimidazole (1.27 g, 5.4 mmol) and 10% Pd/C (700 mg) in ethyl acetate (100 ml) was hydrogenated at atmospheric pressure for 5 h. The catalyst was removed by filtration through Celite and the solvents removed in vacuo to give the title compound. $^1$H NMR (CDCl$_3$) d 1.27 (s, 9 H), 2.23 (s, 3 H), 3.83 (s, 2 H), 4.50 (s, 2 H), 7.08 (br s, 1 H), 7.46 (s, 1 H).

Step L: 3-Benzylsulfonamino-6-propyl-1-(1-t-butylaminocarbonylmethyl-4-methyl-5-methylenecarboxamidomethylimidazolyl)-2-pyridinone The title compound was prepared from 3-benzylsulfonylamino-6-propyl-1-methylenecarboxy-2-pyridinone and 1-t-butylaminocarbonylmethyl-4-methyl-5-aminomethylimidazole essentially according to the procedure of EXAMPLE I, Step A: $^1$H NMR (CD$_3$OD) d 1.00 (t, J=7.4 Hz,3 H), 1.32 (s, 9 H),1.61 (m, 2 H), 2.38 (s, 3 H), 2.56 (t, J=7.7 Hz, 2 H), 4.41 (d, J=3.9 Hz, 2 H), 4.44 (s, 2 H), 4.72 (s, 2 H), 4.99 (s, 2 H), 6.13 (d, J=7.7 Hz, 1 H), 7.26–7.34 (m, 6 H), 8.74 (s, 1 H); MS (FAB) 571 (M+1)$^+$.

EXAMPLE XXXVII

Preparation of 3-(2-Tetrahydropyranylmethanesulfonylamino)-6-methyl-1-(1'-t-butoxycarbonylmethyl-4-methyl-5-methylenecarboxamidomethyl-imidazolyl)-2-pyridinone

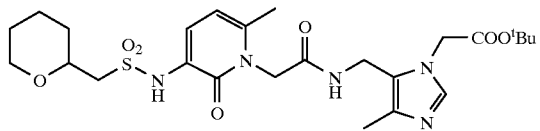

Step A: 2-Tetrahydropyranylmethanethioacetate

To a solution of 2-bromomethyltetrahydropyran (10.5 g, 59 mmol) in THF (100 ml) was added potassium thioacetate (7.35 g, 65 mmol). The resulting suspension was refluxed for 48 h. After cooling to room temperature, the solvents were removed in vacuo and the residue dissolved in chloroform and washed with water. The organics were dried over MgSO$_4$, filtered and the solvents removed in vacuo. The crude product was purified by chromatography (9:1 hexane/ethyl acetate). $^1$H NMR (CDCl$_3$) d 1.21–1.40 (m, 1 H), 1.45–1.60 (m, 3 H), 1.73 (br d, J=14 Hz, 1 H), 1.80–1.90 (m, 1 H), 2.35 (s, 3 H), 2.81–2.95 (m, 1 H), 3.01–3.15 (m, 1 H), 3.35–3.45 (m, 2 H), 3.95–4.07 (m, 1 H).

Step B: 2-Tetrahydropyranylmethanesulfonyl chloride

The title compound was prepared from 2-tetrahydropyranylmethanethioacetate using the procedure described in EXAMPLE XXI, Step B. $^1$H NMR (CDCl$_3$) d 1.35–1.50 (m, 1 H), 1.50–1.70 (m, 3 H), 1.75 (br d, J=14 Hz, 1 H), 1.83–1.95 (m, 1 H) 3.42–3.57 (m, 1 H), 3.70–3.80 (m, 1 H), 3.90–4.12 (m, 3 H).

Step C: 3-(2-Tetrahydropyranylmethanesulfonylamino)-6-methyl-1-(t-butylmethylenecarboxy)-2-pyridinone The title compound was prepared from 2-tetrahydropyranylmethanesulfonyl chloride and 3-amino-6-methyl-1-(t-butylmethylenecarboxy)-2-pyridinone using the procedure described in EXAMPLE XXI, Step C. $^1$H NMR (CDCl$_3$) d 1.25–1.48 (m, 4 H), 1.45 (s, 9 H), 1.62 (br d, J=14 Hz, 1 H), 1.78–1.85 (m, 1 H), 2.25 (s, 3 H), 3.00–3.10 (m, 1 H), 3.25–3.35 (m, 1 H), 3.35–3.45 (m, 1 H), 3.80–3.87 (m, 1 H), 3.87–3.95 (m, 1 H), 4.75 (s, 2 H), 6.05 (d, J=8 Hz, 1 H), 7.45 (d, J=8 Hz, 1 H) 7.49 (s, 1 H).

Step D: 3-(2-Tetrahydropyranylmethanesulfonylamino)-6-methyl-1-methylenecarboxy-2-pyridinone The title compound was prepared from 3-(2-tetrahydropyranylmethanesulfonylamino)-6-methyl-1-(t-butylmethylenecarboxy)-2-pyridinone using the procedure described in EXAMPLE XXI, Step D. $^1$H NMR (CD$_3$OD) d 1.25–1.58 (m, 4 H), 1.63 (br d, J=14 Hz, 1 H), 1.75–1.85 (m, 1 H), 2.32 (s, 3 H), 3.17–3.40 (m, 3 H), 3.75–3.90 (m, 2 H), 4.90 (s, 2 H), 6.22 (d, J=8 Hz, 1 H), 7.50 (d, J=7.5 Hz, 1 H).

Step E: 3-(2-Tetrahydropyranylmethanesulfonylamino)-6-methyl-1-(1'-t-butoxycarbonylmethyl-4-methyl-5-methylene-carboxamidomethylimidazolyl)-2-pyridinone The title compound was prepared from 3-(2-tetrahydropyranylmethanesulfonylamino)-6-methyl-1-methylenecarboxy-2-pyridinone and 1-t-butoxycarbonylmethyl-4-methyl-5-aminomethylimidazole using the procedure described in EXAMPLE I, Step A. $^1$H NMR (CD$_3$OD) d 1.20–1.58 (m, 4 H), 1.50 (s, 9 H), 1.65 (br d, J=14 Hz, 1 H), 1.72–1.87 (m, 1 H), 2.31 (s, 3 H), 2.40 (s, 3 H), 3.16–3.40 (m, 3 H), 3.75–3.87 (m, 2 H), 4.41 (s, 2 H), 4.75 (s, 2 H), 5.12 (s, 2 H), 6.22 (d, J=7.3 Hz, 1 H), 7.45 (d, J=7.5 Hz, 1 H), 8.80 (s, 1 H); MS (FAB) 552 (M+1)$^+$.

EXAMPLE XXXVIII

Preparation of 3-(2-Tetrahydropyranylmethanesulfonylamino)-6-methyl-1-(1'-t-butylaminocarbonylmethyl-4-methyl-5-methylenecarboxamidomethyl-imidazolyl)-2-pyridinone

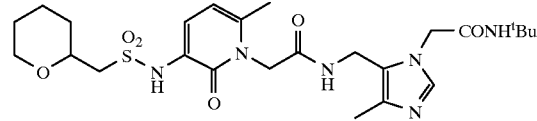

The title compound was prepared from 3-(2-tetrahydropyranylmethanesulfonylamino)-6-methyl-1-methylenecarboxy-2-pyridinone and 1-t-butylaminocarbonylmethyl-4-methyl-5-aminomethyl-imidazole using the procedure described in EXAMPLE I, Step A. $^1$H NMR (CD$_3$OD) d 1.20–1.40 (m, 2 H), 1.30 (s, 9 H), 1.40–1.60 (m, 2 H), 1.65 (br d, J=14 Hz, 1 H), 1.75–1.90 (m, 1 H), 2.33 (s, 3 H), 2.39 (s, 3 H), 3.15–3.40 (m, 3 H), 3.75–3.87 (m, 2 H), 4.40 (s, 2 H), 4.76 (s, 2 H), 5.00 (s, 2 H), 6.24 (d, J=7.6 Hz, 1H), 7.46 (d, J=7.6 Hz, 1 H), 7.95 (br s, 1 H), 8.70 (m, 1 H), 8.78 (s, 1 H) MS (FAB) 551 (M+1)$^+$.

EXAMPLE XXXIX

Preparation of 3-(2-Tetrahydropyranmethanesulfonylamino)-6-propyl-1-(1'-t-butylaminocarbonylmethyl)-4-methyl-5-methylenecarboxamidomethylimidazolyl)-2-pyridinone

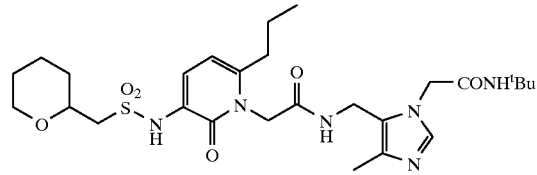

The title compound was prepared using the procedure described for Example XXXVI by substituting 2-tetrahydropyranmethane-sulfonyl chloride for benzylsulfonyl chloride in Step G. $^1$H NMR (CD$_3$OD) d 1.00 (t, J=7.2

Hz, 3 H), 1.34 (s, 9 H), 2.39 (s, 3 H), 2.58 (t, J=7.6 Hz, 2 H), 3.83 (d, J=10.5 Hz, 2 H), 4.39 (s, 2 H), 4.74 (s, 2 H), 5.01 (s, 2 H), 6.24 (d, J=7.6 Hz, 1H), 7.50 (d, J=7.6 Hz, 1 H), 8.78 (s, 1 H); MS (FAB) 579 (M+1)+.

EXAMPLE XL

Preparation of 3-Cyclohexylmethanesulfonylamino-6-methyl-1-(1'-t-butyl-aminocarbonylmethyl-4-methyl-5-methylenecarboxamidomethyl-imidazolyl)-2-pyridinone

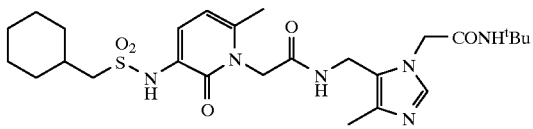

Step A: Sodium cyclohexylmethanethiosulfate

The title compound was prepared from bromomethylcyclohexane using the procedure described in EXAMPLE XXI, Step A. $^1$H NMR (CDCl$_3$) d 0.90–1.05 (m, 2 H), 1.15–1.39 (m, 3 H), 1.60–1.80 (m, 4 H), 1.85 (br d, J=12 Hz, 2 H) 2.95 (d, J=7 Hz, 2 H).

Step B: Cyclohexylmethanesulfonyl chloride

The title compound was prepared from sodium cyclohexylmethanethiosulfate using the procedure described in EXAMPLE XXI, Step B. $^1$H NMR (CDCl$_3$) d 1.10–1.42 (m, 5 H), 1.62–1.80 (m, 3 H), 1.97 (br d, J=12 Hz, 2 H), 2.15–2.30 (m, 1 H), 3.75 (d, J=6 Hz, 2 H).

Step C: 3-Cyclohexanemethylsulfonylamino-6-methyl-1-(t-butylmethylenecarboxy)-2-pyridinone The title compound was prepared from cyclohexylmethanesulfonyl chloride and 3-amino-6-methyl-1-(t-butylmethylenecarboxy)-2-pyridinone using the procedure described in EXAMPLE XXI, Step C. $^1$H NMR (CDCl$_3$) d 0.95–1.37 (m, 5 H), 1.45 (s, 9 H), 1.58–1.95 (m, 6 H), 2.27 (s, 3 H), 2.95 (d, J=7 Hz, 2 H), 4.77 (s, 2 H), 6.10 (d, J=8 Hz, 1 H), 7.20 (s, 1 H), 7.45 (d, J=8 Hz, 1 H).

Step D: 3-Cyclohexanemethylsulfonylamino-6-methyl-1-methylenecarboxy-2-pyridinone The title compound was prepared from 3-cyclohexanemethyl-sulfonylamino-6-methyl-1-(t-butylmethylenecarboxy)-2-pyridinone using the procedure described in EXAMPLE XXI, Step D. $^1$H NMR (CD$_3$OD) d 0.95–1.40 (m, 5 H), 1.60–1.75 (m, 3 H), 1.85–1.95 (m, 3 H), 2.35 (s, 3 H), 2.97 (d, J 6 Hz, 2 H), 4.90 (s, 2 H), 6.22 (d, J=8 Hz, 1 H), 7.43 (d, J=8 Hz, 1 H).

Step E: 3-Cyclohexylmethanesulfonylamino-6-methyl-1-(1'-t-butylaminocarbonylmethyl-4-methyl-5-methylenecarboxamidomethylimidazolyl)-2-pyrdinone The title compound was prepared from 3-cyclohexanemethyl-sulfonylamino-6-methyl-1-methylenecarboxy-2-pyridinone and 1-t-butyl-aminocarbonylmethyl-4-methyl-5-aminomethylimidazole using the procedure described in EXAMPLE I, Step A. $^1$H NMR (CD$_3$OD) d 0.95–1.42 (m, 5 H), 1.34 (s, 9 H), 1.60–1.75 (m, 3 H), 1.81–1.98 (m, 3 H), 2.33 (s, 3 H), 2.39 (s, 3 H), 3.00 (d, J=5.6 Hz, 2 H), 4.40 (s, 2 H), 4.74 (s, 2 H), 5.00 (s, 2 H) 6.24 (d, J=7.4 Hz, 1 H), 7.44 (d, J=7.6 Hz, 1 H), 7.95 (br s, 1 H), 8.75 (br m, 1 H), 8.78 (s, 1 H); MS (FAB) 549 (M+1)+.

EXAMPLE XLI

Preparation of 3-Pentanesulfonylamino-6-methyl-1-(1'-t-butoxycarbonylmethyl-4-methyl-5-methylenecarboxamidomethyl-imidazolyl)-2-pridinone

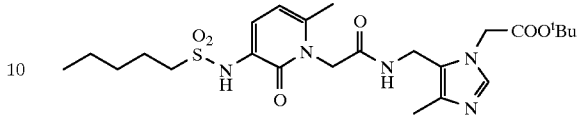

Step A: Pentanesulfonyl chloride

The title compound was prepared from 1-pentanethiol using the procedure described in EXAMPLE XXI, Step B. Ice water was used as the solvent instead of ice water/acetic acid. $^1$H NMR (CDCl$_3$) d 0.95 (t, J=7 Hz, 3 H), 1.32–1.45 (m, 4 H), 1.95–2.10 (m, 2 H), 3.60–3.70 (m, 2 H).

Step B: 3-Pentanesulfonylamino-6-methyl-1-(t-butylmethylenecarboxy)-2-pyridinone The title compound was prepared from pentanesulfonyl chloride and 3-amino-6-methyl-1-(t-butylmethylenecarboxy)-2-pyridinone using the procedure described in EXAMPLE XXI, Step C. It was purified by chromatography (2:1 hexane/ethyl acetate). $^1$H NMR (CDCl$_3$) d 0.85 (t, J=7 Hz, 3 H), 1.20–1.40 (m, 4H), 1.45 (s, 9 H), 1.74–1.86 (m, 2 H), 2.25 (s, 3 H), 2.98–3.05 (m, 2 H), 4.75 (s, 2 H), 6.08 (d, J=8 Hz, 1 H), 7.20 (s, 1 H), 7.45 (d, J=8 Hz, 1 H).

Step C: 3-Pentanesulfonylamino-6-methyl-1-methylenecarboxy-2-pyridinone

The title compound was prepared from 3-pentanesulfonylamino-6-methyl-1-(t-butylmethylenecarboxy)-2-pyridinone using the procedure described in EXAMPLE XXI, Step D. $^1$H NMR (CD$_3$OD) d 0.85 (t, J=7 Hz, 3,H), 1.22–1.40 (m, 4 H), 1.70–1.82 (m, 2 H), 2.35 (s, 3 H), 3.02–3.12 (m, 2 H), 4.87 (s, 2 H), 6.25 (d, J=8 Hz, 1 H), 7.47 (d, J=8 Hz, 1 H).

Step D: 3-Pentanesulfonylamino-6-methyl-1-(1'-t-butoxycarbonylmethyl-4-methyl-5-methylenecarboxamidomethylimidazolyl)-2-pyridinone The title compound was prepared from 3-pentanesulfonylamino-6-methyl-1-methylenecarboxy-2-pyridinone and 1-t-butoxycarbonylmethyl-4-methyl-5-aminomethylimidazole using the procedure described in EXAMPLE I, Step A. $^1$H NMR (CD$_3$OD) d 0.89 (t, J=6.8 Hz, 3 H), 1.25–1.40 (m, 4 H), 1.49 (s, 9 H), 1.70–1.81 (m, 2 H), 2.31 (s, 3 H), 2.40 (s, 3 H), 3.08–3.18 (m, 2 H), 4.41 (s, 2 H), 4.76 (s, 2 H), 5.11 (s, 2 H), 6.23 (d, J=7.6 Hz, 1 H), 7.45 (d, J=7.6 Hz, 1 H), 8.81 (s, 1 H); MS (FAB) 524 (M+1)+.

EXAMPLE XLII

Preparation of 3-(2-Phenethylamino)-6-methyl-1-(1'-t-butoxycarbonylmethyl-4-methyl-5-methylenecarboxamidomethylimidazolyl)pyrazinone

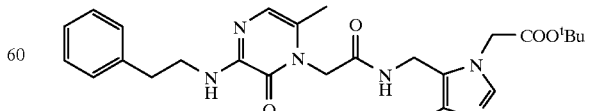

Step A: N-(1-Cyanoethyl)glycine benzyl ester hydrochloride

TMSCN (4.27 ml, 32 mmol) was added cautiously (reaction is exothermic) to a stirred solution of glycine benzyl ester (5.3 g, 32 mmol, prepared from the HCl salt by partitioning between EtOAc and NaHCO$_3$ solution) and acetaldehyde (1.8 ml, 32 mmol) in methylene chloride (11 ml). After 4 h the volatiles were removed in vacuo and the residue was taken up in EtOAc and was washed with brine, dried (Na$_2$SO$_4$) and evaporated in vacuo to an oil. The oil was redissolved in EtOAc and 9.9 M HCl in EtOH (38.4 mmol) was added to give a crystalline precipitate which was isolated by filtration and washing with EtOAc, to give the title compound: $^1$H NMR (CDCl$_3$) d 1.49 (d, J=7.1 Hz, 3 H, CH$_3$), 3.54 (d, J=17.3 Hz, 1 H, CH$_A$H$_B$), 3.64 (d, J=17.3 Hz, 1 H, CH$_A$H$_B$), 3.74 (q, J=7.0 Hz, 1 H, a-CH), 5.18 (s, 2 H, CH$_2$O),7.36 (s, 5 H, Ph).

Step B: 1-Benzyloxycarbonylmethyl-3,5-dichloro-6-methylpyrazinone

A stirred mixture of oxalyl chloride (9.3 ml, 107 mmol) and N-(1-cyanoethyl)glycine benzyl ester hydrochloride (6.8 g, 26.7 mmol) in 1,2-dichlorobenzene (25 ml) was heated to 100° C. for 15 h. The excess reagent was evaporated in vacuo and the residue was purified by flash chromatography (eluting first with hexanes to remove the dichlorobenzene, then with 3:2 hexanes/ethyl acetate) to give a solid which was triturated with 1:1 hexanes/ethyl acetate to give the title compound as a pale green crystalline solid: $^1$H NMR (CDCl$_3$) d 2.35 (s, 3 H, CH$_3$), 4.88 (s, 2 H, CH$_2$), 5.24 (s, 2 H, CH$_2$), 7.38 (m, 5 H, Ph).

Step C: 3-(2-Phenethylamino)-5-chloro-6-methyl-1-(benzyloxycarbonylmethyl)pyrazinone 2-Phenethylamine (0.38 ml, 3.0 mmol) was added to a stirred mixture of 1-benzyloxycarbonylmethyl-3,5-dichloro-6-methylpyrazinone (327 mg, 1.00 mmol) in EtOAc (2 ml) and the resulting mixture was heated to reflux under argon. After 2 h the reaction was cooled, diluted with EtOAc (the product is sparingly soluble), washed with 10% citric acid solution and brine, dried (Na$_2$SO$_4$) and evaporated in vacuo to give the title compound as a crystalline solid. $^1$H NMR (CDCl$_3$) d 2.21 (s, 3 H, CH$_3$), 2.93 (t, J=7.1 Hz, 2 H, PhCH$_2$), 3.67 (q, J=7.1 Hz, 2 H, CH$_2$NH), 4.79 (s, 2 H, CH$_2$),5.21 (s, 2 H, CH$_2$), 6.10 (br t, 1 H), 7.20–7.39 (m, 10 H, 2 Ph).

Step D: 3-(2-Phenethylamino)-5-chloro-6-methyl-1-(methylenecarboxy)pyrazinone

Water (1 ml) was added to a stirred solution of 3-(2-phenethylamino)-5-chloro-6-methyl-1-(benzyloxycarbonyl-methyl)pyrazinone (436 mg) in 1:1 THF/MeOH (6 ml) and LiOH.H$_2$O was added to the resulting mixture. After 2 h, the reaction mixture was diluted with water and washed with EtOAc. The aqueous layer was acidified with 10% KHSO$_4$ solution to give a cloudy mixture which was extracted with methylene chloride. The organic layer was dried (Na$_2$SO$_4$) and evaporated in vacuo to give the title compound as a crystalline solid: $^1$H NMR (DMSO-d6) d 2.19 (s, 3 H, Me), 2.84 (t, J=7.0 Hz, 2 H, PhCH$_2$), 3.45 (q, J=7.0 Hz, 2 H, CH$_2$NH), 4.70 (s, 2 H, CH$_2$CO$_2$), 7.18–7.31 (m, 5 H, Ph), 7.46 (br s, 1 H, NH).

Step E: 3-(2-Phenethylamino)-6-methyl-1-methylenecarboxyprazinone 3-(2-Phenethylamino)-5-chloro-6-methyl-1-(methylenecarboxy)pyrazinone (13.4 g, 41.6 mmol) was added to a stirred solution of potassium hydroxide (7.28 g, 110 mmol, assuming 15% water in the pellets) in water (600 ml). After degassing the resulting solution with argon, 10% Pd/C (6.3 g) was added and the mixture then stirred under a balloon of hydrogen. After 16 h, HPLC analysis showed that 1% of the starting material remained. The mixture was filtered through Celite and the filtrate was adjusted to pH 2 with 3N KHSO$_4$ solution. The resulting precipitate was collected by filtration and washed with water. Drying for 16 h at 0.5 mm Hg gave the title compound as a crystalline solid: $^1$H NMR (DMSO-d6) d 2.11 (s, 3 H, Me), 2.87 (t, J=7.6 Hz, 2 H, PhCH$_2$), 3.53 (br s, 2 H, CH$_2$NH), 4.68 (s, 2 H, CH$_2$CO$_2$), 6.68 (s, 1 H, pyrazinone H-5), 7.20–7.31 (m, 5 H, Ph), 8.16 (br s, 1 H, NH).

Step F: 3-(2-Phenethylamino)-6-methyl-1-(1'-t-butoxycarbonylmethyl-4-methyl-5-methylenecarboxamido-methylimidazolyl)-pyrazinone The title compound was prepared from 3-(2-phenethylamino)-6-methyl-1-methylenecarboxypyrazinone and 1-t-butoxycarbonylmethyl-4-methyl-5-aminomethylimidazole essentially according to the procedure of EXAMPLE I, Step A: $^1$H NMR (CD$_3$OD) d 1.44 (s, 9 H), 2.18 (s, 3 H), 2.19 (s, 3 H), 2.92 (t, J=7.1 Hz, 2 H), 3.60 (m, 2 H), 4.33 (d, J=5.5 Hz, 2 H), 4.55 (d, J=10.8 Hz, 4 H), 5.93 (t, J=5.7 Hz, 1 H), 6.73 (s, 1 H), 7.2 (m, 1 H); MS (FAB) 495 (M+1)$^+$.

EXAMPLE XLIII

Preparation of 3-(2-Phenethylamino)-6-methyl-1-(1'-t-butylaminocarbonylmethyl-4-methyl-5-methylenecarboxamidomethylimidazolyl)pyrazinone

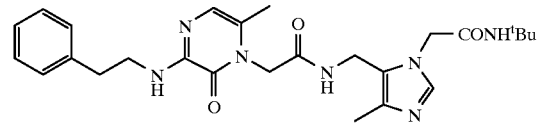

Step A: 3-(2-Phenethylamino)-6-methyl-1-(1-carboxymethyl-4-methyl-5-methylenecarboxamido-methylimidazolyl)pyrazinone The title compound was prepared from 3-(2-phenethylamino)-6-methyl-1-(1'-t-butoxycarbonyl-methyl-4-methyl-5-methylenecarbox-amidomethylimidazolyl) pyrazinone essentially according to the procedure of EXAMPLE XXI, Step D: $^1$H NMR (CD$_3$OD) d 2.16 (s, 3 H), 2.41 (s, 3 H), 2.99 (t, J=7.1 Hz, 2 H), 3.67 (t, J=7.1 Hz, 2 H), 4.47 (m, 2 H), 4.68 (s, 2 H), 5.15 (s, 2 H), 6.56 (s, 1 H), 7.21–7.33 (m, 5 H), 8.84 (s, 1 H).

Step B: 3-(2-Phenethylamino)-6-methyl-1-(1'-t-butylaminocarbonylmethyl-4-methyl-5-methylenecarbox-amidomethyl-imidazolyl)pyrazinone The title compound was prepared from 3-(2-phenethylamino)-6-methyl-1-(1-carboxymethyl-4-methyl-5-methylenecarboxamidomethyl-imidazolyl)pyrazinone and t-butylamine essentially according to the procedure of EXAMPLE I, Step A: $^1$H NMR (CD$_3$OD) d 1.36 (s, 9 H), 2.17 (s, 3 H), 2.39 (s, 3 H), 2.98 (t, J=7.4 Hz, 2 H), 3.60 (t, J=7.4 Hz, 2 H), 4.42 (m, 2 H), 4.70 (s, 2 H), 4.99 (s, 2 H), 6.59 (s, 1 H), 7.21–7.33 (m, 4 H), 7.97 (br s, 1 H), 8.78 (s, 1 H); MS (FAB) 495 (M+1)$^+$.

EXAMPLE XLIV

Preparation of 3-(2-Pyridylethylamino)-6-methyl-1-(1'-t-butoxycarbonylmethyl-4-methyl-5-methylenecarboxamidomethylimidazolyl)pyrazinone

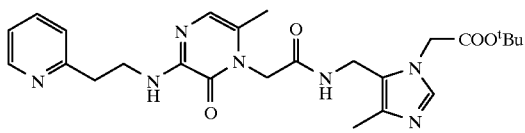

The title compound was prepared according to the procedure described for EXAMPLE XLII by substituting 2-(2-aminoethyl)pyridine for 2-phenethylamine in Step C: $^1$H NMR (CD$_3$OD) d 1.45 (s, 9 H), 2.12 (s, 3 H), 2.20 (s, 3 H), 3.08 (t, J=7.0 Hz, 2 H), 3.69 (t, J=7.0 Hz, 2 H), 4.32 (s, 2 H), 4.62 (s, 2 H), 4.79 (s, 2 H); 6.66 (s, 1 H), 7.25 (m, 1 H), 7.35 (d, J=4.0 Hz, 1 H), 7.52 (s, 1 H), 7.74 (t, J=7.5 Hz, 1 H), 8.44 (d, J=4.0 Hz, 1 H); MS (FAB) 495 (M+1)$^+$.

EXAMPLE XLV

Preparation of 3-(2-Pyridylethylamino)-6-methyl-1-(1'-t-butylaminocarbonylmethyl-4-methyl-5-methylenecarboxamidomethylimidazolyl)pyrazinone

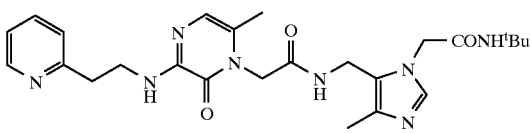

The title compound was prepared according to the procedure described for EXAMPLE XLIV by substituting 1-t-butylmethylamino-carbonylmethyl-4-methyl-5-aminomethylimidazole for 1-t-butoxycarbonyl-methyl-4-methyl-5-aminomethyliniidazole in Step F: $^1$H NMR (CD$_3$OD) d 1.35 (s, 9 H), 2.15 (s, 3 H), 2.38 (s, 3 H), 3.82 (t, J=6.8 Hz, 2 H), 3.82 (t, J=6.8 Hz, 2 H), 4.41 (d, J=3.7 Hz, 2 H), 4.69 (s, 2 H), 4.87 (s, 2 H), 4.99 (s, 2 H), 6.66 (s, 1 H), 7.77 (t, J=6.50 Hz, 1 H), 7.85 (d, J=8.1 Hz, 1 H), 7.98 (s, 1 H), 8.68 (d, J=5.7 Hz, 1 H), 8.78 (s, 1 H); MS (FAB) 495 (M+1)$^+$.

EXAMPLE XLVI

Preparation of 3-(2-Phenethylamino)-6-methyl-1-(1'-t-butylmethylaminocarbonylmethyl-4-methyl-5-methylenecarboxamidomethylimidazolyl)pyrazinone

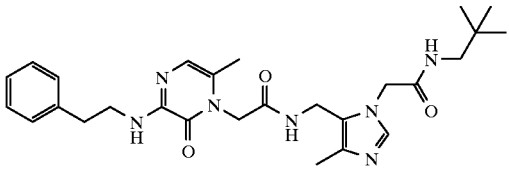

The title compound was prepared according to the procedure described for EXAMPLE XLIII by substituting 1-t-butylmethylamino-carbonylmethyl-4-methyl-5-aminomethylimidazole for 1-t-butoxycarbonyl-methyl-4-methyl-5-aminomethylimidazole in Step F: $^1$H NMR (CD$_3$OD) d 0.93 (s, 9 H), 2.17 (s, 3 H), 2.39 (s, 3 H), 2.99 (t, J=7.5 Hz, 2 H), 3.07, (d, J=6.1 Hz, 2 H), 3.68 (t, J=7.5 Hz, 2 H), 4.43 (s, 2 H), 4.71 (s, 2 H), 5.12 (s, 2 H), 6.56 (s, 1 H), 7.22–7.34 (m, 6 H), 8.34 (br t, 1 H), 8.82 (s, 1 H); MS (FAB) 508 (M+1)$^+$.

EXAMPLE XLVII

Preparation of 3-(2-Phenethylamino)-6-methyl-1-[1'-(2,2,2-trifluoroethylaminocarbonylmethyl)-4-methyl-5-methylenecarboxamidomethylimidazolyl]-pyrazinone

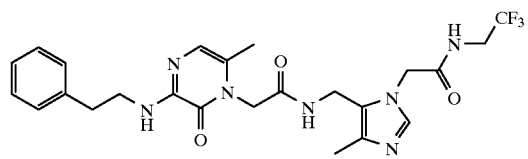

The title compound was prepared according to the procedure described for EXAMPLE XLIII by substituting 1-(2,2,2-trifluoroethyl-aminocarbonylmethyl)-4-methyl-5-aminomethylimidazole (prepared according to the procedure for EXAMPLE XXIX, Steps A to C by substituting 2,2,2-trifluoroethylamine hydrochloride for t-butylmethylamine in Step B) for 1-t-butoxycarbonylmethyl-4-methyl-5-aminomethylimidazole in Step F: $^1$H NMR (CD$_3$OD) d 2.16 (s, 3 H), 2.41 (s, 3 H), 2.98 (t, J=7.4 Hz, 2 H), 3.65 (t, J=7.4 Hz, 2 H), 4.43 (s, 2 H), 4.68 (s, 2 H), 5.17 (s, 2 H), 6.59 (s, 1 H), 7.23–7.33 (m, 4 H), 8.83 (s, 1 H); MS (FAB) 520 (M+1)$^+$.

EXAMPLE XLVIII

Preparation of 3-(2-Phenethylamino)-6-methyl-1-[1'-(3-piperidineamino)carbonylmethyl]-4-methyl-5-methylenecarboxamido-methylimidazolyl]-pyrazinone

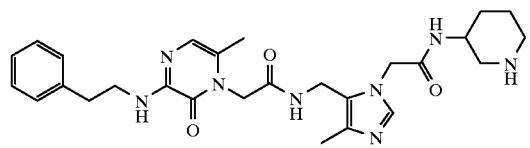

Step A: 3-Hydroxy-N-t-butoxycarbonylpiperidine

Di-t-butyldicarbonate (21 g, 96 mmol) was added to a mixture of 3-hyroxypiperidine hydrochloride (12 g, 87 mmol) and triethylamine (24.5 ml, 176 mmol) in methylene chloride (500 ml) at 0° C. After stirring for 2 h, the reaction mixture was washed well with water and dried (MgSO$_4$). Concentration gave the title compound. $^1$H NMR (CDCl$_3$) d 1.46 (s, 9 H), 1.60–1.89 (m, 4 H), 3.04–3.16 (m, 2 H), 3.52 (br s, 1 H), 3.73 (m, 2 H).

Step B: 3-Methanesulfonyloxy-N-t-butoxycarbonylpiperidine

Methanesulfonic anhydride (996 mg, 5.72 mmol) was added to a mixture of 3-hydroxy-N-t-butoxycarbonylpiperidine (959 mg, 4.76 mmol) and triethylamine (0.86 ml, 6.19 mmol) in methylene chloride (30 ml) at 0° C. After stirring for 1 h, the reaction mixture was washed with saturated NaHCO3 and dried (Na$_2$SO$_4$). Concentration gave the title compound. $^1$H NMR (CDCl$_3$) d 1.46 (s, 9 H), 1.77–2.17 (m, 4 H), 3.05 (s, 3 H), 3.14–3.49 (m, 2 H), 3.62 (m, 2 H), 4.72 (br s, 1 H).

Step C: 3-Azido-N-t-butoxycarbonylpiperidine

Lithium azide (1.35 g, 27.6 mmol) was added to a solution of 3-methanesulfonyloxy-N-t-butoxycarbonylpiperidine (1.54 g, 5.51 mmol) in DMF (20 ml) and the resulting mixture heated at 60° C. for 48 h. Removal of the solvent in vacuo and chromatographic purification (3:1 hexane/ethyl acetate) of the residue afforded the title compound. $^1$H NMR (CDCl$_3$) d 1.46 (s, 9 H), 1.75 (m, 2 H), 1.96 (m, 2 H), 3.13 (br s, 1 H), 3.46 (m, 2 H), 3.57 (m, 2 H).

Step D: 3-Amino-N-t-butoxycarbonylpiperidine

A solution of 3-azido-N-t-butoxycarbonylpiperidine (850 mg) in ethyl acetate (50 ml) was hydrogenated in the presence of 10% Pd/C (550 mg) at atmospheric pressure for 2.5 h. The reaction mixture was then filtered through Celite and the filtrate concentrated in vacuo to give the title compound. $^1$H NMR (CDCl$_3$) d 1.46 (s, 9 H), 1.66–2.05 (m, 4 H), 2.57 (br s, 1 H), 2.78 (m, 4 H), 3.80 (br d, 2 H).

Step E: 1-[(N-t-butoxycarbonyl-3-piperidineamino)carbonyl-methyl]-4-methyl-5-azidomethylimidazole The title compound was prepared from 1-carboxymethyl-4-methyl-5-azidomethylimidazole and 3-amino-N-t-butoxycarbonylpiperidine using the procedure described in EXAMPLE I, Step A. $^1$H NMR (CDCl$_3$) d 1.45 (s, 9 H), 1.53 (br m, 2 H), 1.63 (m, 1 H), 1.80 (br m, 1 H), 2.28 (s, 3 H), 3.23–3.49 (br m, 4 H), 3.95 (br s, 1 H), 4.32 (dd, J=14.6, 21.4 Hz, 2 H), 4.57 (s, 2 H), 7.47 (s, 1 H).

Step F: 1-[(N-t-butoxycarbonyl-3-piperidineamino)carbonyl-methyl]-4-methyl-5-aminomethylimidazole A solution of 1-[(N-t-butoxycarbonyl-3-piperidineamino)carbonylmethyl]-4-methyl-5-azidomethylimidazole (3.77 g) in ethanol (100 ml) was hydrogenated in the presence of 20% Pd(OH)$_2$/C (850 mg) at atmospheric pressure for 5 h. The reaction mixture was then filtered through Celite and the filtrate concentrated in vacuo to give the title compound.

Step G: 3-(2-Phenethylamino)-6-methyl-1-[1'-(N-t-butoxycarbonyl-3-piperidineamino)carbonylmethyl]-4-methyl-5-methylenecarboxamidomethylimidazolyl]pyrazinone The title compound was prepared from 3-(2-phenethylamino)-6-methyl-1-methylenecarboxypyrazinone and 1-[(N-t-butoxycarbonyl-3-piperidineamino)carbonylmethyl]-4-methyl-5-aminomethylimidazole using the procedure described in EXAMPLE I, Step A.

Step H: 3-(2-Phenethylamino)-6-methyl-1-[1'-(3-piperidineamino)carbonylmethyl]-4-methyl-5-methylenecarboxamidomethylimidazolyl]pyrazinone The title compound was prepared from 3-(2-Phenethylamino)-6-methyl-1-[1'-(N-t-butoxycarbonyl-3-piperidineamino)carbonylmethyl]-4-methyl-5-methylenecarboxamidomethylimidazolyl]pyrazinone using the procedure described in EXAMPLE XXI, Step D. $^1$H NMR (CD$_3$OD) d 1.63–2.04 (m, 4 H), 2.16 (s, 3 H), 2.40 (s, 3 H), 2.99 (m, 4 H), 3.30 (m, 2 H), 3.66 (m, 2 H), 4.05 (br s, 1 H), 4.44 (m, 2 H), 4.68 (s, 2 H), 5.12 (m, 2 H), 6.59 (s, 1 H), 7.20–7.32 (m, 5 H), 8.81 (s, 1 H); MS (FAB) 521 (M+1)$^+$.

EXAMPLE XLIX

Tablet Preparation

Tablets containing 100.0, 200.0, and 300.0 mg, respectively, of 3-Benzylsulfonylamino-6-methyl-1-[1-(2-hydroxyethylaminocarbonylmethyl)-4-methyl-5-methylenecarboxamidomethylimidazolyl]-2-pyridinone (example XXXIII) active compound are prepared as illustrated below:

| Ingredient | Amount-mg | | |
|---|---|---|---|
| Active compound | 100.0 | 200.0 | 300.0 |
| Microcrystalline cellulose | 160.0 | 150.0 | 200.0 |
| Modified food corn starch | 20.0 | | 15.0 | 10.0 |
| Magnesium stearate | 1.5 | | 1.0 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 100.0, 200.0, and 300.0 mg, respectively, of active ingredient per tablet.

EXAMPLE L

An intravenous dosage form of the above-indicated active compound is prepared as follows:

| | |
|---|---|
| Active compound | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed is:

1. A compound having the formula

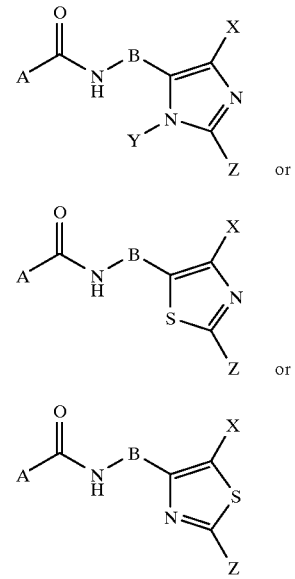

and pharmaceutically acceptable salts thereof, wherein
B is selected from the group consisting of:
—CH$_2$CH=CH—,
—CH$_2$CH$_2$CH$_2$—,
—CH$_2$C≡C—, and
—CH$_2$—;
X is H, —CH$_3$, or —Cl Z is H, or —NH₂, and Y is selected from the group consisting of hydrogen,

—CH₂COOC(CH₃)₃,

—CH₂COOH,

—CH₂CONHC(CH₃)₃,

—CH₂CONHCH₂CH₃,

—CH₂CONH—△,

—CH₂CONHCH₂—△,

—CH₂CONH—[piperidine-3-yl, NH],

—CH₂CONH—[piperidine-4-yl, NH],

—CH₂CONHCH₂—[pyridine],

—CH₂CONHC(CH₃)₂CH₂CH₃,

—CH₂CONHCH₂C(CH₃)₃,

—CH₂CONHCH₂CF₃,

—CH₂CON[morpholine],

—CH₂CON[azetidine]—OH,

—CH₂CON[azetidine]—NH₂,

—CH₂CONHCH₂CH₂OH,

—CH₂CONHCH₂CH₂NH₂,

—CH₂CONHC(CH₃)₂CH₂NH₂,

—CH₂CONHCH₂C(CH₃)₂NH₂,

—CH₂COOC(CH₃)₃, and A is selected from the group consisting of

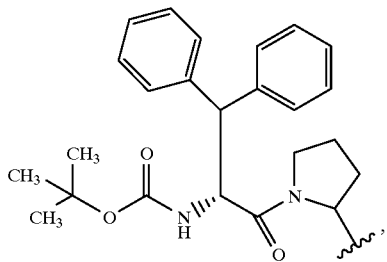

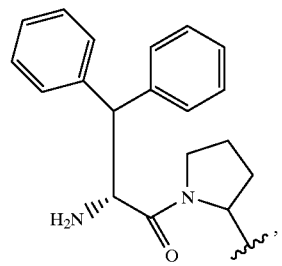

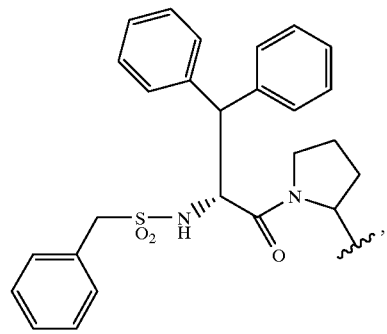

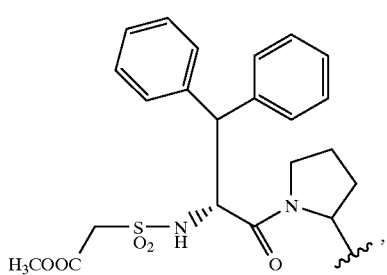

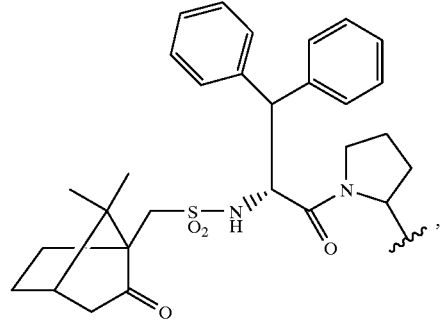

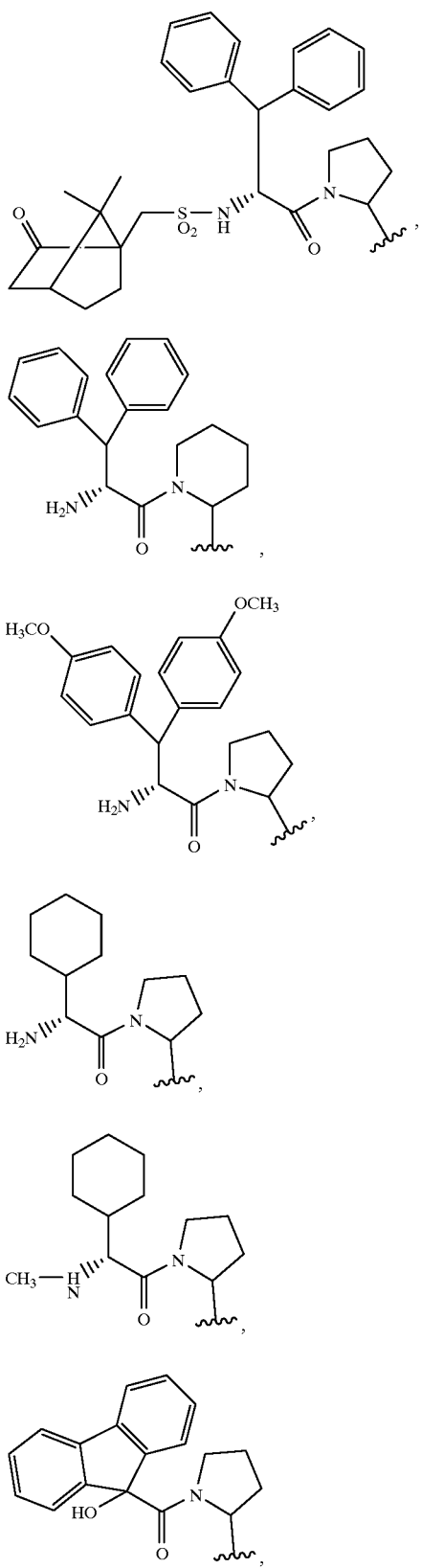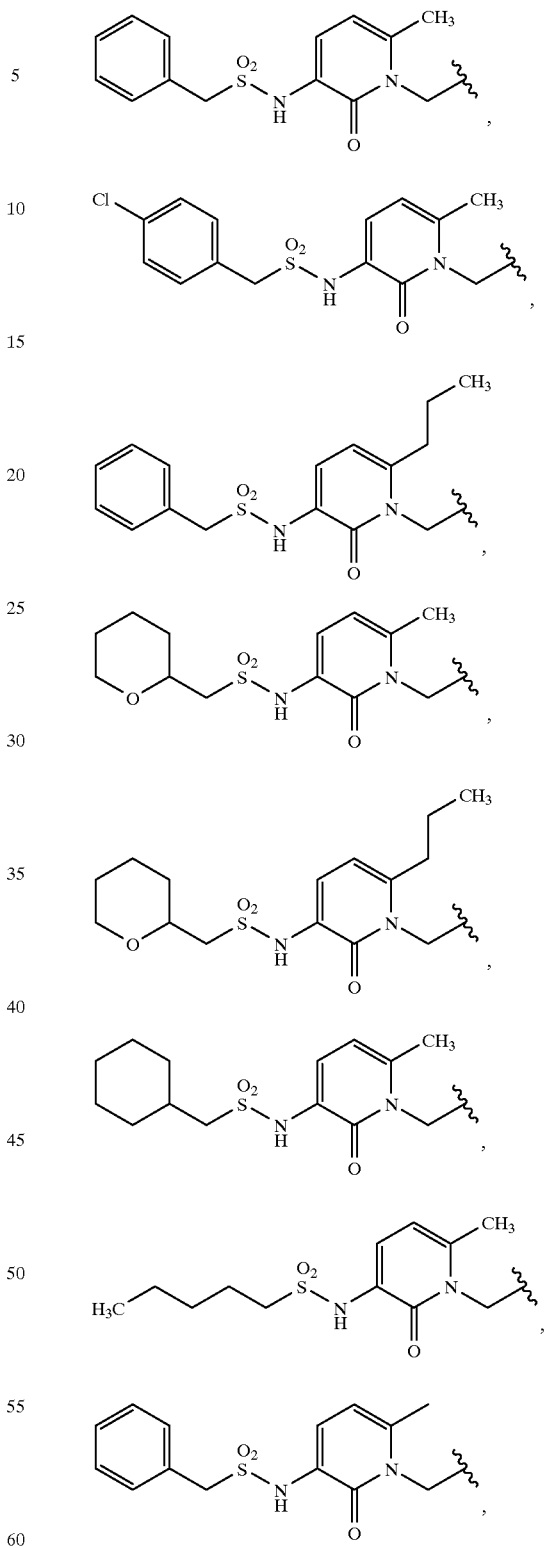

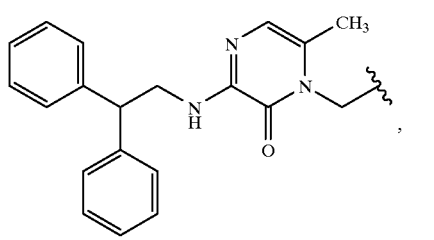
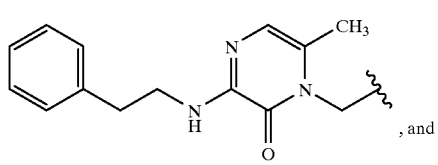
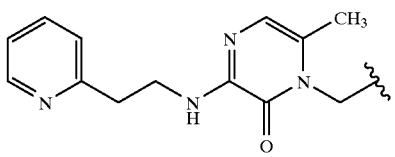
2. The compound of claim 1 selected from the group consisting of:
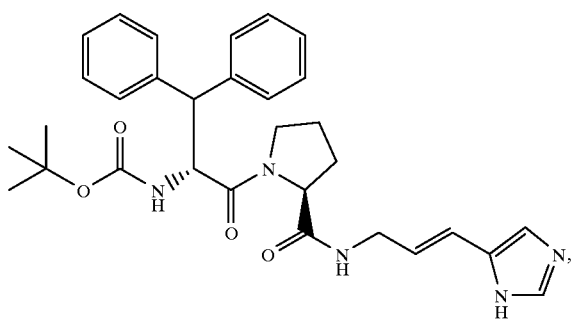
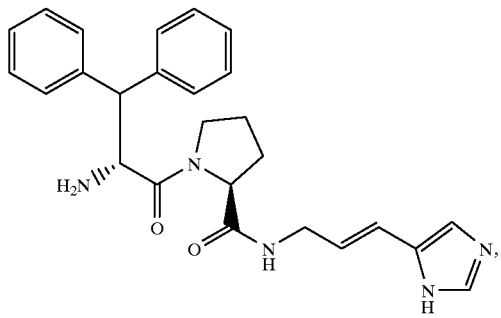
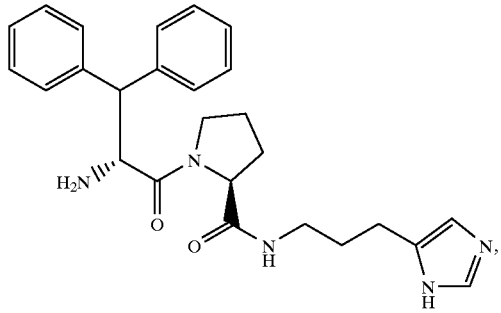

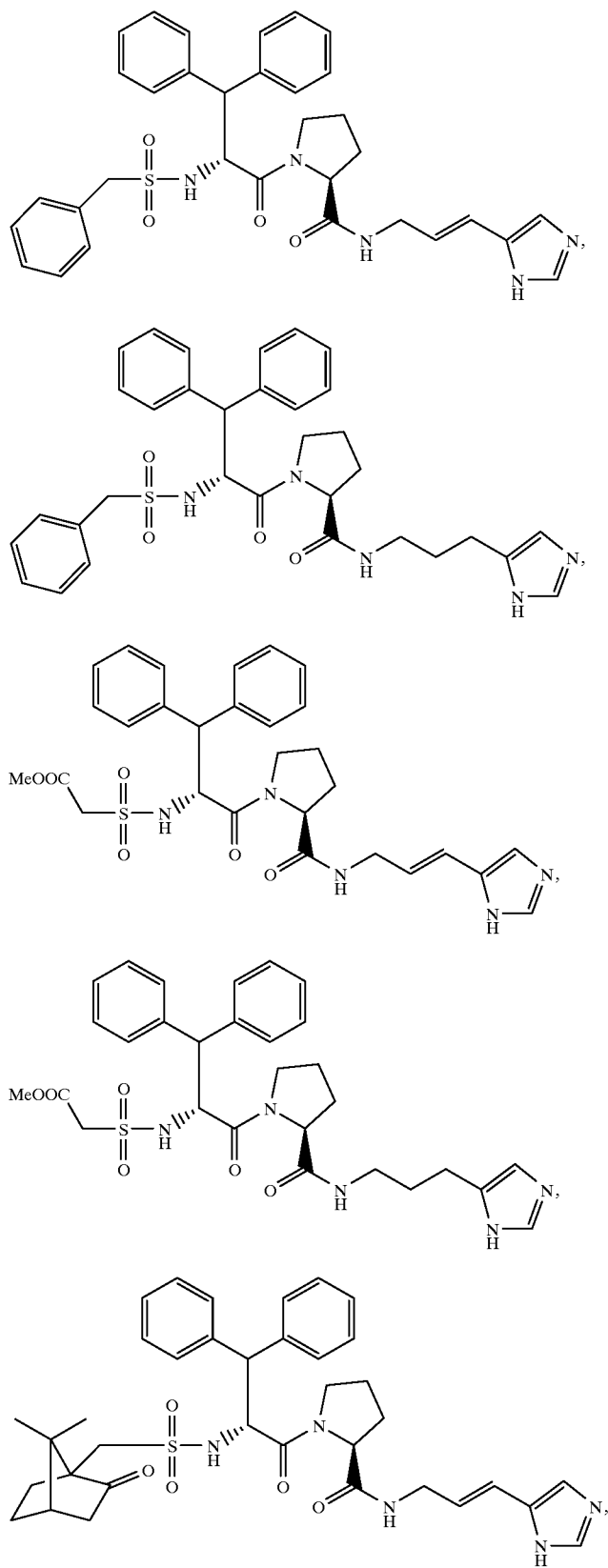

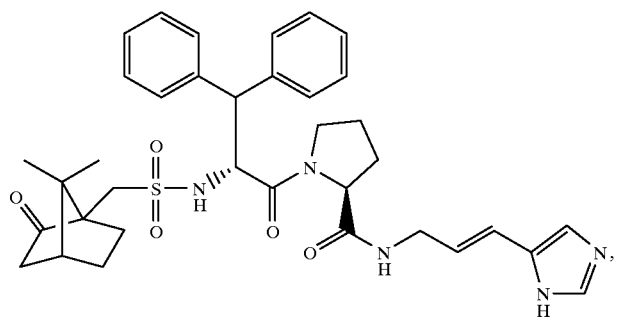
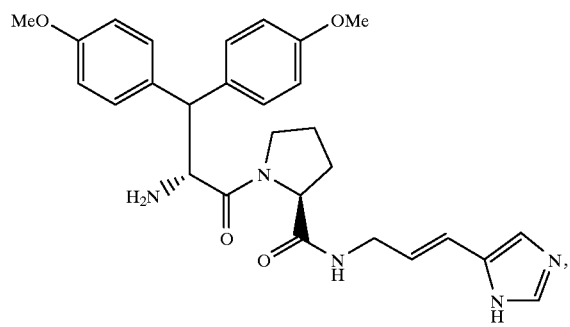
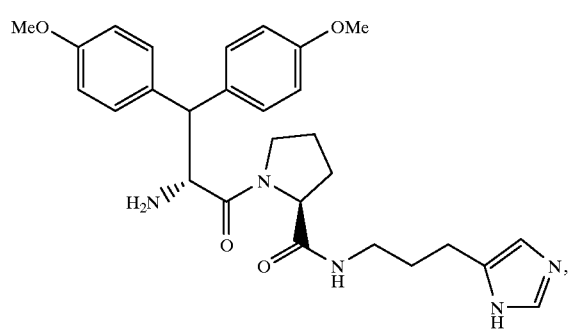
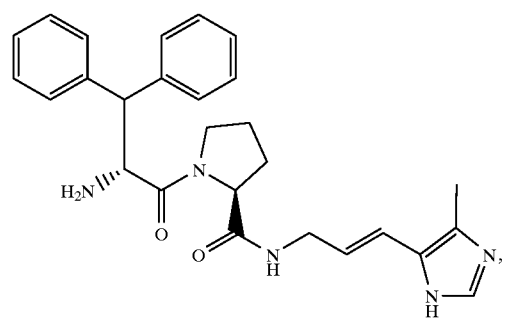
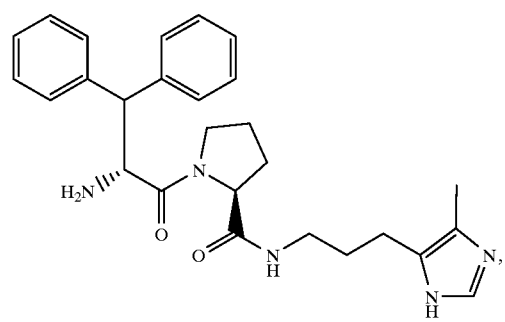

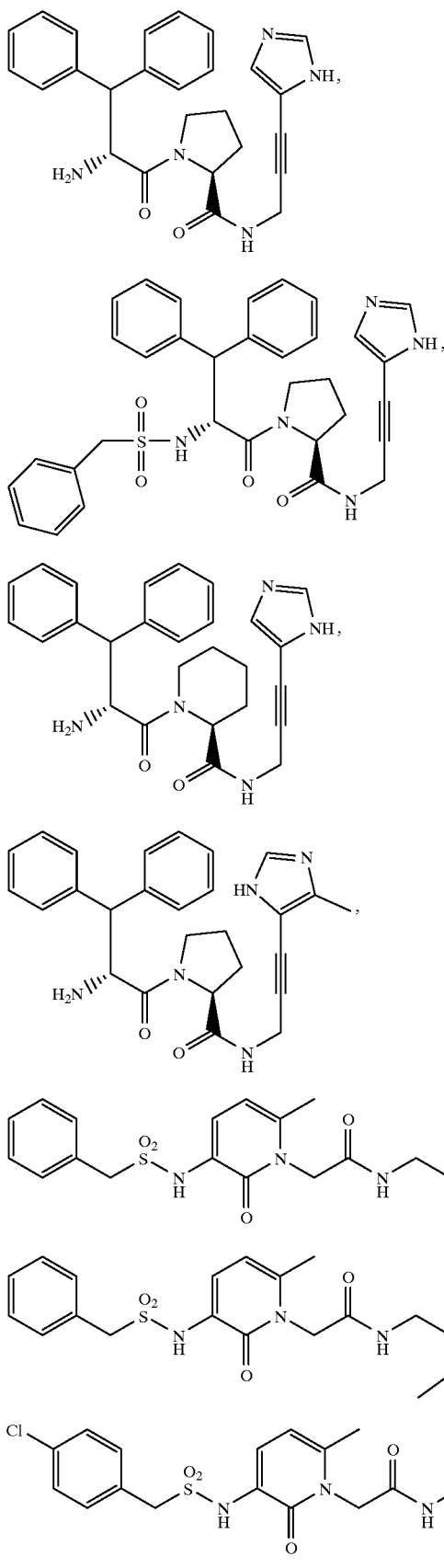

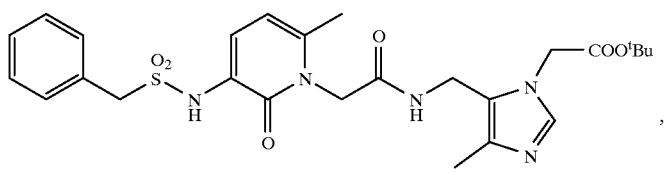,
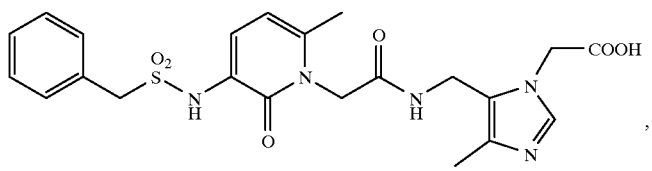,
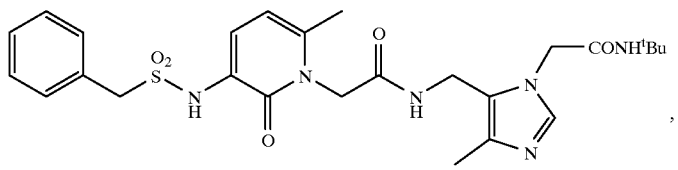,
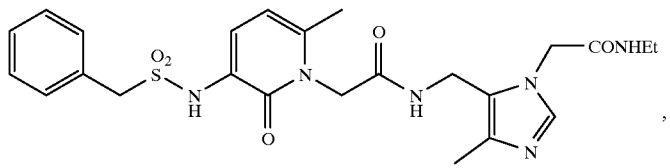,
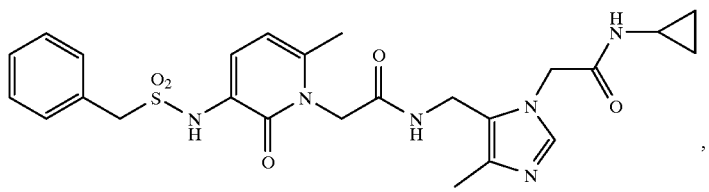,
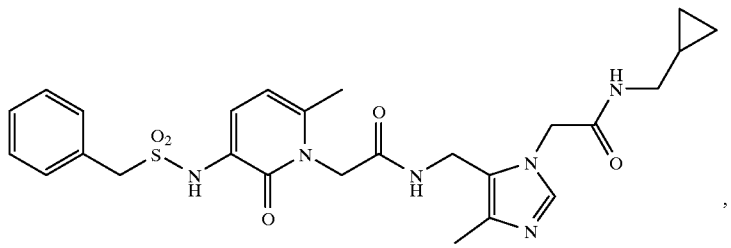,
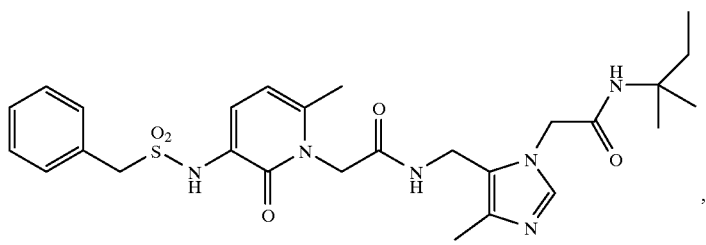,
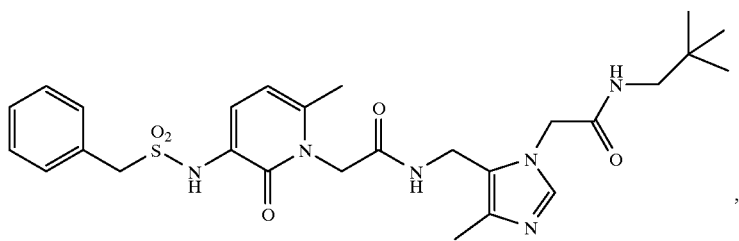,

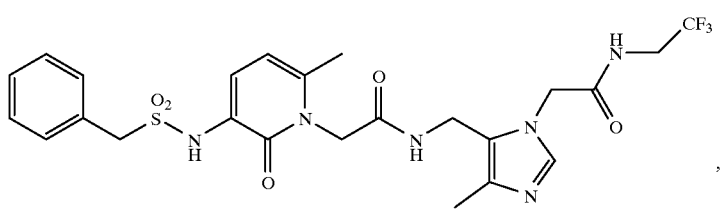,
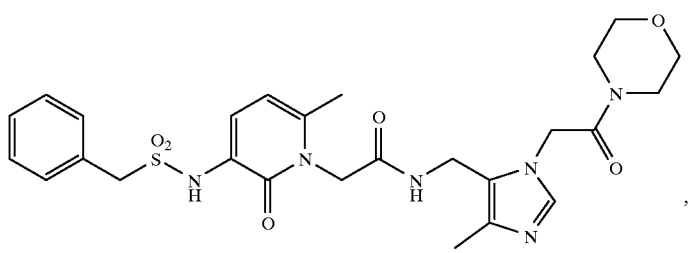,
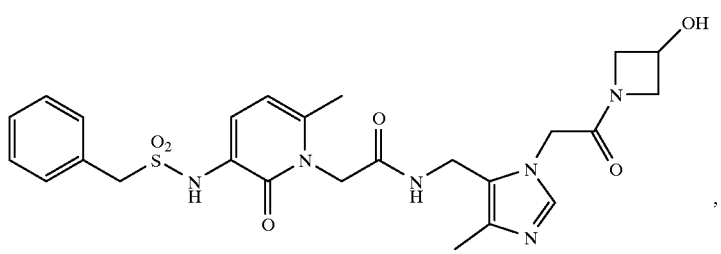,
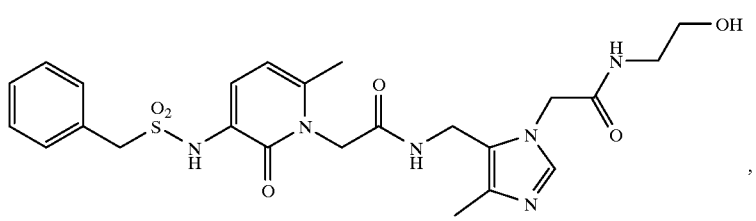,
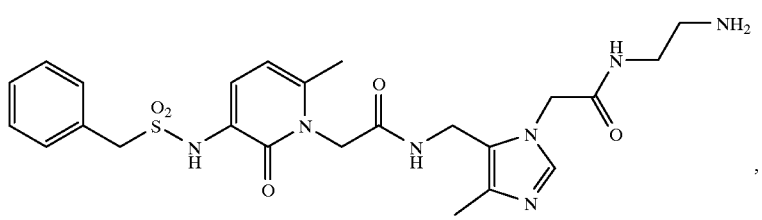,
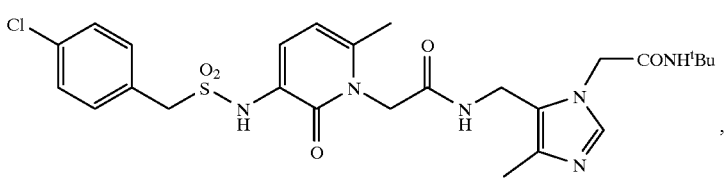,
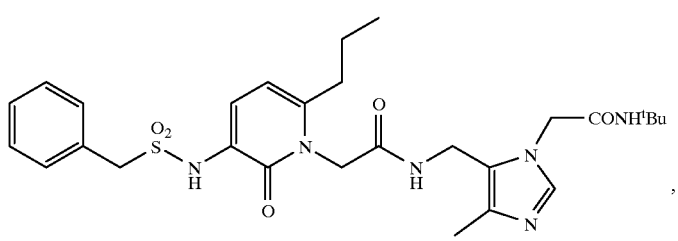,

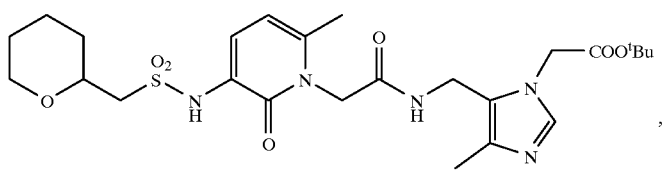,
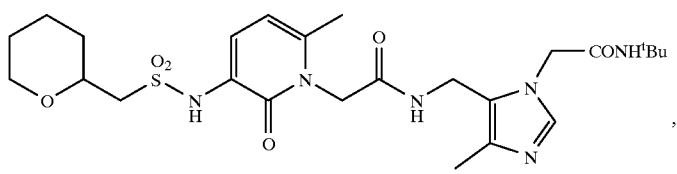,
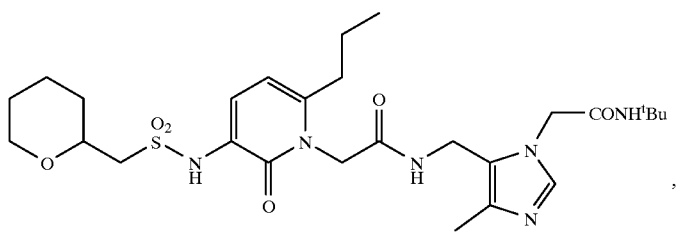,
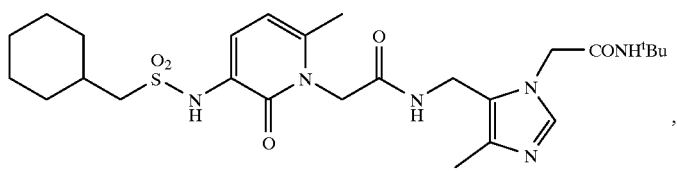,
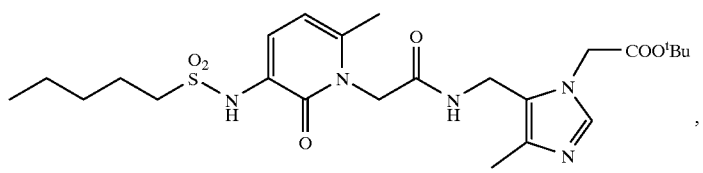,
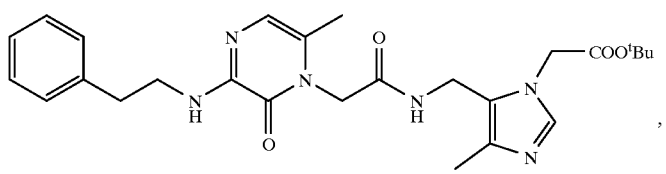,
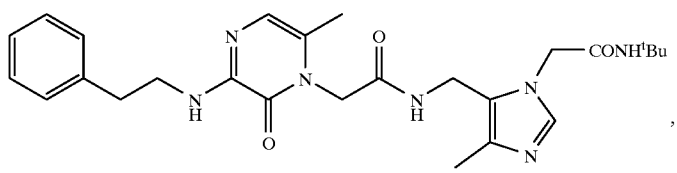,
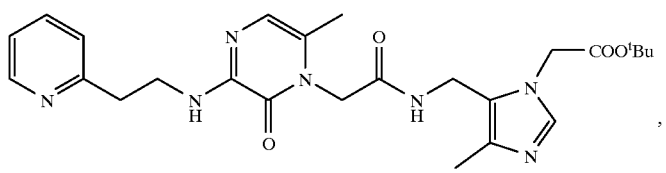,

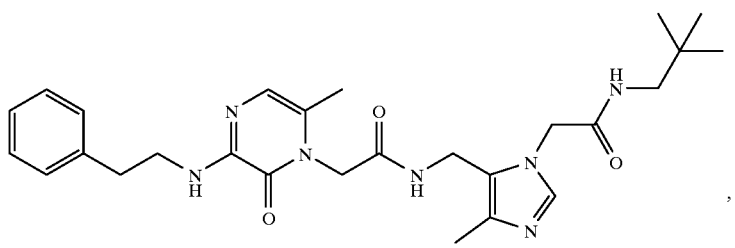,
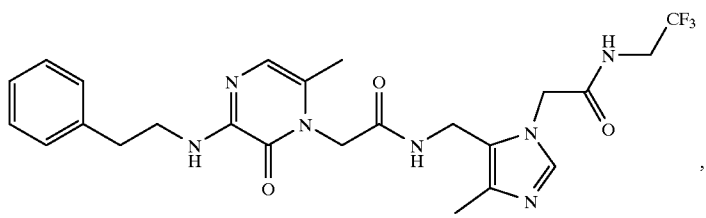,
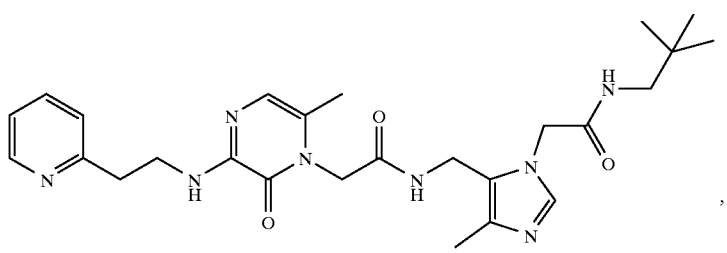,
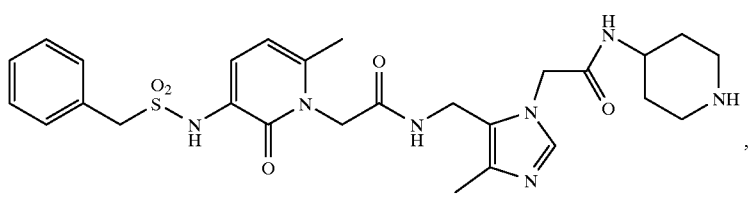,
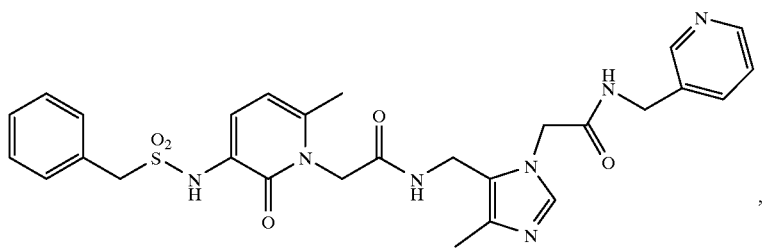,
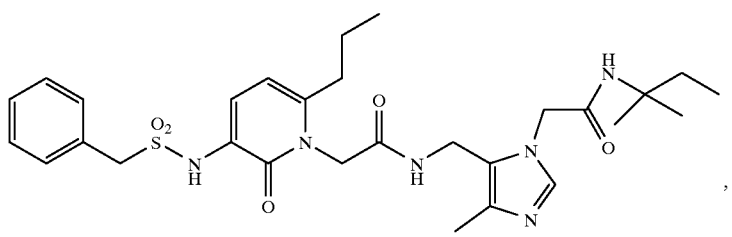,
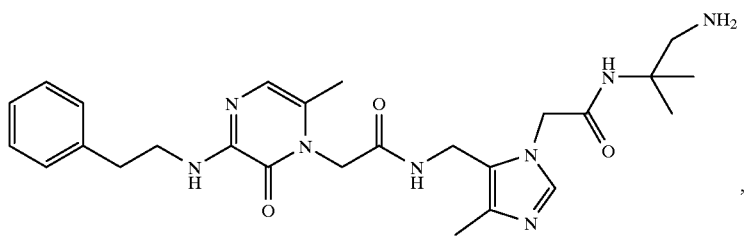,

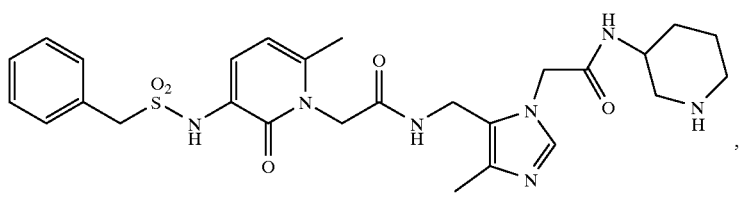,
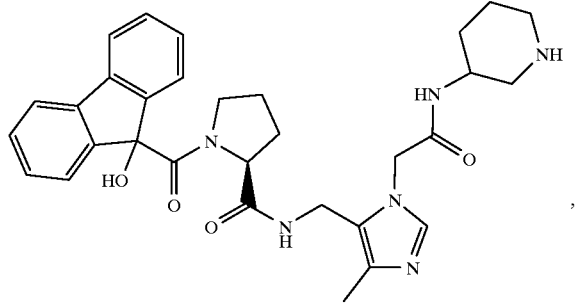,
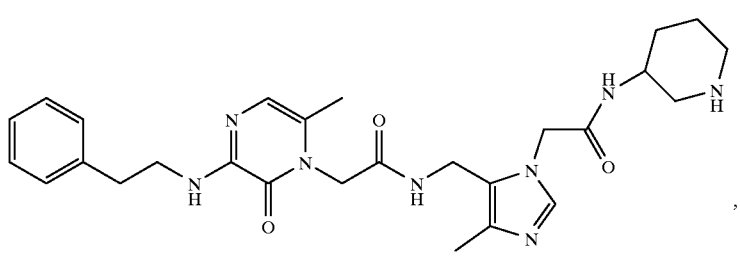,
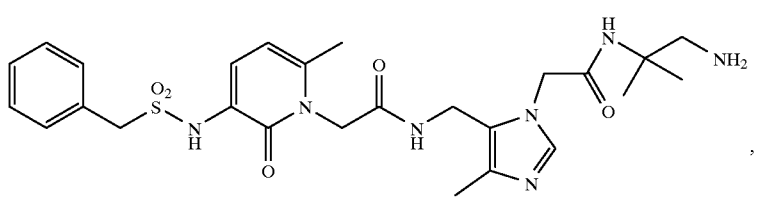,
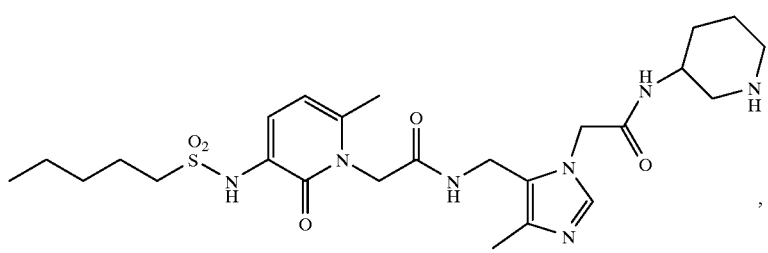,
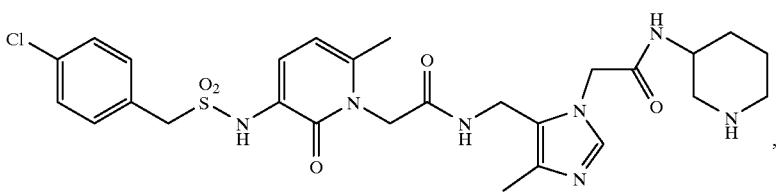,
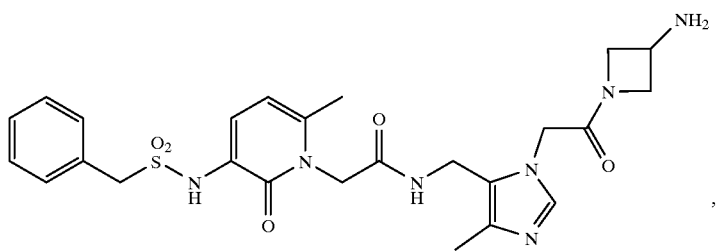,

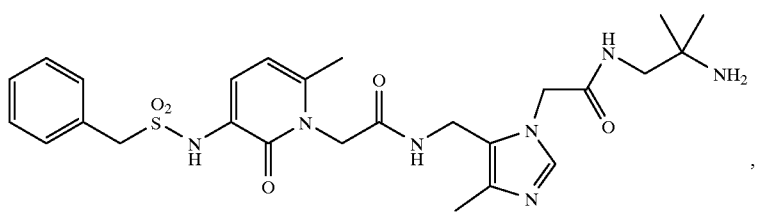,
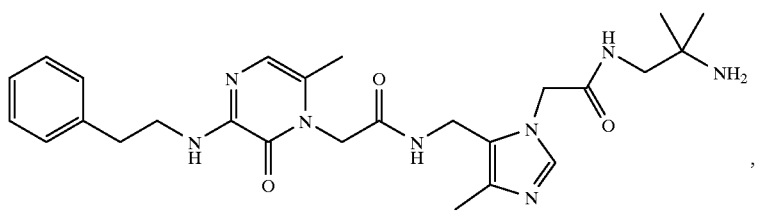,
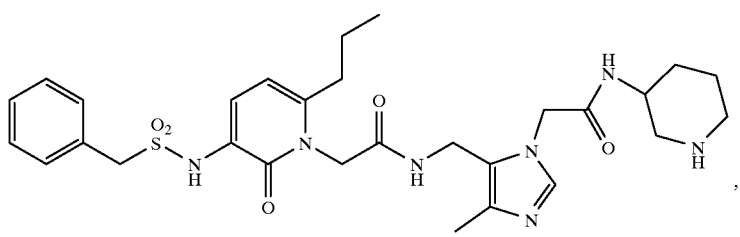,
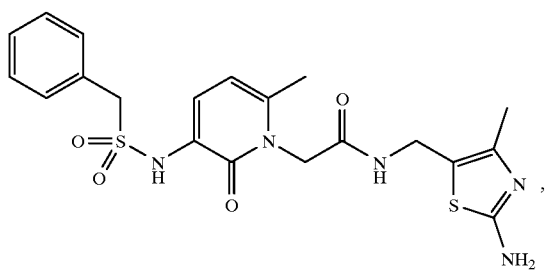,
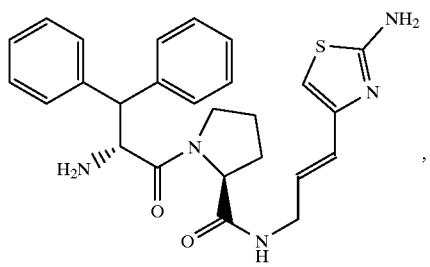,
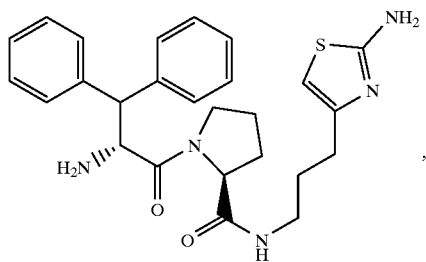,

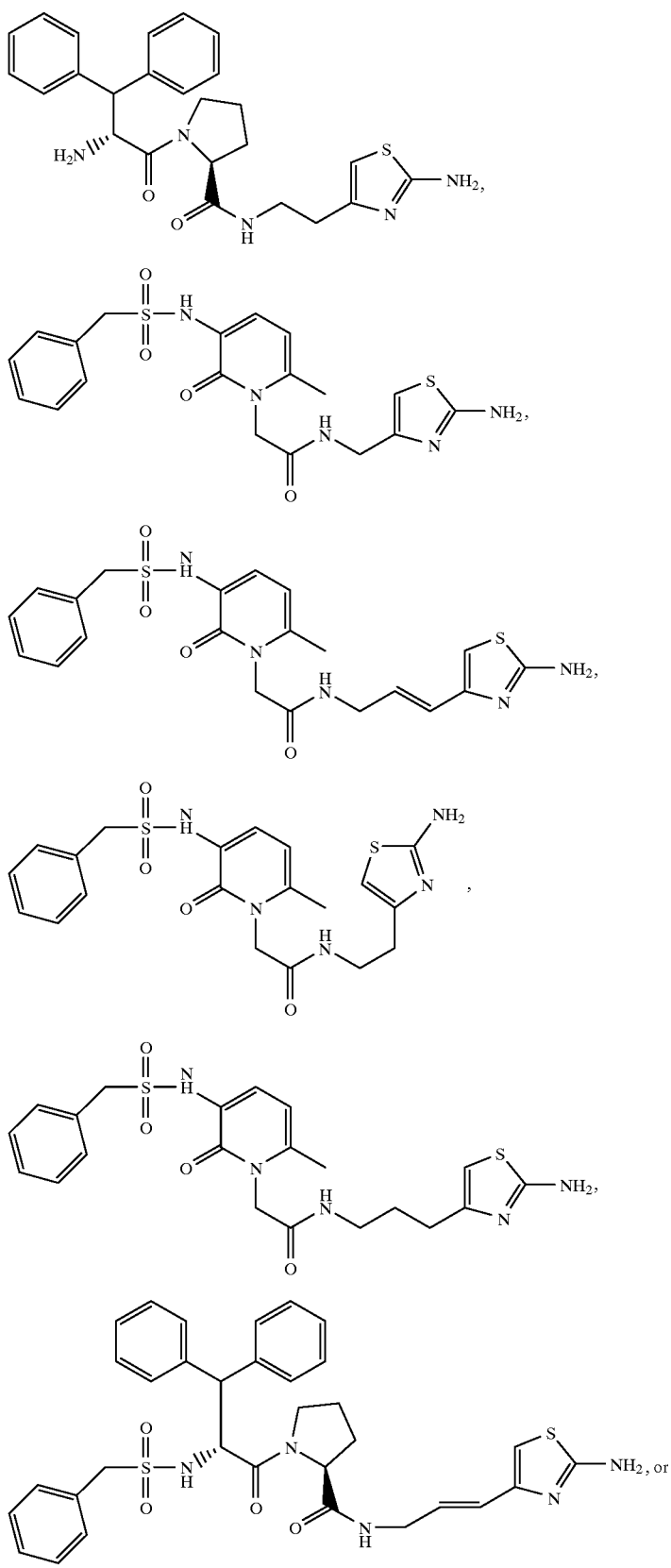

-continued

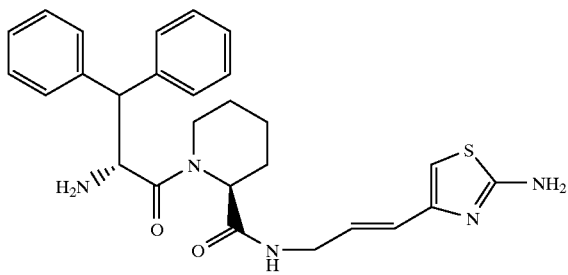

and pharmaceutically acceptable salts thereof.

3. A composition for inhibiting thrombin in blood comprising a compound of claim 1 and a pharmaceutically acceptable carrier.

4. A method for inhibiting thrombin in blood in a mammal comprising administering to the mammal a thrombin inhibiting effected amount of a composition of claim 3.

5. A method for inhibiting formation of blood platelet aggregates in blood in a mammal comprising administering to the mammal a thrombin inhibiting effective amount of a composition of claim 3.

6. A method for inhibiting formation of fibrin in blood in a mammal comprising administering to the mammal a thrombin inhibiting effective amount of a composition of claim 3.

7. A method for inhibiting thrombus formation in blood in a mammal comprising administering to the mammal a thrombin inhibiting effective amount of a composition of claim 3.

8. A method for inhibiting thrombin in stored blood comprising administering to the mammal a thrombin inhibiting effective amount of a composition of claim 3.

* * * * *